United States Patent [19]

Morimoto et al.

[11] Patent Number: 5,750,470
[45] Date of Patent: May 12, 1998

[54] HERBICIDAL 2,6-DISUBSTITUTED PYRIDINE COMPOUNDS AND COMPOSITIONS

[75] Inventors: Katsushi Morimoto, Sodegaura; Masatoshi Ohnari; Hiroyuki Furusawa, both of Narashino; Takumi Terachi, Funabashi; Tsutomu Nawamaki, Tokyo; Kimihiro Ishikawa, Yono; Kunimitsu Nakahira, Minamisaitama-gun; Chiaki Kawaguchi, Urawa, all of Japan

[73] Assignee: Nissan Chemical Industries, Ltd., Tokyo, Japan

[21] Appl. No.: 804,916

[22] Filed: Feb. 24, 1997

[30] Foreign Application Priority Data

Aug. 23, 1994 [JP] Japan ................................. 6-198429
Jul. 14, 1995 [JP] Japan ................................. 7-178740

[51] Int. Cl.⁶ .................... C07D 413/04; C07D 413/14
[52] U.S. Cl. .................. 504/253; 504/252; 546/261; 546/264; 546/268.4; 546/268.7; 546/270.4; 546/271.4; 546/272.4; 546/274.1
[58] Field of Search .................... 546/269.4, 261, 546/264, 268.4, 268.7, 270.4, 271.4, 272.4, 274.4; 504/253, 252

[56] References Cited

U.S. PATENT DOCUMENTS 4,298,602 11/1981 Pawloski ............................. 424/200
4,775,762 10/1988 Knox et al. ......................... 546/276
4,891,428 1/1990 Nordhoff et al. .................... 546/278
4,927,827 5/1990 Katoh et al. ........................ 514/256

FOREIGN PATENT DOCUMENTS 4142458 6/1992 Germany.
57-24364 2/1982 Japan.
62-123185 6/1987 Japan.

*Primary Examiner*—C. Warren Ivy
*Assistant Examiner*—Garth M. Dahlen
*Attorney, Agent, or Firm*—Foley & Lardner

[57] ABSTRACT

Provided are a pyridine derivative represented by the formula (1):

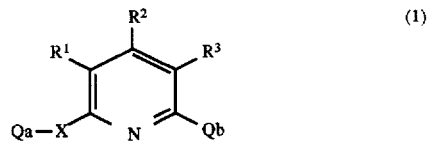

wherein $R^1$, $R^2$ and $R^3$ each independently represent a hydrogen atom, a $C_{1-6}$ alkyl group, a $C_{1-4}$ haloalkyl group, a $C_{1-4}$ alkoxy group, a cyano group, a nitro group or a halogen atom.

Qa represents a phenyl, pyrazolyl or pyridyl which may be substituted, Qb represents an azole, and X represents oxygen, sulfur or N-$R^4$.

$R^4$ represents hydrogen or an alkyl group, and an agricultural chemical containing the same, particularly a herbicide.

13 Claims, No Drawings

HERBICIDAL 2,6-DISUBSTITUTED PYRIDINE COMPOUNDS AND COMPOSITIONS

The benefit is hereby claimed of the right to an earlier effective filing date, i.e., Aug. 23, 1995 based on PCT/JP95/01666 as provided for in 35 USC § 120.

TECHNICAL FIELD

This invention relates to a novel pyridine derivative and an agricultural chemical containing the same as an active ingredient, particularly a herbicide.

BACKGROUND ART

At present, it is indispensable to use a herbicide in order to protect important crops such as rice, wheat, corn, soybean, cotton, sugar beets, etc. from weeds and achieve increase in yield. In recent years, in a cultivated field where these useful crops and weeds coexist, there has been desired a selective herbicide which does not exert chemical damage on crops and can kill only weeds selectively. Also, from the standpoints of preventing environmental pollution, reducing economical cost at the time of transportation and application, etc., search and study of compounds exhibiting a high herbicidal effect with the lowest possible dose have been continued for many years. Some of compounds having such characteristics have been used as a selective herbicide, but there has been a demand for a more excellent novel compound having these properties as before.

DISCLOSURE OF THE INVENTION

The present inventors have continued to study for many years in order to develop an agricultural chemical, particularly a herbicide having selectivity to important crops and investigated herbicidal characteristics of a large number of compounds in order to produce a compound having higher weed-killing ability and wider selectivity. As a result, they have found that a pyridine derivative (hereinafter referred to as "the compound of the present invention") represented by the formula (1):

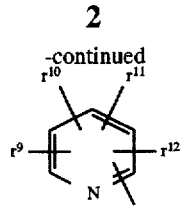

wherein $R^1$, $R^2$ and $R^3$ each independently represent a hydrogen atom, a $C_{1-6}$ alkyl group, a $C_{1-4}$ haloalkyl group, a $C_{1-4}$ alkoxy group, a cyano group, a nitro group or a halogen atom, Qa represents

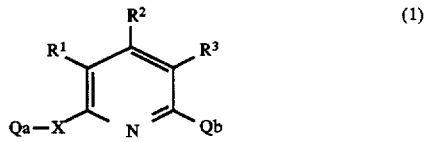

-continued

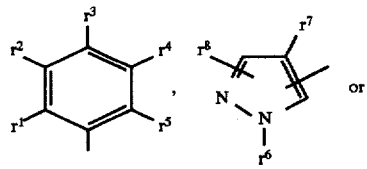

wherein $r^1$, $r^2$, $r^3$, $r^4$ and $r^5$ each independently represent a hydrogen atom, a $C_{1-4}$ alkyl group, a $C_{1-4}$ haloalkyl group, a $C_{1-4}$ alkoxy group, a cyano group, a nitro group or a halogen atom, $r^6$ represents a hydrogen atom, a $C_{1-6}$ alkyl group, a $C_{3-6}$ cycloalkyl group which may be substituted by a $C_{1-4}$ alkyl group, a $C_{2-4}$ alkenyl group, a $C_{2-4}$ alkynyl group or a $C_{1-4}$ haloalkyl group, $r^7$ and $r^8$ each independently represent a hydrogen atom, a $C_{1-6}$ alkyl group, a $C_{3-6}$ cycloalkyl group, a $C_{2-4}$ alkenyl group, a $C_{2-4}$ alkynyl group, a $C_{1-4}$ haloalkyl group, a $C_{1-4}$ alkoxycarbonyl group, a cyano group, a halogen atom or a nitro group, and $r^9$, $r^{10}$, $r^{11}$ and $r^{12}$ each independently represent a hydrogen atom, a $C_{1-4}$ alkyl group, a $C_{1-4}$ haloalkyl group, a $C_{1-4}$ alkoxy group, a cyano group, a nitro group or a halogen atom.

Qb represents

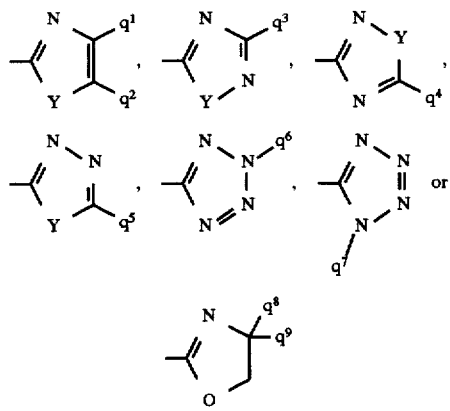

wherein $q^1$, $q^2$, $q^3$, $q^4$ and $q^5$ each independently represent a hydrogen atom, a $C_{1-6}$ alkyl group, a $C_{3-6}$ cycloalkyl group which may be substituted by a $C_{1-4}$ alkyl group or a halogen atom, a $C_{1-4}$ haloalkyl group, a $C_{1-4}$ alkoxy group, a cyano group, a nitro group, a halogen atom, a $C_{1-4}$ alkoxy $C_{1-4}$ alkyl group, a $C_{1-4}$ haloalkoxy $C_{1-4}$ alkyl group, a phenyl group, a benzyl group, a 3-pyridyl group, a $C_{1-4}$ alkoxycarbonyl group, a $C_{2-4}$ alkenyl group which may be substituted by a halogen atom, a $C_{1-4}$ haloalkoxy group, a $C_{1-4}$ alkylthio group, a $C_{1-4}$ alkylsulfinyl group, a $C_{1-4}$ alkylsulfonyl group, a $C_{2-4}$ alkenyloxy group, a $C_{3-4}$ alkynyloxy group, a $C_{1-4}$ haloalkylthio group, a $C_{2-4}$ alkenylthio group, a $C_{3-4}$ alkynylthio group, a $C_{1-4}$ alkylamino group, a $C_{2-4}$ haloalkylamino group, a di-$C_{1-4}$ alkylamino group, a carbamoyl group, a N-cyclopropylcarbamoyl group, a hydroxyl group, an epoxy group which may be substituted by a $C_{1-4}$ alkyl group, or a di-$C_{2-4}$ haloalkylamino group, $q^6$, $q^7$, $q^8$ and $q^9$ each independently represent a hydrogen atom or a $C_{1-6}$ alkyl group, Y represents an oxygen atom, a sulfur atom or N-$q^{10}$, and $q^{10}$ represents a hydrogen atom or a $C_{1-4}$ alkyl group.

X represents an oxygen atom, a sulfur atom or N-$R^4$, and $R^4$ represents a hydrogen atom or a $C_{1-4}$ alkyl group, has potent weed-killing ability to a large number of weeds and also has high safety to rice, wheat, corn, soybean, cotton, sugar beets, etc. which are important crops in either soil treatment, soil incorporation treatment or stem and foliar treatment, to accomplish the present invention.

BEST MODE FOR PRACTICING THE INVENTION

The substituents of the compound of the present invention are specifically enumerated as shown below. The symbols each represent the following meanings.

Me: a methyl group, Et: an ethyl group, Pr-n: a normal propyl group, Pr-iso: an isopropyl group, Bu-n: a normal butyl group, Bu-iso: an isobutyl group, Bu-sec: a secondary butyl group, Bu-tert: a tertiary butyl group, Pen-n: a normal pentyl group, Hex-n: a normal hexyl group, Pr-cyc: a cyclopropyl group, Bu-cyc: a cyclobutyl group, Pen-cyc: a cyclopentyl group, Hex-cyc: a cyclohexyl group, Ph: a phenyl group, Py: a pyridyl group and Epo: an epoxy group.

Specific Examples of the Substituents $R^1$, $R^2$ and $R^3$ of the Compound of the Present Invention H, Me, Et, Pr-n, Pr-iso, Bu-n, Bu-iso, Bu-sec, Bu-tert, Pen-n, Hex-n, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, OMe, OEt, OPr-n, OPr-iso, OBu-n, OBu-iso, OBu-tert, CN, $NO_2$, F, Cl, Br, I Specific Examples of the Substituent Oa of the Compound of the Present Invention

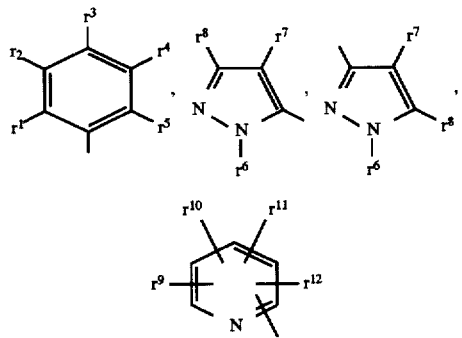

Specific Examples of the Substituent Ob of the Compound of the Present Invention

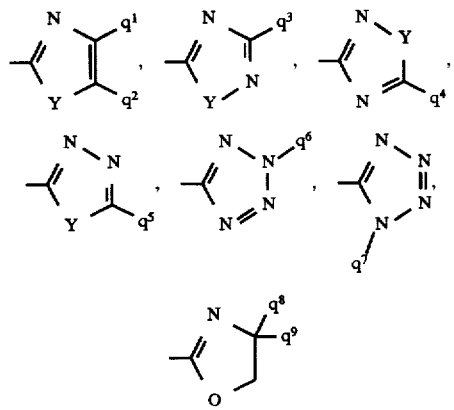

Specific Examples of the Substituents $r^1$, $r^2$, $r^3$, $r^4$ and $r^5$ of the Compound of the Present Invention H, Me, Et, Pr-n, Pr-iso, Bu-n, Bu-iso, Bu-sec, Bu-tert, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, OMe, OEt, OPr-n, OPr-iso, OBu-n, OBu-iso, OBu-tert, CN, $NO_2$, F, Cl, Br, I Specific Examples of the Substituent $r^6$ of the Compound of the Present Invention H, Me, Et, Pr-n, Pr-iso, Bu-n, Bu-iso, Bu-sec, Bu-tert, Pen-n, Hex-n, Pr-cyc, Bu-cyc, Pen-cyc, Hex-cyc, $CH_2CH=CH_2$, $CH_2CH=CHMe$, $CH_2CH_2CH=CH_2$, $CH_2C\equiv CH$, $CH_2C\equiv CMe$, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$ Specific Examples of the Substituents $r^7$ and $r^8$ of the Compound of the Present Invention H, Me, Et, Pr-n, Pr-iso, Bu-n, Bu-iso, Bu-sec, Bu-tert, Pen-n, Hex-n, Pr-cyc, Bu-cyc, Pen-cyc, Hex-cyc, $CH_2CH=CH_2$, $CH_2CH=CHMe$, $CH_2CH_2CH=CH_2$, $CH_2C\equiv CH$, $CH_2C\equiv CMe$, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, $CO_2Me$, $CO_2Et$, $CO_2Pr-n$, $CO_2Pr-iso$, $CO_2Bu-n$, CN, $NO_2$, F, Cl, Br, I Specific Examples of the Substituents $r^9$, $r^{10}$, $r^{11}$ and $r^{12}$ of the Compound of the Present Invention H, Me, Et, Pr-n, Pr-iso, Bu-n, Bu-iso, Bu-sec, Bu-tert, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, OMe, OEt, OPr-n, OPr-iso, OBu-n, OBu-iso, OBu-tert, CN, $NO_2$, F, Cl, Br, I Specific Examples of the Substituents $\alpha^1$, $\alpha^2$, $\alpha^3$, $\alpha^4$ and $\alpha^5$ of the Compound of the Present Invention H, Me, Et, Pr-n, Pr-iso, Bu-n, Bu-iso, Bu-sec, Bu-tert, Pen-n, Hex-n, Pr-cyc, Bu-cyc, Pen-cyc, Hex-cyc, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, OMe, OEt, OPr-n, OPr-iso, OBu-n, OBu-iso, OBu-tert, CN, $NO_2$, F, Cl, Br, I, $CH_2OMe$, $CH_2CH_2OMe$, $CH_2CH_2CH_2OMe$, $CH_2CH_2CH_2CH_2OMe$, $CH_2OEt$, $CH_2OPr-n$, $CH_2OBu-n$, $CH_2OCH_2CF_3$, $CH_2CH_2OCH_2CF_3$, $CH_2CH_2CH_2OCH_2CF_3$, $CH_2CH_2CH_2CH_2OCH_2CF_3$, $CH_2OCH_2CH_2F$, $CH_2OCH_2CH_2Cl$, $CH_2OCH_2CH_2Br$, Ph, $PhCH_2$, 3-Py, $CO_2Me$, $CO_2Et$, $CO_2Pr-n$, $CO_2Bu-n$, $CH=CH_2$, $CH=CHMe$, $CH=CMe_2$, $CH_2CH=CH_2$, $CH_2CH=CHMe$, $OCH_2F$, $OCHF_2$, $OCF_3$, $OCBrF_2$, $OCH_2CF_3$, $OCF_2CF_3$, $OCH_2CH_2Cl$, $OCH_2CHCl_2$, $OCH_2CH_2CF_3$, $OCH_2CF_2CF_3$, $OCF_2CF_2CF_3$, $OCH_2CH_2CH_2Cl$, SMe, SEt, SPr-n, SPr-iso, SBu-n, $S(O)Me$, $S(O)Et$, $S(O)Pr-n$, $S(O)Pr-iso$, $S(O)Bu-n$, $SO_2Me$, $SO_2Et$, $SO_2Pr-n$, $SO_2Pr-iso$, $SO_2Bu-n$, $OCH=CH_2$, $OCH=CHMe$, $OCH=CMe_2$, $OCH_2CH=CH_2$, $OCH_2CH=CHMe$, $OCH_2C\equiv CH$, $OCH_2C\equiv CMe$, $SCH_2F$, $SCHF_2$, $SCF_3$, $SCBrF_2$, $SCH_2CF_3$, $SCF_2CF_3$, $SCH_2CH_2Cl$, $SCH_2CHCl_2$, $SCH_2CH_2CF_3$, $SCH_2CF_2CF_3$, $SCF_2CF_2CF_3$, $SCH_2CH_2CH_2CH_2Cl$, $SCH=CH_2$, $SCH=CHMe$, $SCH=CMe_2$, $SCH_2CH=CH_2$, $SCH_2CH=CHMe$, $SCH_2C\equiv CH$, $SCH_2C\equiv CMe$, $NHMe$, $NHEt$, $NHPr$-n, $NHPr$-iso, $NHBu$-n, $NHCH_2CF_3$, $NHCF_2CF_3$, $NHCH_2CH_2Cl$, $NHCH_2CHCl_2$, $NHCH_2CH_2CF_3$, $NHCH_2CF_2CF_3$, $NHCF_2CF_2CF_3$, $NHCH_2CH_2CH_2CH_2Cl$, $NMe_2$, $NEt_2$, $N(Pr$-n$)_2$, $N(Pr$-iso$)_2$, $N(Bu$-n$)_2$, $N(CH_2CF_3)_2$, $N(CF_2CF_3)_2$, $N(CH_2CH_2Cl)_2$, $N(CH_2CHCl_2)_2$, $N(CH_2CH_2CF_3)_2$, $N(CH_2CF_2CF_3)_2$, $N(CF_2CF_2CF_3)_2$, $N(CH_2CH_2CH_2CH_2Cl)_2$, 2-Me-Pr-cyc, $CMe=CH_2$, $CONH_2$, $CONH$-Py-cyc, $OH$, Epo, 1-Me-Epo, $CF_2Br$, $CF_2I$, $CFMe_2$, $CH(CF_3)_2$, $CH(CF_3)Me$, $CF_2Me$, $CHFMe$, 2-F-Pr-cyc, 2,2-$F_2$-Pr-cyc, 2,2,3,3-$F_4$-Pr-cyc, 2-Cl-Pr-cyc, 2,2-$Cl_2$-Pr-cyc, $CH=CF_2$ Specific Examples of the Substituents $\alpha^6$, $\alpha^7$, $\alpha^8$ and $\alpha^9$ of the Compound of the Present Invention H, Me, Et, Pr-n, Pr-iso, Bu-n, Bu-iso, Bu-sec, Bu-tert, Pen-n, Hex-n Specific Examples of the Substituents X and Y of the Compound of the Present Invention O, S, NH, NMe, NEt, NPr-n, NPr-iso, NBu-n, NBu-iso, NBu-sec, NBu-tert The compound of the present invention can be prepared easily by selecting either method of Reaction schemes 1 to 10 shown below.

Reaction Scheme 1

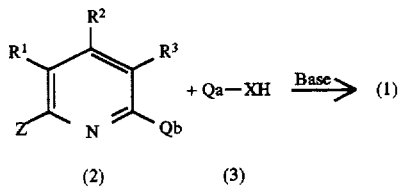

wherein Qa, Qb, $R^1$, $R^2$, $R^3$ and X represents the same meanings as described above, and Z represents a halogen atom.

That is, the compound (1) of the present invention can be synthesized by reacting the 6-halogenopyridine (2) with the nucleophilic reagent (3) in the presence of a base.

As the base, there may be used inorganic bases such as sodium hydroxide, potassium hydroxide, potassium carbonate, sodium hydride, etc., metal alkoxides such as sodium methoxide, sodium ethoxide, potassium butoxide, etc., metal amides such as sodium amide, potassium amide, lithium diisopropylamide, etc., organic metals such as methyl lithium, n-butyl lithium, etc. or organic bases such as pyridine, triethylamine, DBU, etc.

Also, by adding copper powder, copper oxide or a copper salt such as copper chloride, copper iodide, etc. together with the above bases, the reaction may be accelerated in some cases.

This reaction proceeds without a solvent, but a solvent may be used, if necessary. The solvent to be used is not particularly limited so long as it is inert to the reaction, and there may be mentioned, for example, aliphatic or aromatic hydrocarbons such as hexane, cyclohexane, benzene, toluene, etc., ethers such as diethyl ether, diisopropyl ether, dioxane, tetrahydrofuran, etc., ketones such as acetone, methyl ethyl ketone, methyl isobutyl ketone, etc., nitrites such as acetonitrile, propionitrile, etc., acid amides such as N,N-dimethylformamide, N,N-dimethylacetamide, etc., sulfur-containing polar solvents such as dimethylsulfoxide, sulforane, etc., and organic bases such as pyridine, etc.

The reaction temperature is generally −50° C. to 200° C., preferably 10° C. to 150° C.

A synthetic example of the 6-halogenopyridine (2) which is a starting material of Reaction scheme 1 is shown in Reaction scheme 2.

Reaction scheme 2

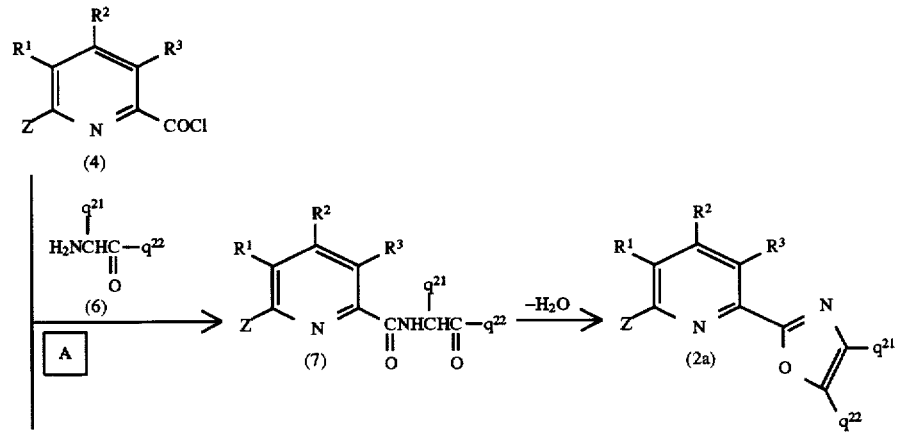

-continued
Reaction scheme 2
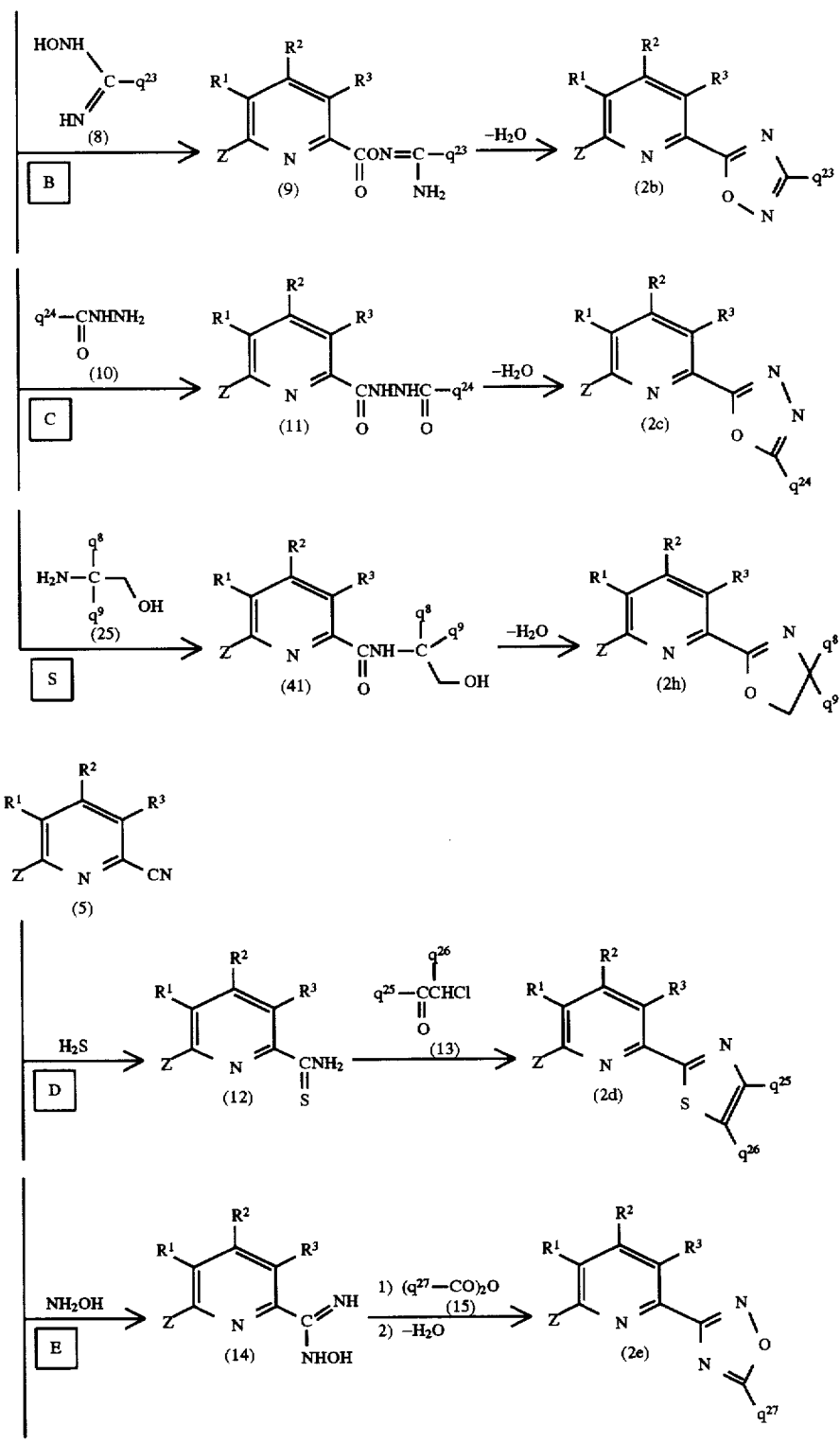

-continued
Reaction scheme 2

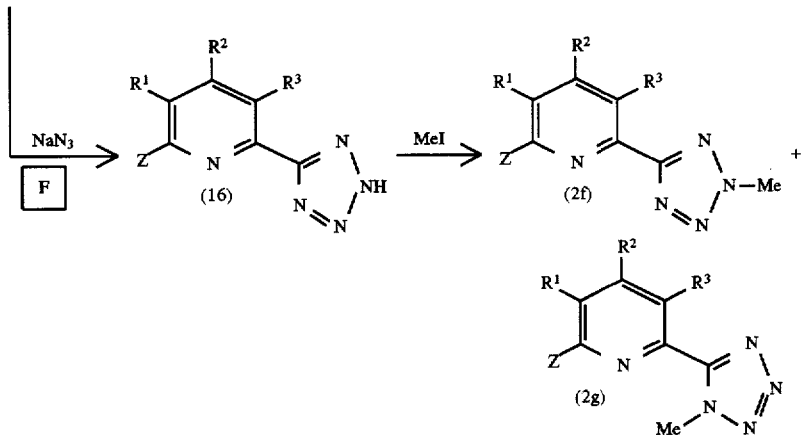

wherein $R^1$, $R^2$, $R^3$, $q^8$, $q^9$ and Z each represent the same meanings as described above, $q^{21}$, $q^{22}$, $q^{23}$, $q^{24}$, $q^{25}$, $q^{26}$ and $q^{27}$ each represent a $C_{1-4}$ alkyl group, a $C_{1-4}$ haloalkyl group, a $C_{1-4}$ alkoxy $C_{1-4}$ alkyl group, a $C_{1-4}$ haloalkoxy $C_{1-4}$ alkyl group, a phenyl group, a benzyl group, a 3-pyridyl group, a $C_{2-4}$ alkenyl group or a $C_{1-4}$ alkoxycarbonyl group.

Step A: A 6-halogenopyridine-2-carboxylic acid chloride (4) and an aminoketone (6) are reacted to prepare an acylaminoketone (7). (7) is reacted with a dehydrating agent such as sulfuric acid, phosphorus pentachloride, phosphorus oxychloride or polyphosphoric acid, etc. to obtain the 6-halogeno-2-(oxazol-2-yl)pyridine (2a).

Step B: The 6-halogenopyridine-2-carboxylic acid chloride (4) and an amidoxime (8) are reacted to prepare a picolinate (9). (9) is heated or reacted with a dehydrating agent such as sulfuric acid, phosphorus pentachloride, phosphorus oxychloride or polyphosphoric acid, etc. to obtain the 6-halogeno-2-(1,2,4-oxadiazol-5-yl)pyridine (2b).

Step C: The 6-halogenopyridine-2-carboxylic acid chloride (4) and an acylhydrazide (10) are reacted to prepare a 1,2-diacylhydrazide (11). (11) is reacted with a dehydrating agent such as sulfuric acid, phosphorus pentachloride, phosphorus oxychloride or polyphosphoric acid, etc. to obtain the 6-halogeno-2-(1,3,4-oxadiazol-2-yl)pyridine (2c).

Step D: After a 6-halogenopyridine-2-carbonitrile (5) is reacted with hydrogen sulfide to prepare a thioamide (12), it is reacted with a haloketone (13) to obtain a 6-halogeno-2-(thiazol-2-yl)pyridine (2d).

Step E: After the 6-halogenopyridine-2-carbonitrile (5) is reacted with hydroxylamine to prepare an amidoxime (14), it is reacted with a carboxylic acid anhydride (15) to obtain a 6-halogeno-2-(1,2,4-oxathiazol-3-yl)pyridine (2e).

Step F: After the 6-halogenopyridine-2-carbonitrile (5) is reacted with sodium azide to prepare a tetrazolylpyridine (16), it is methylated with methyl iodide, etc. to obtain N-methyltetrazolylpyridines (2f) and (2g).

Step S: The 6-halogenopyridine-2-carboxylic acid chloride (4) and an aminoalcohol (25) are reacted to prepare an amide (41). (41) is dehydrated to obtain a 6-halogeno-2-(oxazolin-2-yl)pyridine (2h).

Reaction scheme 3

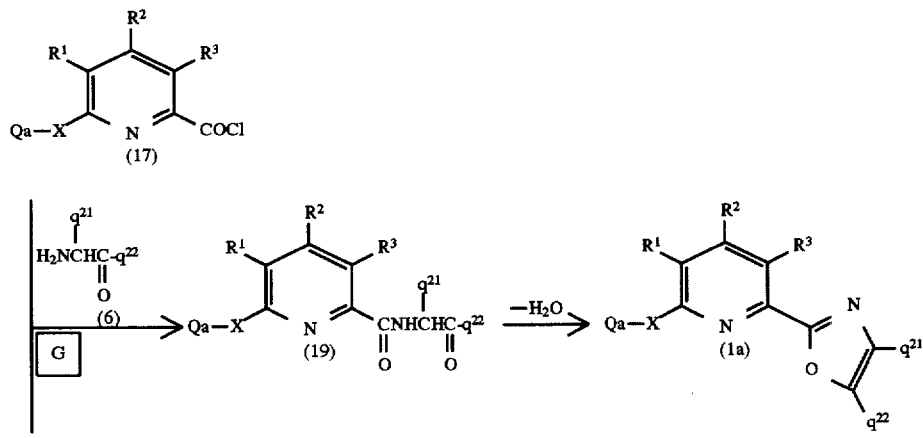

-continued
Reaction scheme 3
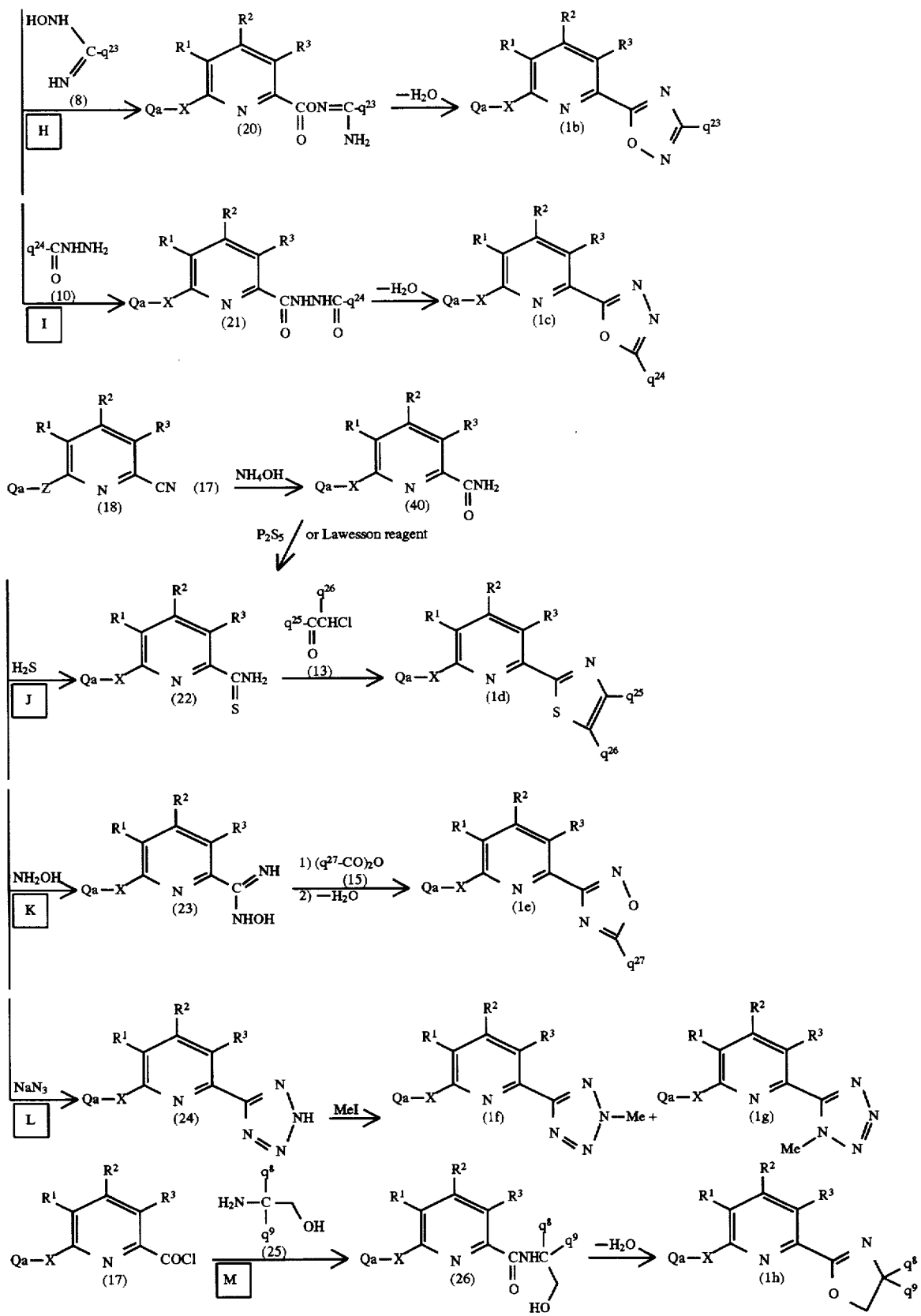

Reaction scheme 3

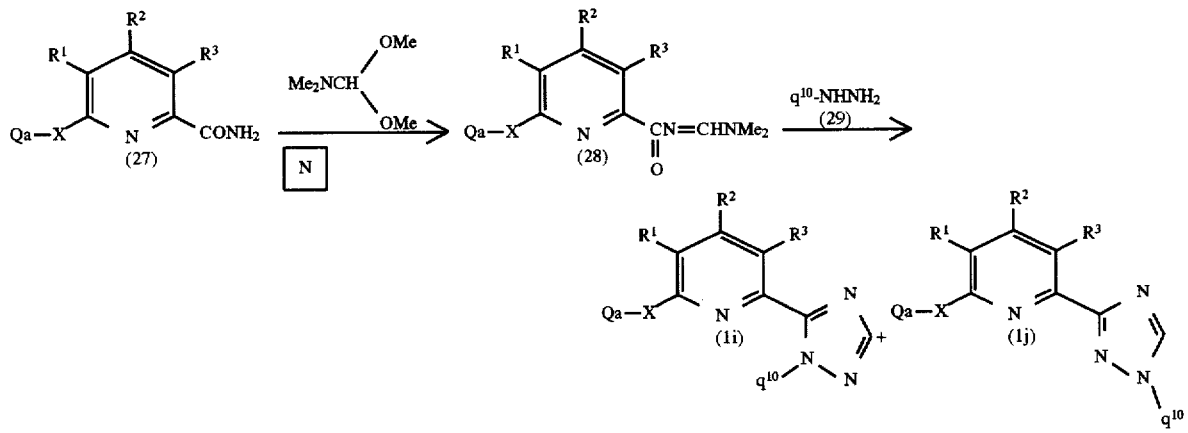

wherein Qa, X, R¹, R², R³, q⁸, q⁹, q¹⁰, q²¹, q²², q²³, q²⁴, q²⁵, q²⁶ and q²⁷ each represent the same meanings as described above.

Step G: A 6-substituted pyridine-2-carboxylic acid chloride (17) and an aminoketone (6) are reacted to prepare an acylaminoketone (19). (19) is reacted with a dehydrating agent such as sulfuric acid, phosphorus pentachloride, phosphorus oxychloride or polyphosphoric acid, etc. to obtain a 6-substituted-2-(oxazol-2-yl)pyridine (1a) which is a part of the compound of the present invention.

Step H: The 6-substituted pyridine-2-carboxylic acid chloride (17) and an amidoxime (8) are reacted to prepare a picolinate (20). (20) is heated or reacted with a dehydrating agent such as sulfuric acid, phosphorus pentachloride, phosphorus oxychloride or polyphosphoric acid, etc. to obtain a 6-substituted-2-(1,2,4-oxadiazol-5-yl)pyridine (1b) which is a part of the compound of the present invention.

Step I: The 6-substituted pyridine-2-carboxylic acid chloride (17) and an acylhydrazide (10) are reacted to prepare a 1,2-diacylhydrazide (21). (21) is reacted with a dehydrating agent such as sulfuric acid, phosphorus pentachloride, phosphorus oxychloride or polyphosphoric acid, etc. to obtain a 6-substituted-2-(1,3,4-oxadiazol-2-yl)pyridine (1c) which is a part of the compound of the present invention.

Step J: After a 6-substituted pyridine-2-carbonitrile (18) is reacted with hydrogen sulfide to prepare a thioamide (22), it is reacted with a haloketone (13) to obtain a 6-substituted-2-(thiazol-2-yl)pyridine (1d) which is a part of the compound of the present invention. (22) which is a starting material of this reaction can be also synthesized by reacting a 6-substituted pyridine-2-carboxylic acid amide (40) obtained by a reaction of (17) and aqueous ammonia, with phosphorus pentadisulfide or a Lawesson reagent.

Step K: After the 6-substituted pyridine-2-carbonitrile (18) is reacted with hydroxylamine to prepare an amidoxime (23), it is reacted with a carboxylic acid anhydride (15) to obtain a 6-substituted-2-(1,2,4-oxadiazol-3-yl)pyridine (1e) which is a part of the compound of the present invention.

Step L: After the 6-substituted pyridine-2-carbonitrile (18) is reacted with sodium azide to prepare a tetrazolylpyridine (24), it is methylated with methyl iodide, etc. to obtain N-methyltetrazolylpyridines (1f) and (1g) which are a part of the compound of the present invention.

Step M: The 6-substituted pyridine-2-carboxylic acid chloride (17) and an aminoalcohol (25) are reacted to prepare an amide (26). (26) is dehydrated to obtain a 6-substituted-2-(oxazolin-2-yl)pyridine (1h) which is a part of the compound of the present invention.

Step N: A 6-substituted pyridine-2-carboxylic acid amide (27) and N,N-dimethylformamidoacetal are reacted to prepare a formamidine (28). (28) is reacted with a hydrazine (29) to obtain a 6-substituted-2-(1,2,4-triazol-5-yl)pyridine (1i) or a 6-substituted-2-(1,2,4-triazol-3-yl)pyridine (1j) which is a part of the compound of the present invention.

Reaction Scheme 4

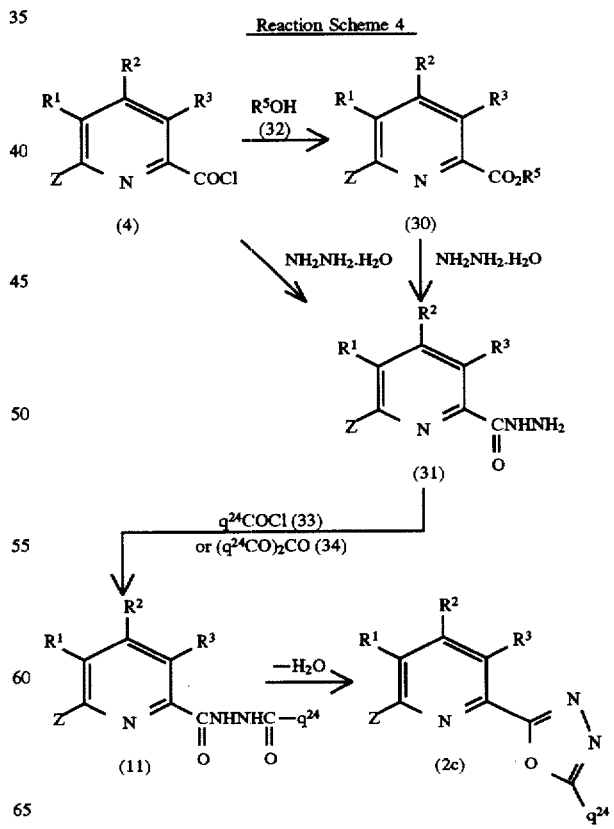

-continued
Reaction Scheme 4

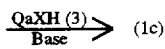

wherein Qa, $R^1$, $R^2$, $R^3$, X, Z and $q^{24}$ each represent the same meanings as described above, and $R^5$ represents a $C_{1-4}$ alkyl group or a phenyl group.

A 6-halogenopyridine-2-carboxylic acid chloride (4) and an alcohol (32) are reacted to prepare a 6-halogenopyridine-2-carboxylate (30), and (30) is reacted with hydrazine hydrate to obtain a hydrazide (31). Also, (31) can be synthesized by a reaction of (4) and hydrazine hydrate. Further, after the hydrazide (31) is reacted with an acyl chloride (33) or a carboxylic acid anhydride (34) to prepare a 1,2-diacylhydrazide (11), it is converted into a 6-halogeno-2-(1,3,4-oxadiazol-2-yl)pyridine (2c) by the method of Step C of Reaction scheme 2. In the presence of a base, (2c) is reacted with a nucleophilic reagent (3) to obtain a 6-substituted-2-(1,3,4-oxadiazol-2-yl)pyridine (1c) which is a part of the compound of the present invention. The reaction conditions are similar to Reaction scheme 1.

Reaction scheme 5

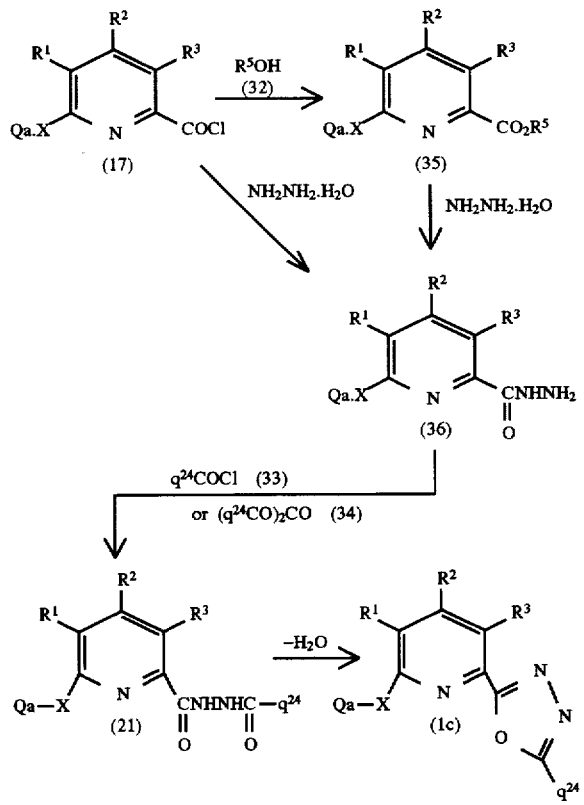

wherein Qa, $R^1$, $R^2$, $R^3$, X and $q^{24}$ each represent the same meanings as described above, and $R^5$ represents a $C_{1-4}$ alkyl group or a phenyl group.

A 6-substituted pyridine-2-carboxylic acid chloride (17) and an alcohol (32) are reacted to prepare a 6-substituted pyridine-2-carboxylate (35), and (35) is reacted with hydrazine hydrate to obtain a hydrazide (36). Also, (36) can be synthesized by a reaction of (17) and hydrazine hydrate. Further, after the hydrazide (36) is reacted with an acyl chloride (33) or a carboxylic acid anhydride (34) to prepare a 1,2-diacylhydrazide (21), a 6-substituted-2-(1,3,4-oxadiazol-2-yl)pyridine (1c) which is a part of the compound of the present invention is obtained by the method of Step I of Reaction scheme 3.

Reaction scheme 6

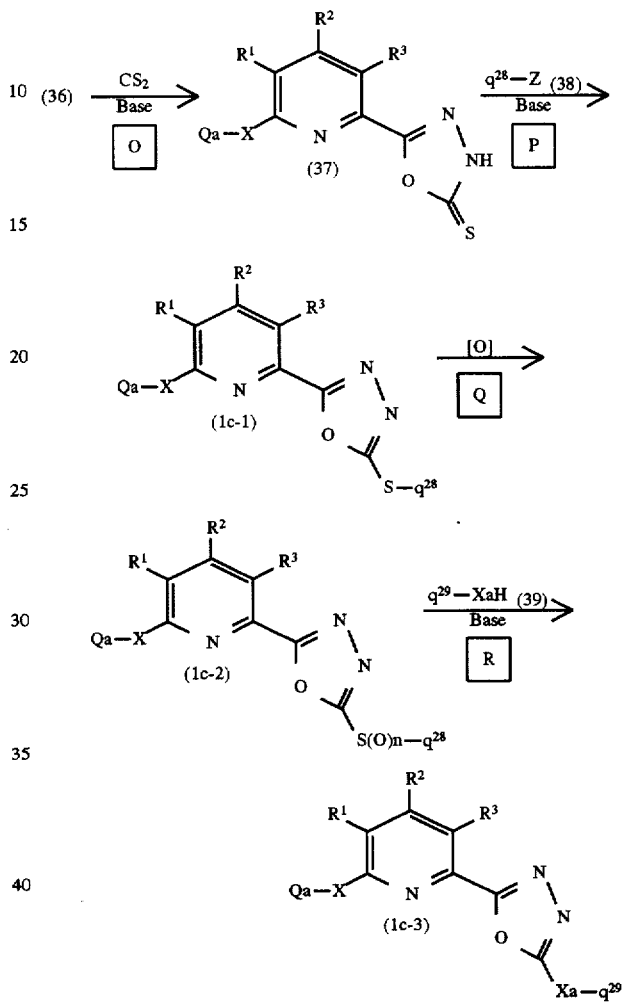

wherein Qa, $R^1$, $R^2$, $R^3$, X and Z each represent the same meanings as described above, $q^{28}$ and $q^{29}$ each independently represent a $C_{1-4}$ alkyl group or a $C_{1-4}$ haloalkyl group, n represents an integer of 1 or 2, Xa represents an oxygen atom, a sulfur atom or N-$q^{10}$, and $q^{10}$ represents the same meaning as described above.

Step O: In the presence of a base, a carboxylic acid hydrazide (36) is reacted with carbon disulfide to prepare a 1,3,4-oxadiazolin-5-thione (37). As the base, there may be used inorganic bases such as sodium hydroxide, potassium hydroxide, etc.

Step P: In the presence of a base, the 1,3,4-oxadiazolin-5-thione (37) is reacted with an alkyl halide (38) to obtain a 6-substituted-2-(5-alkylsulfenyl-1,3,4-oxadiazol-2-yl) pyridine (1c-1) which is a part of the compound of the present invention. As the base, there may be used inorganic bases such as sodium hydroxide, potassium hydroxide, potassium carbonate, sodium hydride, etc., and metal alkoxides such as sodium methoxide, sodium ethoxide, potassium butoxide, etc.

Step Q: The 6-substituted-2-(5-alkylsulfenyl-1,3,4-oxadiazol-2-yl)pyridine (1c-1) is reacted with an oxidizer to obtain a 6-substituted-2-(5-alkylsulfinyl or 5-alkylsulfonyl-1,3,4-oxadiazol-2-yl)pyridine (1c-2) which is a part of compound of the present invention. As the oxidizer, there may be used percarboxylic acids such as peracetic acid, m-chloroperbenzoic acid, etc., an inorganic oxidizer such as potassium permanganate, etc., and hydrogen peroxide.

Step R: A 6-substituted-2-(5-substituted-1,3,4-oxadiazol-2-yl)pyridine (1c-3) which is a part of the compound of the present invention can be synthesized by reacting the 6-substituted-2-(5-alkylsulfinyl or 5-alkylsulfonyl-1,3,4-oxadiazol-2-yl)pyridine (1c-2) with a nucleophilic reagent (39) in the presence of a base. As the base, there may be used inorganic bases such as sodium hydroxide, potassium hydroxide, potassium carbonate, sodium hydride, etc., and metal alkoxides such as sodium methoxide, sodium ethoxide, potassium butoxide, etc.

Reaction scheme 7

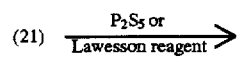

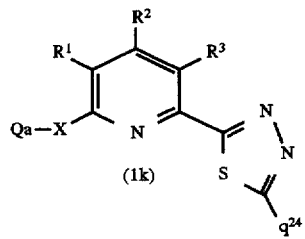

wherein Qa, $R^1$, $R^2$, $R^3$, X and $q^{24}$ each represent the same meanings as described above.

A 6-substituted-2-(1,3,4-thiadiazol-2-yl)pyridine (1k) which is a part of the compound of the present invention can be synthesized by reacting a 1,2-diacylhydrazide (21) with phosphorus pentadisulfide or a Lawesson reagent.

Reaction scheme 8

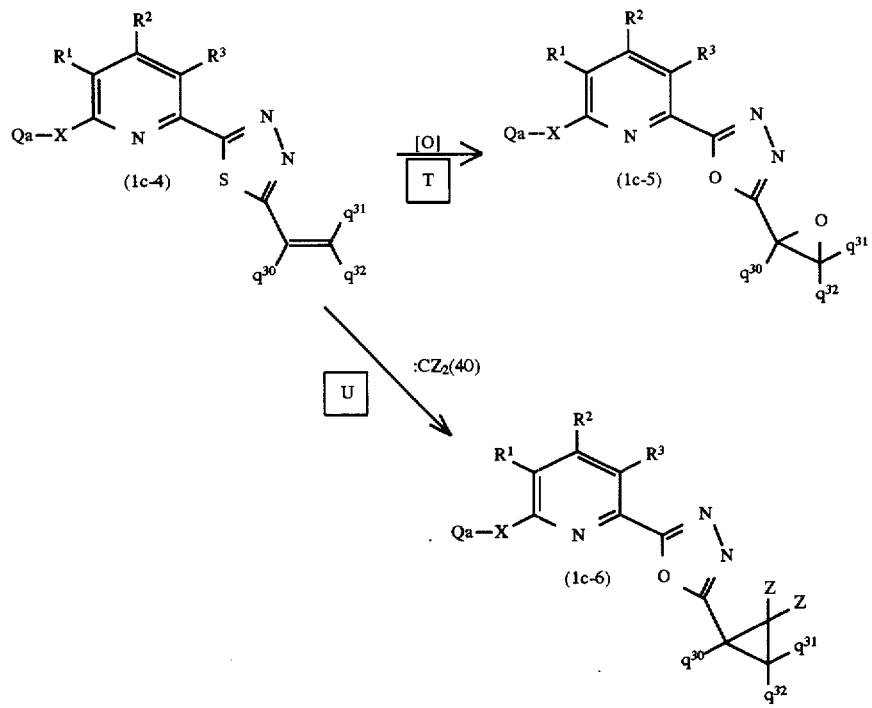

wherein Qa, X, $R^1$, $R^2$, $R^3$ and Z each represent the same meanings as described above, and $q^{30}$, $q^{31}$ and $Q^{32}$ each independently represent a hydrogen atom, a methyl group or an ethyl group.

Step T: A 6-substituted-2-(5-alkenyl-1,3,4-oxadiazol-2-yl)pyridine (1c-4) is reacted with an oxidizer to obtain an oxirane derivative (1c-5) which is a part of the compound of the present invention. As the oxidizer, there may be used percarboxylic acids such as peracetic acid, m-chloroperbenzoic acid, etc.

Step U: The 6-substituted-2-(5-alkenyl-1,3,4-oxadiazol-2-yl)pyridine (1c-4) is reacted with a halocarben (40) to obtain a 2,2-dihalogenocyclopropane derivative (1c-6) which is a part of the compound of the present invention. As the halocarben (40), there may be mentioned difluorocarben or dichlorocarben.

Reaction scheme 9

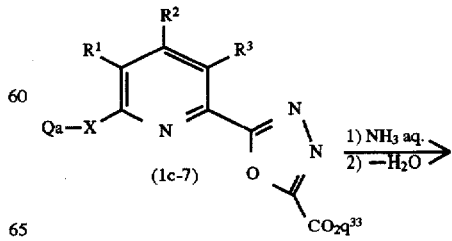

19

-continued
Reaction scheme 9

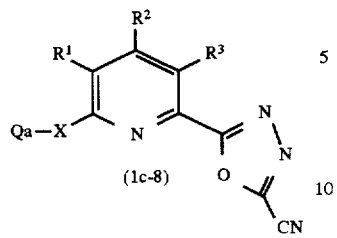

wherein Qa, X, R$^1$, R$^2$ and R$^3$ each represent the same meanings as described above, and q$^{33}$ represents a C$_{1-4}$ alkyl group.

A 6-substituted-2-(5-alkoxycarbonyl-1,3,4-oxadiazol-2-yl)pyridine (1c-7) is amidated and then dehydrated to obtain a 6-substituted-2-(5-cyano-1,3,4-oxadiazol-2-yl)pyridine (1c-8) which is a part of the compound of the present invention.

Reaction scheme 10

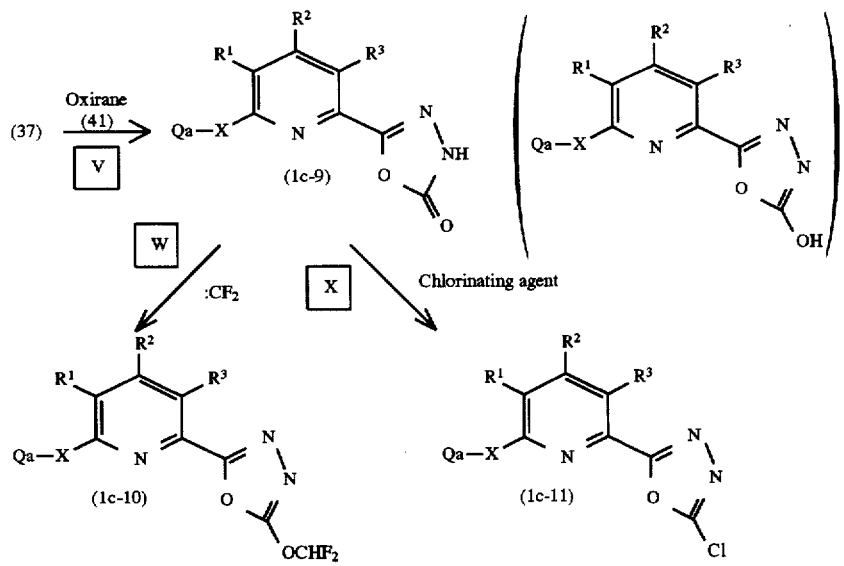

wherein Qa, X, R$^1$, R$^2$ and R$^3$ each represent the same meanings as described above.

Step V: In the presence of a base, a 1,3,4-oxadiazolin-5-thione (37) is reacted with an oxirane (41) to obtain a 1,3,4-oxadiazolin-5-one (a 5-hydroxy-1,3,4-oxadiazole) (1c-9). As the oxirane (41) to be used, there may be mentioned ethylene oxide, propylene oxide or cyclohexene oxide, etc.

Step W: The 5-hydroxy-1,3,4-oxadiazole (1c-9) is reacted with difluorocarben to obtain a 6-substituted-2-(5-difluoromethoxy-1,3,4-oxadiazol-2-yl)pyridine (1c-10) which is a part of the compound of the present invention.

Step X: The 5-hydroxy-1,3,4-oxadiazole (1c-9) is reacted with a chlorinating agent such as phosphorus oxychloride, phosphorus pentachloride or thionyl chloride, etc. to obtain a 6-substituted-2-(5-chloro-1,3,4-oxadiazol-2-yl)pyridine (1c-11) which is a part of the compound of the present invention.

The 6-substituted-pyridine-2-carboxylic acid chloride (17) and the 6-substituted-pyridine-2-carbonitrile (18)

20 which are starting materials of Reaction scheme 3 and Reaction scheme 5 can be synthesized by referring to WO94/08991, Japanese Provisional Patent Publication No. 217959/1992 or EP-0537816.

EXAMPLES

In the following, synthetic examples of the compound of the present invention are described in detail as Examples, but the present invention is not limited thereby.

Example 1

(1) Syntheses of trifluoroacetamide O-(6-chloropicolinoyl) oxime and pentafluoropropionamide O-(6-chloropicolinoyl) oxime

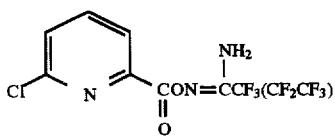

To 50 ml of tetrahydrofuran (THF) were added 7.6 g (44 mmol) of a mixture of trifluoroacetamidoxime/pentafluoropropionamidoxime=1/2 and 4.4 g (44 mmol) of triethylamine, and 7.0 g (40 mmol) of 6-chloropicolinoyl chloride dissolved in THF (50 ml) was added dropwise thereto at −20° C. After stirring the mixture at room temperature for 2 hours, the precipitated solid was filtered off and the solid obtained by removing the solvent by evaporation was washed with water and dried to obtain 10.5 g of a mixture of the desired compounds.

(2) Syntheses of 2-chloro-6-(3-trifluoromethyl-1,2,4-oxadiazol-5-yl)pyridine and 2-chloro-6-(3-pentafluoroethyl-1,2,4-oxadiazol-5-yl)pyridine

21

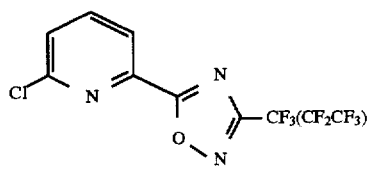

To acetic acid (70 ml) was added 5.0 g of the mixture of trifluoroacetamide O-(6-chloropicolinoyl)oxime and pentafluoropropionamide O-(6-chloropicolinoyl)oxime obtained by the above reaction, and the mixture was refluxed under heating for 1 hour. Acetic acid was removed by evaporation under reduced pressure, chloroform (50 ml) was added to the residue, and the mixture was washed successively with a saturated aqueous sodium hydrogen carbonate solution and a saturated aqueous sodium chloride solution. Thereafter, the mixture was dried over anhydrous magnesium sulfate, and the solvent was removed by evaporation to obtain 4.4 g of a mixture of the desired compounds.

(3) Syntheses of 2-(1-methyl-3-trifluoromethylpyrazol-5-yloxy)-6-(3-trifluoromethyl-1,2,4-oxadiazol-5-yl)pyridine and 2-(1-methyl-3-trifluoromethylpyrazol-5-yloxy)-6-(3-pentafluoroethyl-1,2,4-oxadiazol-5-yl)pyridine

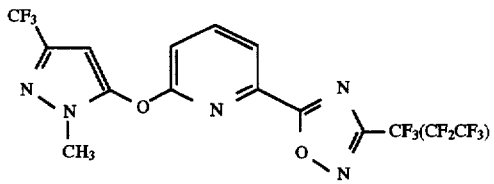

To 15 ml of N,N-dimethylformamide (DMF) were added 1.6 g (5.7 mmol) of the mixture of 2-chloro-6-(3-trifluoromethyl-1,2,4-oxadiazol-5-yl)pyridine and 2-chloro-6-(3-pentafluoroethyl-1,2,4-oxadiazol-5-yl)pyridine obtained by the above reaction, 2.2 g (13 mmol) of 5-hydroxy-1-methyl-3-trifluoromethylpyrazole and 1.8 g (13 mmol) of anhydrous potassium carbonate, and the mixture was stirred under heating at 130° C. for 1.5 hours. After cooling the mixture to room temperature, extraction operation was carried out by adding water (30 ml) and diethyl ether (50 ml). The organic layer obtained was washed successively with water and a saturated aqueous sodium chloride solution and then dried over anhydrous magnesium sulfate, and the solvent was removed by evaporation to obtain an oily product. This oily product was separated and purified by preparative high performance liquid chromatography (ODS column, mobile phase; water/acetonitrile=3/7) to obtain 0.14 g of 2-(1-methyl-3-trifluoromethylpyrazol-5-yloxy)-6-(3-trifluoromethyl-1,2,4-oxadiazol-5-yl)pyridine (melting point: 91° to 93° C.) and 0.49 g of 2-(1-methyl-3-trifluoromethylpyrazol-5-yloxy)-6-(3-pentafluoroethyl-1,2,4-oxadiazol-5-yl)pyridine (melting point: 109° to 110° C.) which were the desired compounds.

Example 2

(1) Synthesis of N'-(6-(3-trifluoromethylphenoxy)picolinoyl)acetohydrazide

22

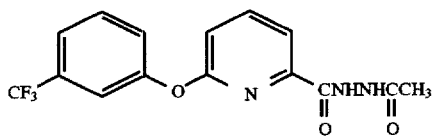

To methylene chloride (10 ml) were added 0.50 g (6.8 mmol) of acetohydrazide and 0.60 g (7.6 mmol) of pyridine, and a methylene chloride (10 ml) solution of 1.5 g (5.7 mmol) of 6-(3-trifluoromethylphenoxy)picolinoyl chloride was added dropwise thereto at 0° to 5° C. After stirring the mixture at room temperature for 1 hour, extraction operation was carried out by adding water (30 ml) and chloroform (50 ml). The organic layer obtained was washed successively with water and a saturated aqueous sodium chloride solution and then dried over anhydrous magnesium sulfate, and the solvent was removed by evaporation to obtain 1.9 g of the desired compound. Melting point: 124° to 125° C.

(2) Synthesis of 2-(5-methyl-1,3,4-oxadiazol-2-yl)-6-(3-trifluoromethylphenoxy)pyridine

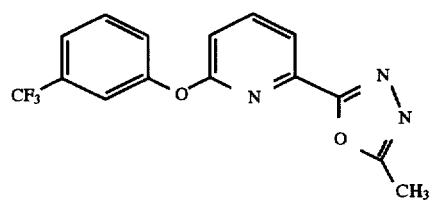

To phosphorus oxychloride (10 ml) was added 1.8 g (5.2 mmol) of N'-(6-(3-trifluoromethylphenoxy)picolinoyl)acetohydrazide, and the mixture was refluxed under heating for 1.5 hours. The mixture was cooled to room temperature and then poured into ice water (50 ml), and extraction operation was carried out by adding diethyl ether (100 ml). The organic layer obtained was washed successively with a saturated aqueous sodium hydrogen carbonate solution and a saturated aqueous sodium chloride solution and then dried over anhydrous magnesium sulfate, and the solvent was removed by evaporation to obtain an oily product. The oily product obtained was purified by silica gel column chromatography (eluent; chloroform) to obtain 0.11 g of the desired compound. Melting point: 79° to 82° C.

Example 3

(1) Synthesis of 6-(3-trifluoromethylphenoxy)pyridine-2-carboxylic acid amide

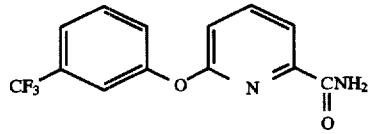

To THF (10 ml) was added 28% aqueous ammonia (4 ml), and a THF (10 ml) solution of 2.0 g (7.4 mmol) of 6-(3-trifluoromethylphenoxy)picolinoyl chloride was added dropwise thereto at 0° to 5° C. After stirring the mixture at room temperature for 3.5 hours, THF was removed by evaporation, and extraction operation was carried out by adding water (30 ml) and ethyl acetate (50 ml). The organic layer obtained was washed with a saturated aqueous sodium chloride solution and then dried over anhydrous magnesium sulfate, and the solvent was removed by evaporation to obtain 1.8 g of the desired compound. Melting point: 129° to 131° C.

(2) Synthesis of $N^2$-(6-(3-trifluoromethylphenoxy)picolinoyl)-$N^1$,$N^1$-dimethylformamidine

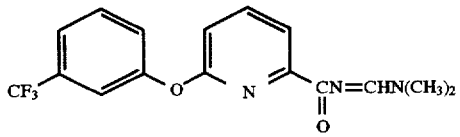

To N,N-dimethylformamide dimethylacetal (10 ml) was added 1.5 g (5.7 mmol) of 6-(3-trifluoromethylphenoxy)pyridine-2-carboxylic acid amide, and the mixture was stirred at 100° C. for 1 hour. The solid obtained by removing the solvent by evaporation under reduced pressure was washed with diisopropyl ether to obtain 1.4 g of the desired compound.

(3) Synthesis of 2-(1-methyl-1,2,4-triazol-5-yl)-6-(3-trifluoromethylphenoxy)pyridine

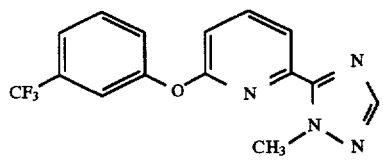

To acetic acid (5 ml) were added 0.12 g (2.6 mmol) of methylhydrazine and 0.5 g (1.5 mmol) of $N^2$-(6-(3-trifluoromethylphenoxy)picolinoyl)-$N^1$,$N^1$-dimethylformamidine, and the mixture was stirred at 90° C. for 1 hour. Acetic acid was removed by evaporation under reduced pressure, and extraction operation was carried out by adding a saturated aqueous sodium hydrogen carbonate solution and diethyl ether. The organic layer obtained was washed with a saturated aqueous sodium chloride solution and then dried over anhydrous magnesium sulfate, the solvent was removed by evaporation, and the solid obtained was washed with diisopropyl ether to obtain 0.29 g of the desired compound. Melting point: 82° to 83° C.

Example 4

(1) Synthesis of 6-(1-methyl-3-trifluoromethylpyrazol-5-yloxy)pyridine-2-carboxylic acid amidoxime

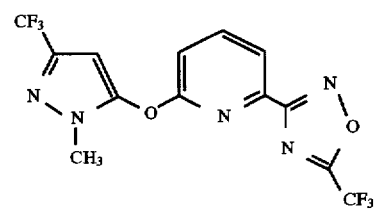

In ethanol (8 ml) was dissolved 0.27 g (3.9 mmol) of hydroxylamine hydrochloride, and 4 ml of an ethanol solution containing 0.27 g (4.0 mmol) of sodium ethoxide was added thereto. After stirring the mixture at room temperature for 0.3 hour, precipitated sodium chloride was filtered off, 1.0 g (3.7 mmol) of 2-cyano-6-(1-methyl-3-trifluoromethylpyrazol-5-yloxy)pyridine was added to the ethanol solution obtained, and the mixture was stirred at room temperature for 1 hour. The solid obtained by removing the solvent by evaporation was washed with a mixed solution of diisopropyl ether/diethyl ether=1/1 to obtain 0.8 g of the desired compound. Melting point: 166° to 168° C.

(2) Synthesis of 2-(1-methyl-3-trifluoromethylpyrazol-5-yloxy)-6-(5-trifluoromethyl-1,2,4-oxadiazol-3-yl)pyridine

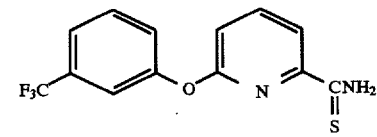

In chloroform (6 ml) were dissolved 0.63 g (2.1 mmol) of 6-(1-methyl-3-trifluoromethylpyrazol-5-yloxy)pyridine-2-carboxylic acid amidoxime and 0.26 g (2.6 mmol) of triethylamine, then, 0.48 g (2.3 mmol) of trifluoroacetic anhydride was added thereto at 5° C., and the mixture was stirred at room temperature for 1 hour. Extraction operation was carried out by adding water (5 ml) and chloroform (10 ml), the organic layer obtained was washed with a saturated aqueous sodium chloride solution and dried over anhydrous magnesium sulfate, and the solvent was removed by evaporation. The solid obtained was washed with a mixed solution of diisopropyl ether/n-hexane=1/1 to obtain 0.4 g of the desired compound. Melting point: 95° to 96° C.

Example 5

(1) Synthesis of 6-(3-trifluoromethylphenoxy)pyridine-2-carboxylic acid thioamide

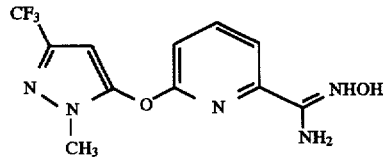

To toluene (8 ml) were added 1.9 g (6.7 mmol) of 6-(3-trifluoromethylphenoxy)pyridine-2-carboxylic acid amide and 1.5 g (3.7 mmol) of a Lawesson reagent, and the mixture was refluxed under heating for 4 hours. The solvent was removed by evaporation under reduced pressure, and the oily product obtained was purified by silica gel column chromatography (eluent; diethyl ether/n-hexane=2/1) to obtain 1.2 g of the desired compound. Melting point: 64° to 66° C.

(2) Synthesis of 2-(4-methylthiazol-2-yl)-6-(3-trifluoromethylphenoxy)pyridine

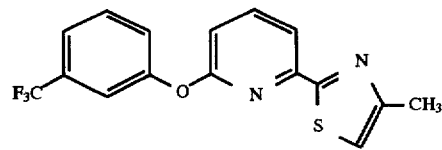

To ethanol (8 ml) were added 0.5 g (1.7 mmol) of 6-(3-trifluoromethylphenoxy)pyridine-2-carboxylic acid thioamide and 0.16 g (1.7 mmol) of chloroacetone, and the mixture was refluxed under heating for 28 hours. The solvent was removed by evaporation under reduced pressure, and extraction operation was carried out by adding water (30 ml) and diethyl ether (50 ml). The organic layer obtained was dried over anhydrous magnesium sulfate and the solid obtained by removing the solvent by evaporation was purified by silica gel column chromatography (eluent; chloroform) to obtain 0.3 g of the desired compound. Melting point: 52° to 54° C.

Example 6

(1) Synthesis of 2-(1H-tetrazol-5-yl)-6-(3-trifluoromethylphenoxy)pyridine

25

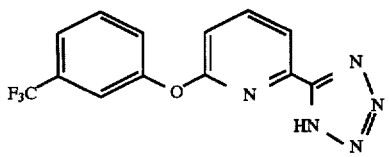

To DMF (18 ml) were added 2.7 g (10 mmol) of 2-cyano-6-(3-trifluoromethylphenoxy)pyridine, 0.89 g (14 mmol) of sodium azide, 0.74 g (14 mmol) of ammonium chloride and 0.04 g of lithium chloride, and the mixture was stirred under heating at 125° C. for 9 hours. After cooling the mixture to room temperature, the solid was filtered off, and under reduced pressure, DMF was removed from the filtrate by evaporation. Water (20 ml) was added to the residue, the mixture was made pH 4 with concentrated hydrochloric acid, and the solid precipitated was collected by filtration, washed with water and dried to obtain 2.7 g of the desired compound. Melting point: 162° to 164° C.

(2) Syntheses of 2-(1-methyl-1H-tetrazol-5-yl)-6-(3-trifluoromethylphenoxy)pyridine and 2-(2-methyl-2H-tetrazol-5-yl)-6-(3-trifluoromethylphenoxy)pyridine

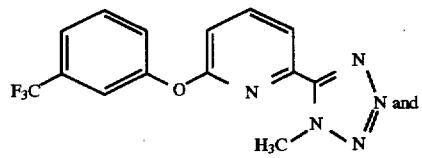

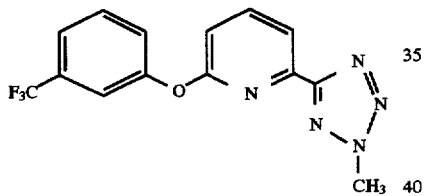

To DMF (4 ml) were added 1.4 g (4.5 mmol) of 2-(1H-tetrazol-5-yl)-6-(3-trifluoromethylphenoxy)pyridine, 0.92 g (6.7 mmol) of potassium carbonate and 0.89 g (6.2 mmol) of methyl iodide, and the mixture was stirred at room temperature for 2 hours. The reaction mixture was poured into water (20 ml), and extraction operation was carried out by adding diethyl ether (30 ml). After washing the organic layer obtained with a saturated aqueous sodium chloride solution, it was dried over anhydrous magnesium sulfate. The solid obtained by removing the solvent by evaporation was washed with a mixed solution of diisopropyl ether/diethyl ether=1/1 to obtain 0.4 g of 2-(1-methyl-1H-tetrazol-5-yl)-6-(3-trifluoromethylphenoxy)pyridine (melting point: 92° to 94° C.) which was the desired compound. Further, the solid obtained by removing the solvent by evaporation from the washing solution was purified by silica gel column chromatography (eluent; chloroform) to obtain 0.4 g of 2-(2-methyl-2H-tetrazol-5-yl)-6-(3-trifluoromethylphenoxy)pyridine (melting point: 58° to 61° C.) which was the desired compound.

Example 7

(1) Synthesis of 6-(3-trifluoromethylphenoxy)picolinohydrazide

26

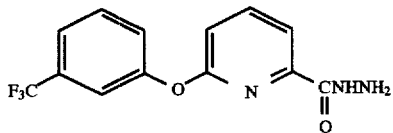

To water (200 ml) were added 20 g (64 mmol) of ethyl 6-(3-trifluoromethylphenoxy)-2-carboxylate and 36 g (720 mmol) of hydrazine hydrate, and the mixture was refluxed under heating for 2 hours. After cooling the mixture to room temperature, the solid precipitated was collected by filtration, washed with diisopropyl ether and dried to obtain 16 g of the desired compound. Melting point: 138° to 140° C.

(2) Synthesis of N'-(6-(3-trifluoromethylphenoxy)picolinoyl)pentafluoropropionohydrazide

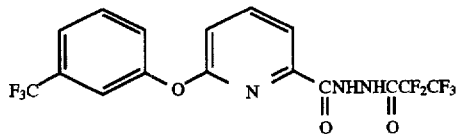

In THF (30 ml) was dissolved 2.0 g (6.7 mmol) of 6-(3-trifluoromethylphenoxy)picolinohydrazide, and a THF (15 ml) solution of 2.1 g (6.7 mmol) of pentafluoropropionic anhydride was added dropwise thereto at room temperature. After stirring the mixture at room temperature for 6 hours, extraction operation was carried out by adding a saturated aqueous sodium hydrogen carbonate solution (30 ml) and ethyl acetate (50 ml). The organic layer obtained was washed with a saturated aqueous sodium chloride solution and then dried over anhydrous magnesium sulfate, and the solvent was removed by evaporation to obtain 3.0 g of the desired compound. Glassy solid.

(3) Synthesis 2-(5-pentafluoroethyl-1,3,4-oxadiazol-2-yl)-6-(3-trifluoromethylphenoxy)pyridine

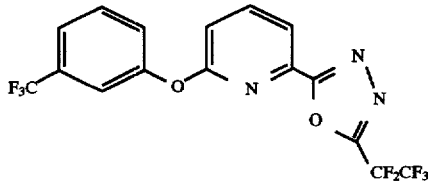

To phosphorous oxychloride (3.5 ml) was added 2.9 g (6.5 mmol) of N'-(6-(3-trifluoromethylphenoxy)picolinoyl)pentafluoropropionohydrazide, and the mixture was stirred under heating at 110° C. for 2.5 hours. Phosphorus oxychloride was removed by evaporation under reduced pressure, and extraction operation was carried out by adding a saturated aqueous sodium hydrogen carbonate solution (30 ml) and ethyl acetate (50 ml). The organic layer obtained was washed with a saturated aqueous sodium chloride solution, and dried over anhydrous magnesium sulfate. The oily product obtained by removing the solvent by evaporation was purified by silica gel column chromatography (eluent; chloroform) to obtain 1.0 g of the desired compound. An oily substance.

Example 8

(1) Synthesis of 2-(1,3,4-oxadiazolin-5-thion-2-yl)-6-(3-trifluoromethylphenoxy)pyridine

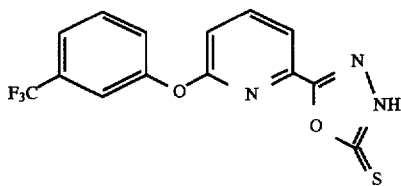

To 95% ethanol (20 ml) were added 2.0 g (6.7 mmol) of 6-(3-trifluoromethylphenoxy)picolinoylhydrazide, 0.6 g (8.1 mmol) of carbon disulfide and 0.4 g (7.1 mmol) of potassium hydroxide, and the mixture was refluxed under heating for 5 hours. Under reduced pressure, ethanol was removed by evaporation, and the residue was dissolved in water (10 ml). The resulting solution was made acidic with concentrated hydrochloric acid, and the solid precipitated was collected by filtration and dried to obtain 2.0 g of the desired compound. Melting point: 141° to 144° C.

(2) Synthesis of 2-(5-methylthio-1,3,4-oxadiazol-2-yl)-6-(3-trifluoromethylphenoxy)pyridine

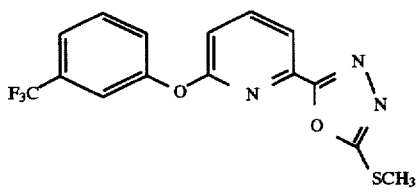

In THF (20 ml) was suspended 0.08 g (3.3 mmol) of sodium hydride (washed with n-hexane), and 1.0 g (3.0 mmol) of 2-(1,3,4-oxadiazolin-5-thion-2-yl)-6-(3-trifluoromethylphenoxy)pyridine and 0.4 g (3.0 mmol) of methyl iodide were added thereto. The mixture was stirred at room temperature for 0.5 hour. Extraction operation was carried out by adding water (50 ml) and ethyl acetate (50 ml). After washing the organic layer obtained with a saturated aqueous sodium chloride solution, it was dried over anhydrous magnesium sulfate and the solvent was removed by evaporation. The oily product obtained was purified by silica gel column chromatography (eluent; chloroform) to obtain 0.8 g of the desired compound. Melting point: 75° to 76° C.

(3) Synthesis of 2-(5-methylsulfonyl-1,3,4-oxadiazol-2-yl)-6-(3-trifluoromethylphenoxy)pyridine

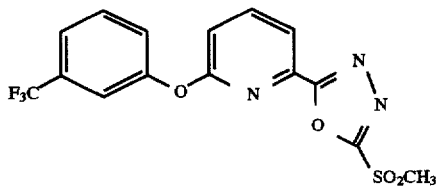

To methylene chloride (10 ml) were added 0.8 g (2.3 mmol) of 2-(5-methylthio-1,3,4-oxadiazol-2-yl)-6-(3-trifluoromethylphenoxy)pyridine and 1.1 g (6.4 mmol) of m-chloroperbenzoic acid, and the mixture was stirred at room temperature for 20 hours. Ethyl acetate (100 ml) was added to the mixture, and the resulting mixture was washed twice with a saturated aqueous sodium hydrogen carbonate solution (50 ml), washed with a 5% aqueous sodium thiosulfate solution (50 ml) and a saturated aqueous sodium chloride solution and then dried over anhydrous magnesium sulfate, and the solvent was removed by evaporation to obtain 0.8 g of the desired compound. An oily product.

(4) Synthesis of 2-(5-(2,2,2-trifluoroethoxy)-1,3,4-oxadiazol-2-yl)-6-(3-trifluoromethylphenoxy)pyridine

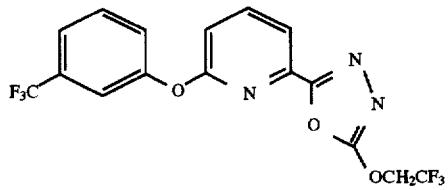

To DMF (5 ml) were added 0.4 g (1.0 mmol) of 2-(5-methylsulfonyl-1,3,4-oxadiazol-2-yl)-6-(3-trifluoromethylphenoxy)pyridine, 0.1 g (1.0 mmol) of 2,2,2-trifluoroethanol and 0.14 g (1.0 mmol) of potassium carbonate, and the mixture was stirred at room temperature for 2 hours. Water (30 ml) was added to the mixture, and extraction operation was carried out twice with diethyl ether (30 ml). After washing the organic layer obtained with a saturated aqueous sodium chloride solution, it was dried over anhydrous magnesium sulfate and the solvent was removed by evaporation. The oily product obtained was purified by silica gel column chromatography (eluent; chloroform) to obtain 0.2 g of the desired compound. Melting point: 65° to 70° C.

Example 9
Synthesis of 2-(5-pentafluoroethyl-1,3,4-thiadiazol-2-yl)-6-(3-trifluoromethylphenoxy)pyridine

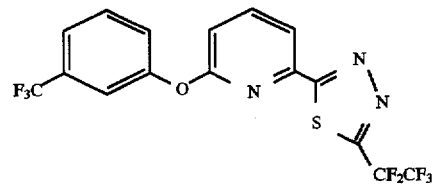

To toluene (30 ml) were added 3.4 g (7.7 mmol) of N'-(6-(3-trifluoromethylphenoxy)picolinoyl) pentafluoropropionohydrazide and 3.1 g (7.7 mmol) of a Lawesson reagent, and the mixture was refluxed under heating for 3 hours. The oily product obtained by removing the solvent by evaporation under reduced pressure was purified by silica gel column chromatography (eluent; n-hexane/diethyl ether=1/2) to obtain 0.9 g of the desired compound. Melting point: 98° to 99° C.

Example 10
(1) Synthesis of N-(1,1-dimethyl-2-hydroxyethyl)-6-chloropicolinic acid amide

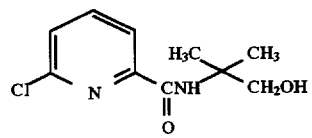

To THF (20 ml) was added 3.0 g (34 mmol) of 2-amino-2-methylpropanol, and a THF (20 ml) solution of 3.0 g (17 mmol) of 6-chloropicolinic acid chloride was added dropwise thereto at 5° C. over 15 minutes. After stirring the mixture at room temperature for 2.5 hours, ethyl acetate (100 ml) was added thereto. The resulting mixture was washed successively with water and a saturated aqueous sodium chloride solution and dried over anhydrous magnesium sulfate, and the solvent was removed by evaporation to obtain 4.1 g of the desired compound. An oily substance.

(2) Synthesis of 6-chloro-2-(4,4-dimethyloxazolin-2-yl)pyridine

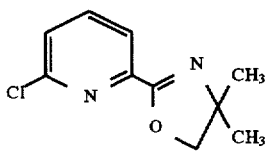

To THF (30 ml) were added 3.2 g (14 mmol) of N-(1,1-dimethyl-2-hydroxyethyl)-6-chloropicolinic acid amide and 1.4 g (14 mmol) of triethylamine, and a THF (10 ml) solution of 1.6 g (14 mmol) of methanesulfonyl chloride was added dropwise thereto at 5° C. over 15 minutes. After stirring the mixture at room temperature for 20 hours, the solid precipitated was filtered off, and the solvent was removed by evaporation. The residue was dissolved in ethyl acetate (50 ml), washed successively with water and a saturated aqueous sodium chloride solution and then dried over anhydrous magnesium sulfate, and the solvent was removed by evaporation to obtain solid. To methanol (80 ml) were added the solid obtained and 1.1 g (20 mmol) of potassium hydroxide, and the mixture was refluxed under heating for 30 minutes. After removing the solvent by evaporation, ethyl acetate (100 ml) was added to the residue, and the mixture was washed successively with water and a saturated aqueous sodium chloride solution and dried over anhydrous magnesium sulfate. The solid obtained by removing the solvent by evaporation was washed with diisopropyl ether and dried to obtain 1.2 g of the desired compound. Melting point: 81° to 83° C.

(3) Synthesis of 2-(4,4-dimethyloxazolin-2-yl)-6-(3-trifluoromethylphenoxy)pyridine

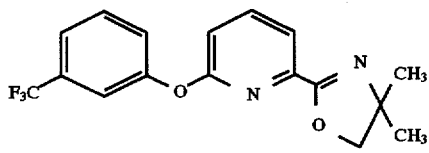

To DMF (10 ml) were added 0.8 g (3.8 mmol) of 6-chloro-2-(4,4-dimethyloxazolin-2-yl)pyridine, 1.3 g (8.0 mmol) of m-trifluoromethylphenol and 1.1 g (8.0 mmol) of potassium carbonate, and the mixture was stirred at 130° C. for 24 hours. After cooling the mixture was room temperature, extraction operation was carried out by adding water (50 ml) and diethyl ether (100 ml). The organic layer obtained was washed with a saturated aqueous sodium chloride solution and then dried over anhydrous magnesium sulfate, and the solvent was removed by evaporation. The oily product obtained was purified by silica gel column chromatography (eluent; chloroform) to obtain 0.6 g of the desired compound. An oily substance.

Example 11

(1) Synthesis of 6-chloropicolinohydrazide

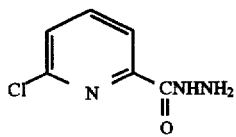

To THF (200 ml) were added 10 g (57 mmol) of 6-chloropicolinic acid chloride and 5.8 g (57 mmol) of triethylamine, and 7.8 g (170 mmol) of ethanol was added dropwise thereto at room temperature. After stirring the mixture at room temperature for 2.5 hours, the solid precipitated was filtered off, and the solvent was removed by evaporation. The residue was dissolved in ethyl acetate (200 ml), washed successively with water and a saturated aqueous sodium chloride solution and then dried over anhydrous magnesium sulfate. The solvent was removed by evaporation to obtain an oily product. To water (115 ml) were added the oily product obtained and 15 g (300 mmol) of hydrazine hydrate, and the mixture was refluxed under heating at 100° C. for 45 minutes. The mixture was cooled to room temperature, and the solid precipitated was collected by filtration, washed with water and dried to obtain 7.8 g of the desired compound. Melting point: 137° to 140° C.

(2) Synthesis of N'-(6-chloropicolinoyl)cyclopropanecarbohydrazide

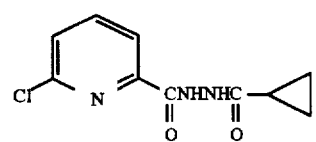

To THF (100 ml) were added 5.0 g (29 mmol) of 6-chloropicolinohydrazide and 2.9 g of (29 mmol) of triethylamine, and 3.0 g (29 mmol) of cyclopropanecarboxylic acid chloride was added dropwise thereto at room temperature. After stirring the mixture at room temperature for 1 hour, the solvent was removed by evaporation under reduced pressure. The residue was dissolved in ethyl acetate (300 ml), washed with a saturated aqueous sodium chloride solution and then dried over anhydrous magnesium sulfate, and the solvent was removed by evaporation to obtain 6.3 g of the desired compound. Melting point: 205° to 207° C.

(3) Synthesis of 6-chloro-2-(5-cyclopropyl-1,3,4-oxadiazol-2-yl)pyridine

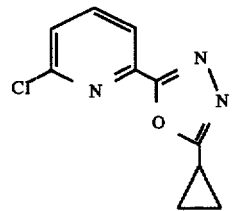

To phosphorus oxychloride (30 ml) was added 4.0 g (17 mmol) of N'-(6-chloropicolinoyl)cyclopropanecarbohydrazide, and the mixture was stirred under heating at 90° C. for 3 hours. Phosphorus oxychloride was removed by evaporation under reduced pressure, and extraction operation was carried out by adding a saturated aqueous sodium hydrogen carbonate solution (30 ml) and ethyl acetate (50 ml). The organic layer obtained was washed with a saturated aqueous sodium chloride solution and then dried over anhydrous magnesium sulfate, and the solvent was removed by evaporation to obtain 3.2 g of the desired compound. Melting point: 74° to 77° C.

(4) Synthesis of 2-(5-cyclopropyl-1,3,4-oxadiazol-2-yl)-6-(3-methylphenoxy)pyridine

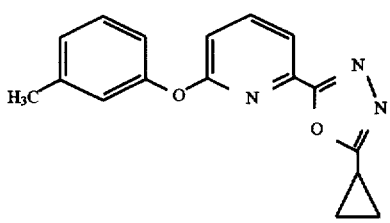

To 3 ml of dimethylsulfoxide (DMSO) were added 0.06 g (1.5 mmol) of 60% sodium hydride and 0.16 g (1.5 mmol) of m-cresol, and the mixture was stirred at room temperature for 10 minutes. A DMSO (5 ml) solution of 0.3 g (1.4 mmol) of 6-chloro-2-(5-cyclopropyl-1,3,4-oxadiazol-2-yl)pyridine was added to the mixture, and the resulting mixture was stirred under heating at 100° C. for 8 hours. After cooling the mixture to room temperature, extraction operation was carried out by adding water (50 ml) and diethyl ether (100 ml). The organic layer obtained was washed successively with water and a saturated aqueous sodium chloride solution and then dried over anhydrous magnesium sulfate, and the solvent was removed by evaporation. The oily product obtained was purified by silica gel column chromatography (eluent; chloroform) to obtain 0.2 g of the desired compound. An oily substance.

Example 12

(1) Synthesis of N'-(6-(3-trifluoromethylphenoxy)picolinoyl)acrylohydrazide

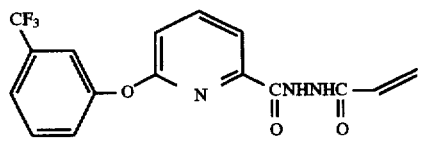

To THF (100 ml) were added 8.1 g (27 mmol) of 6-(3-trifluoromethylphenoxy)picolinohydrazide and 2.8 g (27 mmol) of triethylamine, and then, 2.5 g (27 mmol) of acrylic acid chloride was added dropwise thereto under ice cooling while stirring. The mixture was stirred at room temperature for 0.5 hour. THF was removed from the reaction mixture by evaporation, and ethyl acetate (100 ml) was added to the residue. The mixture was washed successively with a saturated aqueous sodium hydrogen carbonate solution and a saturated aqueous sodium chloride solution and then dried over anhydrous magnesium sulfate, and the solvent was removed by evaporation to obtain 8.6 g of the desired compound. Melting point: 143° to 145° C.

(2) Synthesis of 6-(3-trifluoromethylphenoxy)-2-(5-vinyl-1,3,4-oxadiazol-2-yl)pyridine

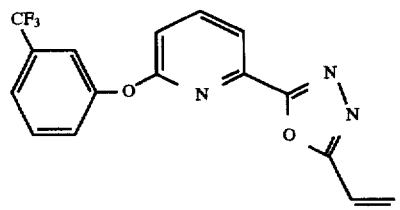

To phosphorus oxychloride (10 ml) was added 1.5 g (4.3 mmol) of N'-(6-(3-trifluoromethylphenoxy)picolinoyl)acrylohydrazide, and the mixture was stirred at 80° C. for 1 hour. After removing phosphorus oxychloride by evaporation, ethyl acetate (50 ml) was added to the residue. The mixture was washed successively with a saturated aqueous sodium hydrogen carbonate solution and a saturated aqueous sodium chloride solution and dried over anhydrous magnesium sulfate. The residue obtained by removing the solvent by evaporation was purified by silica gel column chromatography (eluent; chloroform) to obtain 0.49 g of an oily substance which was a mixture (about 2/8) of the desired compound and 2-(5-(2-chloroethyl)-1,3,4-oxadiazol-2-yl)-6-(3-trifluoromethylphenoxy)pyridine. To DMF (10 ml) were added the above mixture and 0.18 g (1.3 mmol) of potassium carbonate, and the resulting mixture was stirred at 80° C. for 1 hour. After cooling the reaction mixture to room temperature, water (50 ml) was added to the mixture, and the resulting product was extracted with diethyl ether. The diethyl ether layer was washed successively with water and a saturated aqueous sodium chloride solution and dried over anhydrous magnesium sulfate. The residue obtained by removing the solvent by evaporation was washed with a n-hexane/diisopropyl ether (1/1) mixed solution to obtain 0.33 g of the desired compound. Melting point: 94° to 96° C.

(3) Synthesis of 2-(5-(1,2-epoxyethyl)-1,3,4-oxadiazol-2-yl)-6-(3-trifluoromethylphenoxy)pyridine

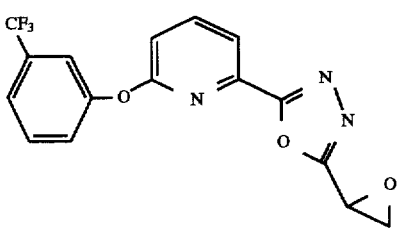

To chloroform (20 ml) were added to 1.1 g (3.3 mmol) of 6-(3-trifluoromethylphenoxy)-2-(5-vinyl-1,3,4-oxadiazol-2-yl)pyridine and 1.1 g (6.4 mmol) of m-chloroperbenzoic acid, and the mixture was refluxed under heating for 48 hours. After completion of the reaction, the reaction mixture was washed successively with a saturated aqueous sodium thiosulfate solution, a saturated aqueous sodium hydrogen carbonate solution and a saturated aqueous sodium chloride solution. The residue obtained by drying the mixture over anhydrous sodium sulfate and removing the solvent by evaporation was purified by silica gel column chromatography (eluent; chloroform) to obtain 0.41 g of the desired compound. Melting point: 53° to 58° C.

Example 13

(1) Synthesis of N'-(6-(3-trifluoromethylphenoxy)picolinoyl)ethyloxalohydrazide

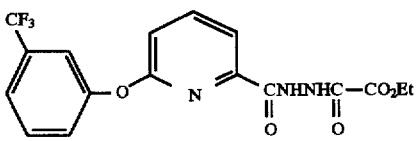

To THF (70 ml) were added 5.0 g (17 mmol) of 6-(3-trifluoromethylphenoxy)picolinohydrazide and 1.7 g (17 mmol) of triethylamine, and then, 2.3 g (17 mmol) of ethyloxalyl chloride was added dropwise thereto under ice cooling while stirring, and the mixture was stirred at room temperature for 0.5 hour. THF was removed from the reaction mixture by evaporation, and ethyl acetate (100 ml) was added to the residue. The mixture was washed successively with a saturated aqueous sodium hydrogen carbonate solution and a saturated aqueous sodium chloride solution and then dried over anhydrous magnesium sulfate, and the solvent was removed by evaporation to obtain 6.9 g of the desired compound. A resinous substance.

(2) Synthesis of 2-(5-ethoxycarbonyl-1,3,4-oxadiazol-2-yl)-6-(3-trifluoromethylphenoxy)pyridine

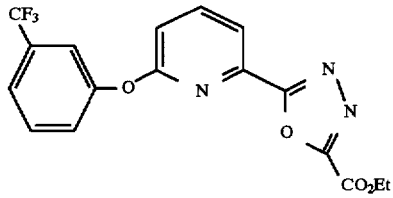

To toluene (40 ml) were added 6.9 g (17 mmol) of N'-(6-(3-trifluoromethylphenoxy)picolinoyl)ethyloxalohydrazide and 2.7 g (17 mmol) of phosphorus oxychloride, and the mixture was refluxed for 4 hours. After removing the solvent by evaporation, ethyl acetate (50 ml) was added to the residue, and the mixture was washed successively with a saturated aqueous sodium hydrogen carbonate solution and a saturated aqueous sodium chloride solution, and dried over anhydrous magnesium sulfate. The residue obtained by removing the solvent by evaporation was purified by silica gel column chromatography (eluent; chloroform) to obtain 3.6 g of the desired compound. An oily substance.

(3) Synthesis of 2-(5-carbamoyl-1,3,4-oxadiazol-2-yl)-6-(3-trifluoromethylphenoxy)pyridine

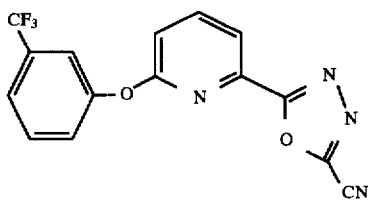

To THF (5 ml) were added 0.5 g (1.4 mmol) of 2-(5-carbamoyl-1,3,4-oxadiazol-2-yl)-6-(3-trifluoromethylphenoxy)pyridine and 0.23 g (2.9 mmol) of pyridine, and then, 0.33 g (1.6 mmol) of trifluoroacetic anhydride was added dropwise thereto under ice cooling. After the mixture was stirred at room temperature for 0.5 hour, water (10 ml) was added to the mixture, and the resulting product was extracted with diethyl ether. The diethyl ether layer was washed successively with diluted hydrochloric acid, a saturated aqueous sodium hydrogen carbonate solution and a saturated aqueous sodium chloride solution, and dried over anhydrous magnesium sulfate. The residue obtained by removing the solvent by evaporation was purified by silica gel column chromatography (eluent; chloroform) to obtain 0.42 g of the desired compound. An oily substance.

Example 14

Synthesis of 2-(1,3,4-oxadiazolin-5-on-2-yl)-6-(3-trifluoromethylphenoxy)pyridine

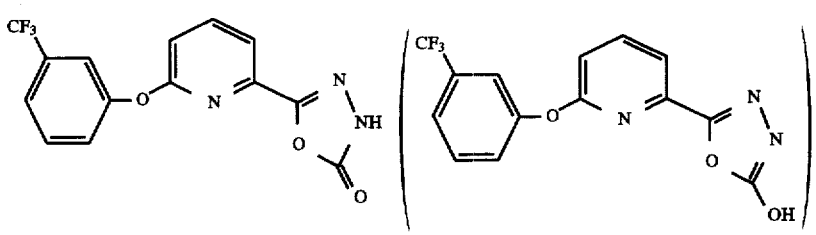

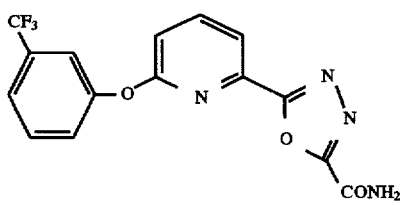

To ethanol (10 ml) were added 1.5 g (4.0 mmol) of 2-(5-ethoxycarbonyl-1,3,4-oxadiazol-2-yl)-6-(3-trifluoromethylphenoxy)pyridine, 28% aqueous ammonia (3 ml) and 0.05 g (0.09 mmol) of ammonium chloride, and the mixture was stirred at room temperature for 0.5 hour. After removing the solvent by evaporation, ethyl acetate (50 ml) was added to the residue, the mixture was washed successively with water and a saturated aqueous sodium chloride solution and dried over anhydrous magnesium sulfate, and the solvent was removed by evaporation to obtain 1.3 g of the desired compound. Melting point: 136° to 138° C.

(4) Synthesis of 2-(5-cyano-1,3,4-oxadiazol-2-yl)-6-(3-trifluoromethylphenoxy)pyridine In water (5 ml) was dissolved 0.15 g (3.8 mmol) of sodium hydroxide, and 1.0 g (2.9 mmol) of 2-(1,3,4-oxadiazolin-5-thion-2-yl)-6-(3-trifluoromethylphenoxy)pyridine, ethanol (10 ml) and 0.38 g (0.39 mmol) of cyclohexene oxide were added to the solution, and the mixture was stirred under heating at 40° to 45° C. for 20 hours. After removing the solvent by evaporation, the residue was dissolved in water (20 ml) and washed with diethyl ether. The aqueous layer was adjusted to pH 2 with 35% hydrochloric acid, and the solid precipitated was extracted with ethyl acetate. The ethyl acetate layer was dried over anhydrous magnesium sulfate and the solvent was removed by evaporation. The residue obtained was purified by silica gel column chromatography (eluent; chloroform) to obtain 0.68 g of the desired compound. Melting point: 139° to 141° C.

The structural formulae and physical property values of compounds synthesized by using the same methods as in Examples described above are shown in Table 1 together with those of Examples described above. The symbols in the table each represent the following meanings.

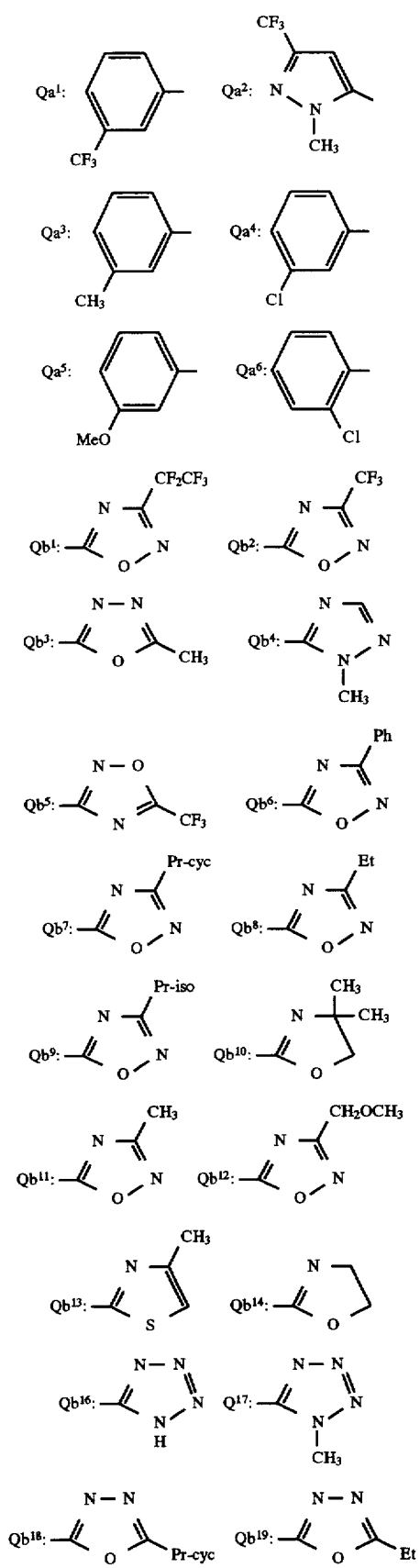
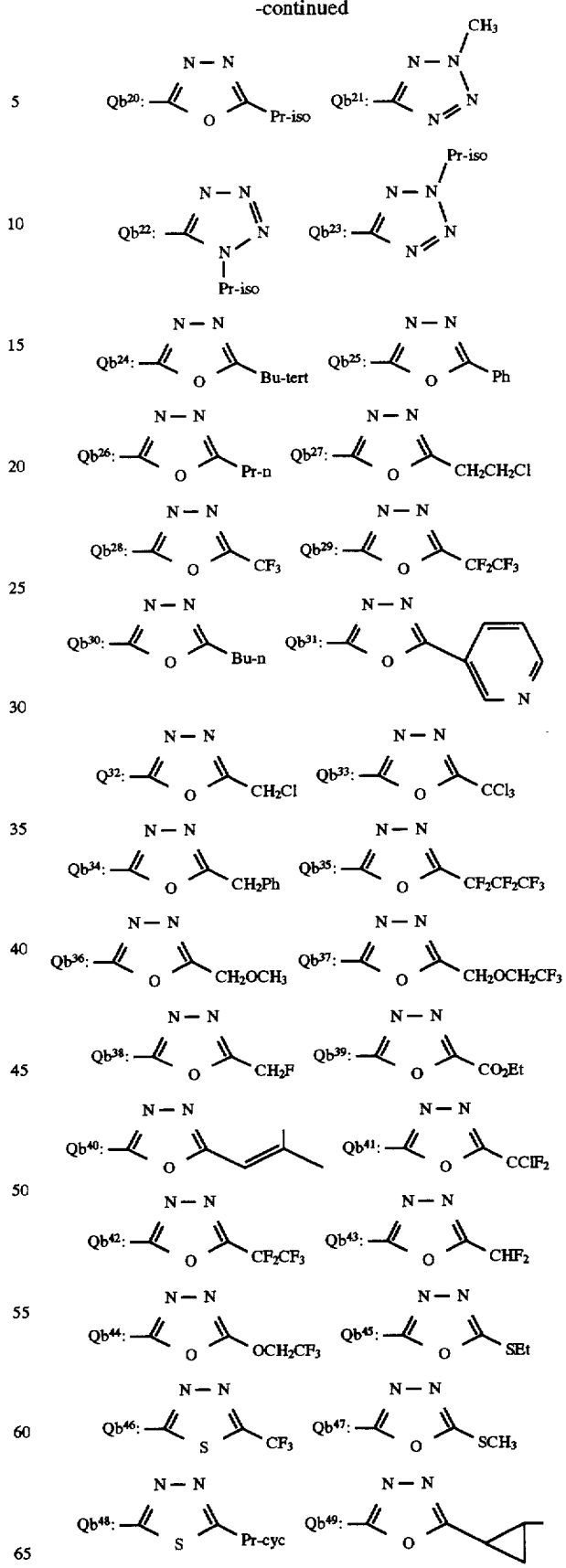

-continued

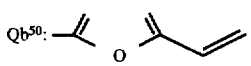

TABLE 1

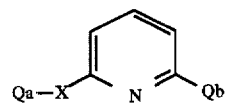

| No. | Qa | X | Qb | Physical property value (melting point, °C.) |
|---|---|---|---|---|
| 1 | $Qa^1$ | O | $Qb^1$ | Oily substance |
| 2 | $Qa^1$ | O | $Qb^2$ | 42 to 44 |
| 3 | $Qa^2$ | O | $Qb^1$ | 109 to 110 |
| 4 | $Qa^1$ | O | $Qb^3$ | 79 to 82 |
| 5 | $Qa^1$ | O | $Qb^4$ | 82 to 83 |
| 6 | $Qa^2$ | O | $Qb^5$ | 95 to 96 |
| 7 | $Qa^2$ | O | $Qb^2$ | 91 to 93 |
| 8 | $Qa^1$ | O | $Qb^6$ | 121 to 123 |
| 9 | $Qa^2$ | O | $Qb^6$ | 140 to 142 |
| 10 | $Qa^1$ | O | $Qb^7$ | 140 to 144 |
| 11 | $Qa^1$ | O | $Qb^8$ | Oily substance |
| 12 | $Qa^1$ | O | $Qb^9$ | 62 to 66 |
| 13 | $Qa^1$ | O | $Qb^{10}$ | Oily substance |
| 14 | $Qa^1$ | O | $Qb^{11}$ | 76 to 79 |
| 15 | $Qa^1$ | O | $Qb^{12}$ | Oily substance |
| 16 | $Qa^1$ | O | $Qb^{13}$ | 52 to 54 |
| 17 | $Qa^1$ | O | $Qb^{14}$ | 57 to 60 |
| 18 | $Qa^2$ | O | $Qb^3$ | 117 to 121 |
| 19 | $Qa^1$ | O | $Qb^{16}$ | 162 to 164 |
| 20 | $Qa^1$ | O | $Qb^{17}$ | 92 to 94 |
| 21 | $Qa^1$ | O | $Qb^{18}$ | 79 to 81 |
| 22 | $Qa^1$ | O | $Qb^{19}$ | 64 to 67 |
| 23 | $Qa^1$ | O | $Qb^{20}$ | Oily substance |
| 24 | $Qa^1$ | O | $Qb^{21}$ | 58 to 61 |
| 25 | $Qa^1$ | O | $Qb^{22}$ | 63 to 64 |
| 26 | $Qa^1$ | O | $Qb^{23}$ | 59 to 60 |
| 27 | $Qa^1$ | O | $Qb^{24}$ | Oily substance |
| 28 | $Qa^2$ | O | $Qb^{19}$ | 95 to 97 |
| 29 | $Qa^1$ | O | $Qb^{25}$ | 113 to 117 |
| 30 | $Qa^1$ | O | $Qb^{26}$ | 30 to 35 |
| 31 | $Qa^1$ | O | $Qb^{27}$ | Oily substance |
| 32 | $Qa^1$ | O | $Qb^{28}$ | 39 to 42 |
| 33 | $Qa^1$ | O | $Qb^{29}$ | Oily substance |
| 34 | $Qa^1$ | O | $Qb^{30}$ | Oily substance |
| 35 | $Qa^2$ | O | $Qb^{29}$ | 136 to 138 |
| 36 | $Qa^1$ | O | $Qb^{31}$ | 73 to 78 |
| 37 | $Qa^1$ | O | $Qb^{32}$ | 73 to 75 |
| 38 | $Qa^1$ | O | $Qb^{33}$ | Oily substance |
| 39 | $Qa^1$ | O | $Qb^{34}$ | 105 to 109 |
| 40 | $Qa^1$ | O | $Qb^{35}$ | Oily substance |
| 41 | $Qa^1$ | O | $Qb^{36}$ | 55 to 60 |
| 42 | $Qa^1$ | O | $Qb^{37}$ | Oily substance |

TABLE 1-continued

| No. | Qa | X | Qb | Physical property value (melting point, °C.) |
|---|---|---|---|---|
| 43 | $Qa^1$ | O | $Qb^{38}$ | 32 to 35 |
| 44 | $Qa^1$ | O | $Qb^{39}$ | Oily substance |
| 45 | $Qa^1$ | O | $Qb^{40}$ | 87 to 90 |
| 46 | $Qa^2$ | O | $Qb^{28}$ | 129 to 130 |
| 47 | $Qa^1$ | O | $Qb^{41}$ | Oily substance |
| 48 | $Qa^1$ | O | $Qb^{42}$ | 98 to 99 |
| 49 | $Qa^1$ | O | $Qb^{43}$ | 70 to 72 |
| 50 | $Qa^1$ | O | $Qb^{44}$ | 65 to 70 |
| 51 | $Qa^1$ | O | $Qb^{45}$ | 53 to 54 |
| 52 | $Qa^1$ | O | $Qb^{46}$ | 99 to 100 |
| 53 | $Qa^3$ | O | $Qb^{18}$ | Oily substance |
| 54 | $Qa^1$ | O | $Qb^{47}$ | 75 to 76 |
| 55 | $Qa^1$ | O | $Qb^{48}$ | Oily substance |
| 56 | $Qa^4$ | O | $Qb^{18}$ | Oily substance |
| 57 | $Qa^1$ | O | $Qb^{49}$ | Oily substance |
| 58 | $Qa^5$ | O | $Qb^{18}$ | Oily substance |
| 59 | $Qa^6$ | O | $Qb^{18}$ | Oily substance |
| 60 | $Qa^2$ | O | $Qb^{18}$ | 84 to 88 |
| 61 | $Qa^1$ | O | $Qb^{50}$ | 94 to 96 |
| 62 | $Qa^1$ | O | $Qb^{51}$ | 77 to 79 |
| 63 | $Qa^1$ | O | $Qb^{52}$ | Oily substance |
| 64 | $Qa^1$ | O | $Qb^{53}$ | 136 to 138 |
| 65 | $Qa^1$ | O | $Qb^{54}$ | 98 to 102 |
| 66 | $Qa^2$ | O | $Qb^{48}$ | 94 to 97 |
| 67 | $Qa^1$ | O | $Qb^{55}$ | 139 to 141 |
| 68 | $Qa^1$ | O | $Qb^{56}$ | 43 to 46 |
| 69 | $Qa^1$ | O | $Qb^{57}$ | 65 to 67 |
| 70 | $Qa^1$ | O | $Qb^{58}$ | 53 to 58 |
| 71 | $Qa^7$ | O | $Qb^{18}$ | Oily substance |

Next, examples of the compound included in the present invention are shown in the following Table 2 to Table 6 together with the compounds synthesized in Examples described above, but the compound of the present invention is not limited by these. The symbols in the tables each represent the following meanings.

Me: a methyl group, Et: an ethyl group, Pr-n: a normal propyl group, Pr-iso: an isopropyl group, Bu-n: a normal butyl group, Bu-iso: an isobutyl group, Bu-sec: a secondary butyl group, Bu-tert: a tertiary butyl group, Pen-n: a normal pentyl group, Hex-n: a normal hexyl group, Pr-cyc: a cyclopropyl group, Bu-cyc: a cyclobutyl group, Pen-cyc: a cyclopentyl group, Hex-cyc: a cyclohexyl group, Ph: a phenyl group, Py: a pyridyl group and Epo: an epoxy group.

TABLE 2

| Qa | X | Y | q |
|---|---|---|---|
| 2-CF$_3$—Ph | O | O | CF$_3$ |
| 3-CF$_3$—Ph | O | O | CF$_3$ |
| 4-CF$_3$—Ph | O | O | CF$_3$ |
| 2-Me—Ph | O | O | CF$_3$ |
| 3-Me—Ph | O | O | CF$_3$ |
| 4-Me—Ph | O | O | CF$_3$ |
| 2-Et—Ph | O | O | CF$_3$ |
| 3-Et—Ph | O | O | CF$_3$ |
| 4-Et—Ph | O | O | CF$_3$ |
| 2-MeO—Ph | O | O | CF$_3$ |
| 3-MeO—Ph | O | O | CF$_3$ |
| 4-MeO—Ph | O | O | CF$_3$ |
| 2-CN—Ph | O | O | CF$_3$ |
| 3-CN—Ph | O | O | CF$_3$ |
| 4-CN—Ph | O | O | CF$_3$ |
| 2-NO$_2$—Ph | O | O | CF$_3$ |
| 3-NO$_2$—Ph | O | O | CF$_3$ |
| 4-NO$_2$—Ph | O | O | CF$_3$ |
| 2-F—Ph | O | O | CF$_3$ |
| 3-F—Ph | O | O | CF$_3$ |
| 4-F—Ph | O | O | CF$_3$ |
| 2-Cl—Ph | O | O | CF$_3$ |
| 3-Cl—Ph | O | O | CF$_3$ |
| 4-Cl—Ph | O | O | CF$_3$ |
| 2-Br—Ph | O | O | CF$_3$ |
| 3-Br—Ph | O | O | CF$_3$ |
| 4-Br—Ph | O | O | CF$_3$ |
| 2-I—Ph | O | O | CF$_3$ |
| 3-I—Ph | O | O | CF$_3$ |
| 4-I—Ph | O | O | CF$_3$ |
| 2-CF$_3$—Ph | O | O | CF$_2$CF$_3$ |
| 3-CF$_3$—Ph | O | O | CF$_2$CF$_3$ |
| 4-CF$_3$—Ph | O | O | CF$_2$CF$_3$ |
| 2-Me—Ph | O | O | CF$_2$CF$_3$ |
| 3-Me—Ph | O | O | CF$_2$CF$_3$ |
| 4-Me—Ph | O | O | CF$_2$CF$_3$ |
| 2-Et—Ph | O | O | CF$_2$CF$_3$ |
| 3-Et—Ph | O | O | CF$_2$CF$_3$ |
| 4-Et—Ph | O | O | CF$_2$CF$_3$ |
| 2-CN—Ph | O | O | CF$_2$CF$_3$ |
| 3-CN—Ph | O | O | CF$_2$CF$_3$ |
| 4-CN—Ph | O | O | CF$_2$CF$_3$ |
| 2-F—Ph | O | O | CF$_2$CF$_3$ |
| 3-F—Ph | O | O | CF$_2$CF$_3$ |
| 4-F—Ph | O | O | CF$_2$CF$_3$ |
| 2-Cl—Ph | O | O | CF$_2$CF$_3$ |
| 3-Cl—Ph | O | O | CF$_2$CF$_3$ |
| 4-Cl—Ph | O | O | CF$_2$CF$_3$ |
| 2-Br—Ph | O | O | CF$_2$CF$_3$ |
| 3-Br—Ph | O | O | CF$_2$CF$_3$ |
| 4-Br—Ph | O | O | CF$_2$CF$_3$ |
| 2-CF$_3$—Ph | O | O | H |
| 3-CF$_3$—Ph | O | O | H |
| 4-CF$_3$—Ph | O | O | H |
| 2-Me—Ph | O | O | H |
| 3-Me—Ph | O | O | H |
| 4-Me—Ph | O | O | H |

TABLE 2-continued

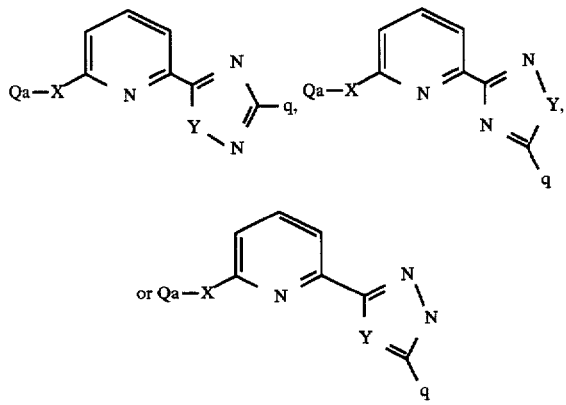

| Qa | X | Y | q |
|---|---|---|---|
| 2-Et—Ph | O | O | H |
| 3-Et—Ph | O | O | H |
| 4-Et—Ph | O | O | H |
| 2-CN—Ph | O | O | H |
| 3-CN—Ph | O | O | H |
| 4-CN—Ph | O | O | H |
| 2-F—Ph | O | O | H |
| 3-F—Ph | O | O | H |
| 4-F—Ph | O | O | H |
| 2-Cl—Ph | O | O | H |
| 3-Cl—Ph | O | O | H |
| 4-Cl—Ph | O | O | H |
| 2-CF$_3$—Ph | O | O | Me |
| 3-CF$_3$—Ph | O | O | Me |
| 4-CF$_3$—Ph | O | O | Me |
| 2-Me—Ph | O | O | Me |
| 3-Me—Ph | O | O | Me |
| 4-Me—Ph | O | O | Me |
| 2-Et—Ph | O | O | Me |
| 3-Et—Ph | O | O | Me |
| 4-Et—Ph | O | O | Me |
| 2-CN—Ph | O | O | Me |
| 3-CN—Ph | O | O | Me |
| 4-CN—Ph | O | O | Me |
| 2-F—Ph | O | O | Me |
| 3-F—Ph | O | O | Me |
| 4-F—Ph | O | O | Me |
| 2-Cl—Ph | O | O | Me |
| 3-Cl—Ph | O | O | Me |
| 4-Cl—Ph | O | O | Me |
| 2-CF$_3$—Ph | O | O | Et |
| 3-CF$_3$—Ph | O | O | Et |
| 4-CF$_3$—Ph | O | O | Et |
| 2-Me—Ph | O | O | Et |
| 3-Me—Ph | O | O | Et |
| 4-Me—Ph | O | O | Et |
| 2-Et—Ph | O | O | Et |
| 3-Et—Ph | O | O | Et |
| 4-Et—Ph | O | O | Et |
| 2-CN—Ph | O | O | Et |
| 3-CN—Ph | O | O | Et |
| 4-CN—Ph | O | O | Et |
| 2-F—Ph | O | O | Et |
| 3-F—Ph | O | O | Et |
| 4-F—Ph | O | O | Et |
| 2-Cl—Ph | O | O | Et |
| 3-Cl—Ph | O | O | Et |
| 4-Cl—Ph | O | O | Et |
| 2-CF$_3$—Ph | O | O | Pr-iso |
| 3-CF$_3$—Ph | O | O | Pr-iso |
| 4-CF$_3$—Ph | O | O | Pr-iso |
| 2-CF$_3$—Ph | O | O | Pr-n |
| 3-CF$_3$—Ph | O | O | Pr-n |
| 4-CF$_3$—Ph | O | O | Pr-n |
| 3-CF$_3$—Ph | O | O | Bu-n |
| 3-CF$_3$—Ph | O | O | Bu-iso |
| 3-CF$_3$—Ph | O | O | Bu-sec |

TABLE 2-continued

| Qa | X | Y | q |
|---|---|---|---|
| 3-CF$_3$—Ph | O | O | Bu-tert |
| 3-CF$_3$—Ph | O | O | Pr-n |
| 3-CF$_3$—Ph | O | O | Pen-n |
| 3-CF$_3$—Ph | O | O | Hex-n |
| 3-CF$_3$—Ph | O | O | Pr-cyc |
| 3-CF$_3$—Ph | O | O | Bu-cyc |
| 3-CF$_3$—Ph | O | O | Pen-cyc |
| 3-CF$_3$—Ph | O | O | Hex-cyc |
| 3-CF$_3$—Ph | O | O | CH$_2$F |
| 3-CF$_3$—Ph | O | O | CH$_2$Cl |
| 3-CF$_3$—Ph | O | O | CH$_2$Br |
| 3-CF$_3$—Ph | O | O | CH$_2$I |
| 3-CF$_3$—Ph | O | O | CHF$_2$ |
| 3-CF$_3$—Ph | O | O | CHCl$_2$ |
| 3-CF$_3$—Ph | O | O | CHBr$_2$ |
| 3-CF$_3$—Ph | O | O | CCl$_3$ |
| 3-CF$_3$—Ph | O | O | CBr$_3$ |
| 3-CF$_3$—Ph | O | O | CClF$_2$ |
| 3-CF$_3$—Ph | O | O | CH$_2$CF$_3$ |
| 3-CF$_3$—Ph | O | O | CH$_2$CH$_2$Cl |
| 3-CF$_3$—Ph | O | O | CH$_2$CHCl$_2$ |
| 3-CF$_3$—Ph | O | O | CH$_2$CCl$_3$ |
| 3-CF$_3$—Ph | O | O | CH$_2$CH$_2$Br |
| 3-CF$_3$—Ph | O | O | CH$_2$CHBr$_2$ |
| 3-CF$_3$—Ph | O | O | CH$_2$CH$_2$I |
| 3-CF$_3$—Ph | O | O | CH$_2$CH$_2$CF$_3$ |
| 3-CF$_3$—Ph | O | O | CH$_2$CF$_2$CF$_3$ |
| 3-CF$_3$—Ph | O | O | CF$_2$CF$_2$CF$_3$ |
| 3-CF$_3$—Ph | O | O | CH$_2$CH$_2$CH$_2$CF$_3$ |
| 3-CF$_3$—Ph | O | O | CH$_2$CH$_2$CF$_2$CF$_3$ |
| 3-CF$_3$—Ph | O | O | CH$_2$CF$_2$CF$_2$CF$_3$ |
| 3-CF$_3$—Ph | O | O | CH$_2$CH$_2$CH$_2$Cl |
| 3-CF$_3$—Ph | O | O | CH$_2$CH$_2$CH$_2$CH$_2$Cl |
| 3-CF$_3$—Ph | O | O | OMe |
| 3-CF$_3$—Ph | O | O | OEt |
| 3-CF$_3$—Ph | O | O | OPr-n |
| 3-CF$_3$—Ph | O | O | OPr-iso |
| 3-CF$_3$—Ph | O | O | OBu-n |
| 3-CF$_3$—Ph | O | O | OBu-iso |
| 3-CF$_3$—Ph | O | O | OBu-tert |
| 3-CF$_3$—Ph | O | O | CN |
| 3-CF$_3$—Ph | O | O | NO$_2$ |
| 3-CF$_3$—Ph | O | O | F |
| 3-CF$_3$—Ph | O | O | Cl |
| 3-CF$_3$—Ph | O | O | Br |
| 3-CF$_3$—Ph | O | O | I |
| 1-Me-3-CF$_3$-pyrazol-5-yl | O | O | CF$_3$ |
| 1-Me-3-CF$_3$CF$_2$-pyrazol-5-yl | O | O | CF$_3$ |
| 1-Me-3-CF$_3$CF$_2$CF$_2$-pyrazol-5-yl | O | O | CF$_3$ |
| 1-Me-pyrazol-5-yl | O | O | CF$_3$ |
| 1-Me-3-Me-pyrazol-5-yl | O | O | CF$_3$ |
| 1-Me-3-Et-pyrazol-5-yl | O | O | CF$_3$ |
| 1-Me-3-Pr-n-pyrazol-5-yl | O | O | CF$_3$ |
| 1-Me-3-CH$_2$F-pyrazol-5-yl | O | O | CF$_3$ |
| 1-Me-3-CHF$_2$-pyrazol-5-yl | O | O | CF$_3$ |
| 1-Me-3-CO$_2$Me-pyrazol-5-yl | O | O | CF$_3$ |
| 1-Me-3-CN-pyrazol-5-yl | O | O | CF$_3$ |

TABLE 2-continued

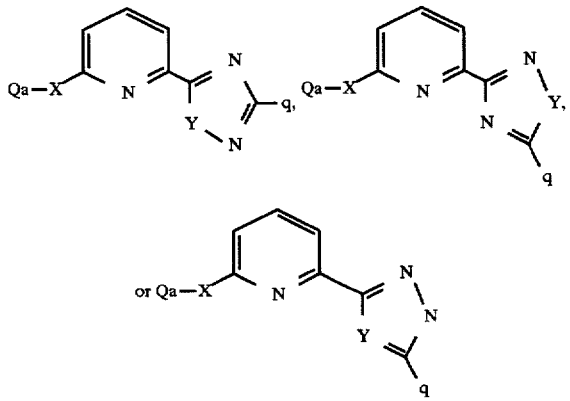

| Qa | X | Y | q |
|---|---|---|---|
| 1-Me-3-NO$_2$-pyrazol-5-yl | O | O | CF$_3$ |
| 1-Me-3-F-pyrazol-5-yl | O | O | CF$_3$ |
| 1-Me-3-Cl-pyrazol-5-yl | O | O | CF$_3$ |
| 1-Me-3-Br-pyrazol-5-yl | O | O | CF$_3$ |
| 1-Me-3-I-pyrazol-5-yl | O | O | CF$_3$ |
| 1-Me-3-CF$_3$-4-Cl-pyrazol-5-yl | O | O | CF$_3$ |
| 1-Me-3-CF$_3$-4-Br-pyrazol-5-yl | O | O | CF$_3$ |
| 1-Et-3-CF$_3$-pyrazol-5-yl | O | O | CF$_3$ |
| 1-Et-3-CF$_3$CF$_2$-pyrazol-5-yl | O | O | CF$_3$ |
| 1-Et-3-CF$_3$CF$_2$CF$_2$-pyrazol-5-yl | O | O | CF$_3$ |
| 1-Et-pyrazol-5-yl | O | O | CF$_3$ |
| 1-Et-3-Me-pyrazol-5-yl | O | O | CF$_3$ |
| 1-Et-3-Et-pyrazol-5-yl | O | O | CF$_3$ |
| 1-Et-3-Pr-n-pyrazol-5-yl | O | O | CF$_3$ |
| 1-Et-3-CH$_2$F-pyrazol-5-yl | O | O | CF$_3$ |
| 1-Et-3-CHF$_2$-pyrazol-5-yl | O | O | CF$_3$ |
| 1-Et-3-CO$_2$Me-pyrazol-5-yl | O | O | CF$_3$ |
| 1-Et-3-CN-pyrazol-5-yl | O | O | CF$_3$ |
| 1-Et-3-NO$_2$-pyrazol-5-yl | O | O | CF$_3$ |
| 1-Et-3-F-pyrazol-5-yl | O | O | CF$_3$ |
| 1-Et-3-Cl-pyrazol-5-yl | O | O | CF$_3$ |
| 1-Et-3-Br-pyrazol-5-yl | O | O | CF$_3$ |
| 1-Et-3-I-pyrazol-5-yl | O | O | CF$_3$ |
| 1-Et-3-CF$_3$-4-Cl-pyrazol-5-yl | O | O | CF$_3$ |
| 1-Et-3-CF$_3$-4-Br-pyrazol-5-yl | O | O | CF$_3$ |
| 1-Me-5-CF$_3$-pyrazol-3-yl | O | O | CF$_3$ |
| 1-Me-5-CF$_3$CF$_2$-pyrazol-3-yl | O | O | CF$_3$ |
| 1-Me-5-CF$_3$CF$_2$CF$_2$-pyrazol-3-yl | O | O | CF$_3$ |
| 1-Me-pyrazol-3-yl | O | O | CF$_3$ |
| 1-Me-5-Me-pyrazol-3-yl | O | O | CF$_3$ |
| 1-Me-5-Et-pyrazol-3-yl | O | O | CF$_3$ |
| 1-Me-5-Pr-n-pyrazol-3-yl | O | O | CF$_3$ |
| 1-Me-5-CH$_2$F-pyrazol-3-yl | O | O | CF$_3$ |
| 1-Me-5-CHF$_2$-pyrazol-3-yl | O | O | CF$_3$ |
| 1-Me-5-CO$_2$Me-pyrazol-3-yl | O | O | CF$_3$ |
| 1-Me-5-CN-pyrazol-3-yl | O | O | CF$_3$ |
| 1-Me-5-NO$_2$-pyrazol-3-yl | O | O | CF$_3$ |
| 1-Me-5-F-pyrazol-3-yl | O | O | CF$_3$ |
| 1-Me-5-Cl-pyrazol-3-yl | O | O | CF$_3$ |
| 1-Me-5-Br-pyrazol-3-yl | O | O | CF$_3$ |
| 1-Me-5-I-pyrazol-3-yl | O | O | CF$_3$ |
| 1-Me-5-CF$_3$-4-Cl-pyrazol-3-yl | O | O | CF$_3$ |
| 1-Me-5-CF$_3$-4-Br-pyrazol-3-yl | O | O | CF$_3$ |
| 1-Me-3-CF$_3$-pyrazol-5-yl | O | O | CF$_2$CF$_3$ |
| 1-Me-3-CF$_3$CF$_2$-pyrazol-5-yl | O | O | CF$_2$CF$_3$ |
| 1-Me-3-CF$_3$CF$_2$CF$_2$-pyrazol-5-yl | O | O | CF$_2$CF$_3$ |
| 1-Me-pyrazol-5-yl | O | O | CF$_2$CF$_3$ |
| 1-Me-3-Me-pyrazol-5-yl | O | O | CF$_2$CF$_3$ |
| 1-Me-3-Et-pyrazol-5-yl | O | O | CF$_2$CF$_3$ |
| 1-Me-3-Pr-n-pyrazol-5-yl | O | O | CF$_2$CF$_3$ |
| 1-Me-3-CH$_2$F-pyrazol-5-yl | O | O | CF$_2$CF$_3$ |
| 1-Me-3-CHF$_2$-pyrazol-5-yl | O | O | CF$_2$CF$_3$ |
| 1-Me-3-CO$_2$Me-pyrazol-5-yl | O | O | CF$_2$CF$_3$ |
| 1-Me-3-CN-pyrazol-5-yl | O | O | CF$_2$CF$_3$ |
| 1-Me-3-NO$_2$-pyrazol-5-yl | O | O | CF$_2$CF$_3$ |
| 1-Me-3-F-pyrazol-5-yl | O | O | CF$_2$CF$_3$ |
| 1-Me-3-Cl-pyrazol-5-yl | O | O | CF$_2$CF$_3$ |

TABLE 2-continued

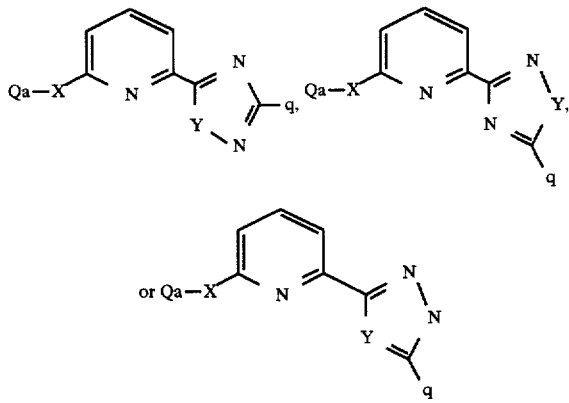

| Qa | X | Y | q |
|---|---|---|---|
| 1-Me-3-Br-pyrazol-5-yl | O | O | $CF_2CF_3$ |
| 1-Me-3-I-pyrazol-5-yl | O | O | $CF_2CF_3$ |
| 1-Me-3-$CF_3$-4-Cl-pyrazol-5-yl | O | O | $CF_2CF_3$ |
| 1-Me-3-$CF_3$-4-Br-pyrazol-5-yl | O | O | $CF_2CF_3$ |
| 1-Et-3-$CF_3$-pyrazol-5-yl | O | O | $CF_2CF_3$ |
| 1-Et-3-$CF_3CF_2$-pyrazol-5-yl | O | O | $CF_2CF_3$ |
| 1-Et-3-$CF_3CF_2CF_2$-pyrazol-5-yl | O | O | $CF_2CF_3$ |
| 1-Et-pyrazol-5-yl | O | O | $CF_2CF_3$ |
| 1-Et-3-Me-pyrazol-5-yl | O | O | $CF_2CF_3$ |
| 1-Et-3-Et-pyrazol-5-yl | O | O | $CF_2CF_3$ |
| 1-Et-3-Pr-n-pyrazol-5-yl | O | O | $CF_2CF_3$ |
| 1-Et-3-$CH_2F$-pyrazol-5-yl | O | O | $CF_2CF_3$ |
| 1-Et-3-$CHF_2$-pyrazol-5-yl | O | O | $CF_2CF_3$ |
| 1-Et-3-$CO_2Me$-pyrazol-5-yl | O | O | $CF_2CF_3$ |
| 1-Et-3-CN-pyrazol-5-yl | O | O | $CF_2CF_3$ |
| 1-Et-3-$NO_2$-pyrazol-5-yl | O | O | $CF_2CF_3$ |
| 1-Et-3-F-pyrazol-5-yl | O | O | $CF_2CF_3$ |
| 1-Et-3-Cl-pyrazol-5-yl | O | O | $CF_2CF_3$ |
| 1-Et-3-Br-pyrazol-5-yl | O | O | $CF_2CF_3$ |
| 1-Et-3-I-pyrazol-5-yl | O | O | $CF_2CF_3$ |
| 1-Et-3-$CF_3$-4-Cl-pyrazol-5-yl | O | O | $CF_2CF_3$ |
| 1-Et-3-$CF_3$-4-Br-pyrazol-5-yl | O | O | $CF_2CF_3$ |
| 1-Me-3-$CF_3$-pyrazol-5-yl | O | O | Me |
| 1-Me-3-$CF_3CF_2$-pyrazol-5-yl | O | O | Me |
| 1-Me-3-$CF_3CF_2CF_2$-pyrazol-5-yl | O | O | Me |
| 1-Me-pyrazol-5-yl | O | O | Me |
| 1-Me-3-Me-pyrazol-5-yl | O | O | Me |
| 1-Me-3-Et-pyrazol-5-yl | O | O | Me |
| 1-Me-3-Pr-n-pyrazol-5-yl | O | O | Me |
| 1-Me-3-$CH_2F$-pyrazol-5-yl | O | O | Me |
| 1-Me-3-$CHF_2$-pyrazol-5-yl | O | O | Me |
| 1-Me-3-$CO_2Me$-pyrazol-5-yl | O | O | Me |
| 1-Me-3-CN-pyrazol-5-yl | O | O | Me |
| 1-Me-3-$NO_2$-pyrazol-5-yl | O | O | Me |
| 1-Me-3-F-pyrazol-5-yl | O | O | Me |
| 1-Me-3-Cl-pyrazol-5-yl | O | O | Me |
| 1-Me-3-Br-pyrazol-5-yl | O | O | Me |
| 1-Me-3-I-pyrazol-5-yl | O | O | Me |
| 1-Me-3-$CF_3$-4-Cl-pyrazol-5-yl | O | O | Me |
| 1-Me-3-$CF_3$-4-Br-pyrazol-5-yl | O | O | Me |
| 1-Me-3-$CF_3$-pyrazol-5-yl | O | O | Et |
| 1-Me-3-$CF_3$-pyrazol-5-yl | O | O | Pr-iso |
| 1-Me-3-$CF_3$-pyrazol-5-yl | O | O | Pr-n |
| 1-Me-3-$CF_3$-pyrazol-5-yl | O | O | Bu-n |
| 1-Me-3-$CF_3$-pyrazol-5-yl | O | O | Bu-iso |
| 1-Me-3-$CF_3$-pyrazol-5-yl | O | O | Bu-sec |
| 1-Me-3-$CF_3$-pyrazol-5-yl | O | O | Bu-tert |
| 1-Me-3-$CF_3$-pyrazol-5-yl | O | O | Pr-n |
| 1-Me-3-$CF_3$-pyrazol-5-yl | O | O | Pen-n |
| 1-Me-3-$CF_3$-pyrazol-5-yl | O | O | Hex-n |
| 1-Me-3-$CF_3$-pyrazol-5-yl | O | O | Pr-cyc |
| 1-Me-3-$CF_3$-pyrazol-5-yl | O | O | Bu-cyc |
| 1-Me-3-$CF_3$-pyrazol-5-yl | O | O | Pen-cyc |
| 1-Me-3-$CF_3$-pyrazol-5-yl | O | O | Hex-cyc |
| 1-Me-3-$CF_3$-pyrazol-5-yl | O | O | $CH_2F$ |
| 1-Me-3-$CF_3$-pyrazol-5-yl | O | O | $CH_2Cl$ |
| 1-Me-3-$CF_3$-pyrazol-5-yl | O | O | $CH_2Br$ |

TABLE 2-continued

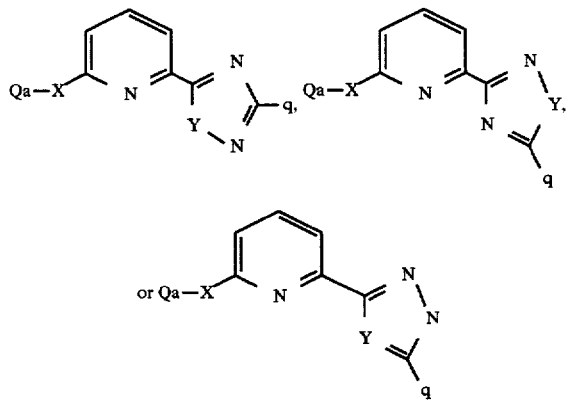

| Qa | X | Y | q |
|---|---|---|---|
| 1-Me-3-CF₃-pyrazol-5-yl | O | O | CH₂I |
| 1-Me-3-CF₃-pyrazol-5-yl | O | O | CHF₂ |
| 1-Me-3-CF₃-pyrazol-5-yl | O | O | CHCl₂ |
| 1-Me-3-CF₃-pyrazol-5-yl | O | O | CHBr₂ |
| 1-Me-3-CF₃-pyrazol-5-yl | O | O | CCl₃ |
| 1-Me-3-CF₃-pyrazol-5-yl | O | O | CBr₃ |
| 1-Me-3-CF₃-pyrazol-5-yl | O | O | CClF₂ |
| 1-Me-3-CF₃-pyrazol-5-yl | O | O | CH₂CF₃ |
| 1-Me-3-CF₃-pyrazol-5-yl | O | O | CH₂CH₂Cl |
| 1-Me-3-CF₃-pyrazol-5-yl | O | O | CH₂CHCl₂ |
| 1-Me-3-CF₃-pyrazol-5-yl | O | O | CH₂CCl₃ |
| 1-Me-3-CF₃-pyrazol-5-yl | O | O | CH₂CH₂Br |
| 1-Me-3-CF₃-pyrazol-5-yl | O | O | CH₂CHBr₂ |
| 1-Me-3-CF₃-pyrazol-5-yl | O | O | CH₂CH₂I |
| 1-Me-3-CF₃-pyrazol-5-yl | O | O | CH₂CH₂CF₃ |
| 1-Me-3-CF₃-pyrazol-5-yl | O | O | CH₂CF₂CF₃ |
| 1-Me-3-CF₃-pyrazol-5-yl | O | O | CF₂CF₂CF₃ |
| 1-Me-3-CF₃-pyrazol-5-yl | O | O | CH₂CH₂CH₂CF₃ |
| 1-Me-3-CF₃-pyrazol-5-yl | O | O | CH₂CH₂CF₂CF₃ |
| 1-Me-3-CF₃-pyrazol-5-yl | O | O | CH₂CF₂CF₂CF₃ |
| 1-Me-3-CF₃-pyrazol-5-yl | O | O | CH₂CH₂CH₂Cl |
| 1-Me-3-CF₃-pyrazol-5-yl | O | O | CH₂CH₂CH₂CH₂Cl |
| 2-CF₃—Ph | O | S | CF₃ |
| 3-CF₃—Ph | O | S | CF₃ |
| 1-Me-3-CF₃-pyrazol-5-yl | O | S | CF₃ |
| 2-CF₃—Ph | O | S | CF₂CF₃ |
| 3-CF₃—Ph | O | S | CF₂CF₃ |
| 1-Me-3-CF₃-pyrazol-5-yl | O | S | CF₂CF₃ |
| 2-CF₃—Ph | O | S | Me |
| 3-CF₃—Ph | O | S | Me |
| 1-Me-3-CF₃-pyrazol-5-yl | O | S | Me |
| 2-CF₃—Ph | O | S | Et |
| 3-CF₃—Ph | O | S | Et |
| 1-Me-3-CF₃-pyrazol-5-yl | O | S | Et |
| 2-CF₃—Ph | O | NH | CF₃ |
| 3-CF₃—Ph | O | NH | CF₃ |
| 1-Me-3-CF₃-pyrazol-5-yl | O | NH | CF₃ |
| 2-CF₃—Ph | O | NH | CF₂CF₃ |
| 3-CF₃—Ph | O | NH | CF₂CF₃ |
| 1-Me-3-CF₃-pyrazol-5-yl | O | NH | CF₂CF₃ |
| 2-CF₃—Ph | O | NH | Me |
| 3-CF₃—Ph | O | NH | Me |
| 1-Me-3-CF₃-pyrazol-5-yl | O | NH | Me |
| 2-CF₃—Ph | O | NH | Et |
| 3-CF₃—Ph | O | NH | Et |
| 1-Me-3-CF₃-pyrazol-5-yl | O | NH | Et |
| 2-CF₃—Ph | O | NMe | CF₃ |
| 3-CF₃—Ph | O | NMe | CF₃ |
| 1-Me-3-CF₃-pyrazol-5-yl | O | NMe | CF₃ |
| 2-CF₃—Ph | O | NMe | CF₂CF₃ |
| 3-CF₃—Ph | O | NMe | CF₂CF₃ |
| 1-Me-3-CF₃-pyrazol-5-yl | O | NMe | CF₂CF₃ |
| 2-CF₃—Ph | O | NMe | Me |
| 3-CF₃—Ph | O | NMe | Me |
| 1-Me-3-CF₃-pyrazol-5-yl | O | NMe | Me |
| 2-CF₃—Ph | O | NMe | Et |
| 3-CF₃—Ph | O | NMe | Et |

TABLE 2-continued

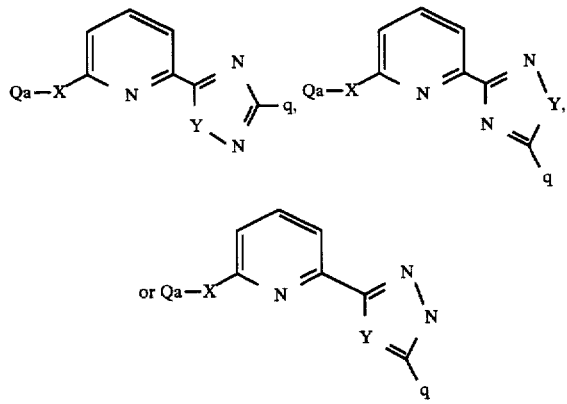

| Qa | X | Y | q |
|---|---|---|---|
| 1-Me-3-CF$_3$-pyrazol-5-yl | O | NMe | Et |
| 2-CF$_3$—Ph | S | O | CF$_3$ |
| 3-CF$_3$—Ph | S | O | CF$_3$ |
| 1-Me-3-CF$_3$-pyrazol-5-yl | S | O | CF$_3$ |
| 2-CF$_3$—Ph | NH | O | CF$_3$ |
| 3-CF$_3$—Ph | NH | O | CF$_3$ |
| 1-Me-3-CF$_3$-pyrazol-5-yl | NH | O | CF$_3$ |
| 2-CF$_3$—Ph | NMe | O | CF$_3$ |
| 3-CF$_3$—Ph | NMe | O | CF$_3$ |
| 1-Me-3-CF$_3$-pyrazol-5-yl | NMe | O | CF$_3$ |
| pyridin-2-yl | O | O | CF$_3$ |
| pyridin-3-yl | O | O | CF$_3$ |
| pyridin-4-yl | O | O | CF$_3$ |
| 2-Cl-pyridin-4-yl | O | O | CF$_3$ |
| 2-Cl-pyridin-6-yl | O | O | CF$_3$ |
| 3-Cl-pyridin-5-yl | O | O | CF$_3$ |
| 3-Cl-pyridin-6-yl | O | O | CF$_3$ |
| 2-Me-pyridin-5-yl | O | O | CF$_3$ |
| 2-Me-pyridin-6-yl | O | O | CF$_3$ |
| 6-Me-pyridin-3-yl | O | O | CF$_3$ |
| pyridin-2-yl | O | O | CH$_2$CF$_3$ |
| pyridin-3-yl | O | O | CH$_2$CF$_3$ |
| pyridin-4-yl | O | O | CH$_2$CF$_3$ |
| 2-Cl-pyridin-4-yl | O | O | CH$_2$CF$_3$ |
| 2-Cl-pyridin-6-yl | O | O | CH$_2$CF$_3$ |
| 3-Cl-pyridin-5-yl | O | O | CH$_2$CF$_3$ |
| 3-Cl-pyridin-6-yl | O | O | CH$_2$CF$_3$ |
| 2-Me-pyridin-5-yl | O | O | CH$_2$CF$_3$ |
| 2-Me-pyridin-6-yl | O | O | CH$_2$CF$_3$ |
| 6-Me-pyridin-3-yl | O | O | CH$_2$CF$_3$ |
| 2-Cl-pyridin-4-yl | O | O | Me |
| 2-Cl-pyridin-6-yl | O | O | Me |
| 3-Cl-pyridin-5-yl | O | O | Me |
| 3-Cl-pyridin-6-yl | O | O | Me |
| 3-CF$_3$—Ph | O | O | CH$_2$OMe |
| 3-CF$_3$—Ph | O | O | CH$_2$CH$_2$OMe |
| 3-CF$_3$—Ph | O | O | CH$_2$CH$_2$CH$_2$OMe |
| 3-CF$_3$—Ph | O | O | CH$_2$CH$_2$CH$_2$CH$_2$OMe |
| 3-CF$_3$—Ph | O | O | CH$_2$OEt |
| 3-CF$_3$—Ph | O | O | CH$_2$OPr-n |
| 3-CF$_3$—Ph | O | O | CH$_2$OBu-n |
| 3-CF$_3$—Ph | O | O | CH$_2$OCH$_2$CF$_3$ |
| 3-CF$_3$—Ph | O | O | CH$_2$CH$_2$OCH$_2$CF$_3$ |
| 3-CF$_3$—Ph | O | O | CH$_2$CH$_2$CH$_2$OCH$_2$CF$_3$ |
| 3-CF$_3$—Ph | O | O | CH$_2$CH$_2$CH$_2$CH$_2$OCH$_2$CF$_3$ |
| 3-CF$_3$—Ph | O | O | CH$_2$OCH$_2$CH$_2$F |
| 3-CF$_3$—Ph | O | O | CH$_2$OCH$_2$CH$_2$Cl |
| 3-CF$_3$—Ph | O | O | CH$_2$OCH$_2$CH$_2$Br |
| 3-CF$_3$—Ph | O | O | Ph |
| 3-CF$_3$—Ph | O | O | CH$_2$Ph |
| 3-CF$_3$—Ph | O | O | 3-Py |
| 3-CF$_3$—Ph | O | O | CO$_2$Me |
| 3-CF$_3$—Ph | O | O | CO$_2$Et |
| 3-CF$_3$—Ph | O | O | CO$_2$Pr-n |
| 3-CF$_3$—Ph | O | O | CO$_2$Bu-n |
| 3-CF$_3$—Ph | O | O | CH=CH$_2$ |
| 3-CF$_3$—Ph | O | O | CH=CHMe |

TABLE 2-continued

| Qa | X | Y | q |
|---|---|---|---|
| 3-CF₃—Ph | O | O | CH=CMe₂ |
| 3-CF₃—Ph | O | O | CH₂CH=CH₂ |
| 3-CF₃—Ph | O | O | CH₂CH=CHMe |
| 3-CF₃—Ph | O | O | OCH₂F |
| 3-CF₃—Ph | O | O | OCHF₂ |
| 3-CF₃—Ph | O | O | OCF₃ |
| 3-CF₃—Ph | O | O | OCBrF₂ |
| 3-CF₃—Ph | O | O | OCH₂CF₃ |
| 3-CF₃—Ph | O | O | OCF₂CF₃ |
| 3-CF₃—Ph | O | O | OCH₂CH₂Cl |
| 3-CF₃—Ph | O | O | OCH₂CHCl₂ |
| 3-CF₃—Ph | O | O | OCH₂CH₂CF₃ |
| 3-CF₃—Ph | O | O | OCH₂CF₂CF₃ |
| 3-CF₃—Ph | O | O | OCF₂CF₂CF₃ |
| 3-CF₃—Ph | O | O | OCH₂CH₂CH₂CH₂Cl |
| 3-CF₃—Ph | O | O | SMe |
| 3-CF₃—Ph | O | O | SEt |
| 3-CF₃—Ph | O | O | SPr-n |
| 3-CF₃—Ph | O | O | SPr-iso |
| 3-CF₃—Ph | O | O | SBu-n |
| 3-CF₃—Ph | O | O | S(O)Me |
| 3-CF₃—Ph | O | O | S(O)Et |
| 3-CF₃—Ph | O | O | S(O)Pr-n |
| 3-CF₃—Ph | O | O | S(O)Pr-iso |
| 3-CF₃—Ph | O | O | S(O)Bu-n |
| 3-CF₃—Ph | O | O | SO₂Me |
| 3-CF₃—Ph | O | O | SO₂Et |
| 3-CF₃—Ph | O | O | SO₂Pr-n |
| 3-CF₃—Ph | O | O | SO₂Pr-iso |
| 3-CF₃—Ph | O | O | SO₂Bu-n |
| 3-CF₃—Ph | O | O | OCH=CH₂ |
| 3-CF₃—Ph | O | O | OCH=CHMe |
| 3-CF₃—Ph | O | O | OCH=CMe₂ |
| 3-CF₃—Ph | O | O | OCH₂CH=CH₂ |
| 3-CF₃—Ph | O | O | OCH₂CH=CHMe |
| 3-CF₃—Ph | O | O | OCH₂C≡CH |
| 3-CF₃—Ph | O | O | OCH₂C≡CMe |
| 3-CF₃—Ph | O | O | SCH₂F |
| 3-CF₃—Ph | O | O | SCHF₂ |
| 3-CF₃—Ph | O | O | SCF₃ |
| 3-CF₃—Ph | O | O | SCBrF₂ |
| 3-CF₃—Ph | O | O | SCH₂CF₃ |
| 3-CF₃—Ph | O | O | SCF₂CF₃ |
| 3-CF₃—Ph | O | O | SCH₂CH₂Cl |
| 3-CF₃—Ph | O | O | SCH₂CHCl₂ |
| 3-CF₃—Ph | O | O | SCH₂CH₂CF₃ |
| 3-CF₃—Ph | O | O | SCH₂CF₂CF₃ |
| 3-CF₃—Ph | O | O | SCF₂CF₂CF₃ |
| 3-CF₃—Ph | O | O | SCH₂CH₂CH₂CH₂Cl |
| 3-CF₃—Ph | O | O | SCH=CH₂ |
| 3-CF₃—Ph | O | O | SCH=CHMe |
| 3-CF₃—Ph | O | O | SCH=CMe₂ |
| 3-CF₃—Ph | O | O | SCH₂CH=CH₂ |
| 3-CF₃—Ph | O | O | SCH₂CH=CHMe |

TABLE 2-continued

| Qa | X | Y | q |
|---|---|---|---|
| 3-CF$_3$—Ph | O | O | SCH$_2$C≡CH |
| 3-CF$_3$—Ph | O | O | SCH$_2$C≡CMe |
| 3-CF$_3$—Ph | O | O | NHMe |
| 3-CF$_3$—Ph | O | O | NHEt |
| 3-CF$_3$—Ph | O | O | NHPr-n |
| 3-CF$_3$—Ph | O | O | NHPr-iso |
| 3-CF$_3$—Ph | O | O | NHBu-n |
| 3-CF$_3$—Ph | O | O | NHCH$_2$CF$_3$ |
| 3-CF$_3$—Ph | O | O | NHCF$_2$CF$_3$ |
| 3-CF$_3$—Ph | O | O | NHCH$_2$CH$_2$Cl |
| 3-CF$_3$—Ph | O | O | NHCH$_2$CHCl$_2$ |
| 3-CF$_3$—Ph | O | O | NHCH$_2$CH$_2$CF$_3$ |
| 3-CF$_3$—Ph | O | O | NHCH$_2$CF$_2$CF$_3$ |
| 3-CF$_3$—Ph | O | O | NHCF$_2$CF$_2$CF$_3$ |
| 3-CF$_3$—Ph | O | O | NHCH$_2$CH$_2$CH$_2$CH$_2$Cl |
| 3-CF$_3$—Ph | O | O | NMe$_2$ |
| 3-CF$_3$—Ph | O | O | NEt$_2$ |
| 3-CF$_3$—Ph | O | O | N(Pr-n)$_2$ |
| 3-CF$_3$—Ph | O | O | N(Pr-iso)$_2$ |
| 3-CF$_3$—Ph | O | O | N(Bu-n)$_2$ |
| 3-CF$_3$—Ph | O | O | N(CH$_2$CF$_3$)$_2$ |
| 3-CF$_3$—Ph | O | O | N(CF$_2$CF$_3$)$_2$ |
| 3-CF$_3$—Ph | O | O | N(CH$_2$CH$_2$Cl)$_2$ |
| 3-CF$_3$—Ph | O | O | N(CH$_2$CHCl$_2$)$_2$ |
| 3-CF$_3$—Ph | O | O | N(CH$_2$CH$_2$CF$_3$)$_2$ |
| 3-CF$_3$—Ph | O | O | N(CH$_2$CF$_2$CF$_3$)$_2$ |
| 3-CF$_3$—Ph | O | O | N(CF$_2$CF$_2$CF$_3$)$_2$ |
| 3-CF$_3$—Ph | O | O | N(CH$_2$CH$_2$CH$_2$CH$_2$Cl)$_2$ |
| 1-Me-3-CF$_3$-pyrazol-5-yl | O | O | CH$_2$OMe |
| 1-Me-3-CF$_3$-pyrazol-5-yl | O | O | CH$_2$CH$_2$OMe |
| 1-Me-3-CF$_3$-pyrazol-5-yl | O | O | CH$_2$CH$_2$CH$_2$OMe |
| 1-Me-3-CF$_3$-pyrazol-5-yl | O | O | CH$_2$CH$_2$CH$_2$CH$_2$OMe |
| 1-Me-3-CF$_3$-pyrazol-5-yl | O | O | CH$_2$OEt |
| 1-Me-3-CF$_3$-pyrazol-5-yl | O | O | CH$_2$OPr-n |
| 1-Me-3-CF$_3$-pyrazol-5-yl | O | O | CH$_2$OBu-n |
| 1-Me-3-CF$_3$-pyrazol-5-yl | O | O | CH$_2$OCH$_2$CF$_3$ |
| 1-Me-3-CF$_3$-pyrazol-5-yl | O | O | CH$_2$CH$_2$OCH$_2$CF$_3$ |
| 1-Me-3-CF$_3$-pyrazol-5-yl | O | O | CH$_2$CH$_2$CH$_2$OCH$_2$CF$_3$ |
| 1-Me-3-CF$_3$-pyrazol-5-yl | O | O | CH$_2$CH$_2$CH$_2$CH$_2$OCH$_2$CF$_3$ |
| 1-Me-3-CF$_3$-pyrazol-5-yl | O | O | CH$_2$OCH$_2$CH$_2$F |
| 1-Me-3-CF$_3$-pyrazol-5-yl | O | O | CH$_2$OCH$_2$CH$_2$Cl |
| 1-Me-3-CF$_3$-pyrazol-5-yl | O | O | CH$_2$OCH$_2$CH$_2$Br |
| 1-Me-3-CF$_3$-pyrazol-5-yl | O | O | Ph |
| 1-Me-3-CF$_3$-pyrazol-5-yl | O | O | CH$_2$Ph |
| 1-Me-3-CF$_3$-pyrazol-5-yl | O | O | 3-Py |
| 1-Me-3-CF$_3$-pyrazol-5-yl | O | O | CO$_2$Me |
| 1-Me-3-CF$_3$-pyrazol-5-yl | O | O | CO$_2$Et |
| 1-Me-3-CF$_3$-pyrazol-5-yl | O | O | CO$_2$Pr-n |
| 1-Me-3-CF$_3$-pyrazol-5-yl | O | O | CO$_2$Bu-n |
| 1-Me-3-CF$_3$-pyrazol-5-yl | O | O | CH=CH$_2$ |
| 1-Me-3-CF$_3$-pyrazol-5-yl | O | O | CH=CHMe |
| 1-Me-3-CF$_3$-pyrazol-5-yl | O | O | CH=CMe$_2$ |
| 1-Me-3-CF$_3$-pyrazol-5-yl | O | O | CH$_2$CH=CH$_2$ |
| 1-Me-3-CF$_3$-pyrazol-5-yl | O | O | CH$_2$CH=CHMe |
| 1-Me-3-CF$_3$-pyrazol-5-yl | O | O | OCH$_2$F |

TABLE 2-continued

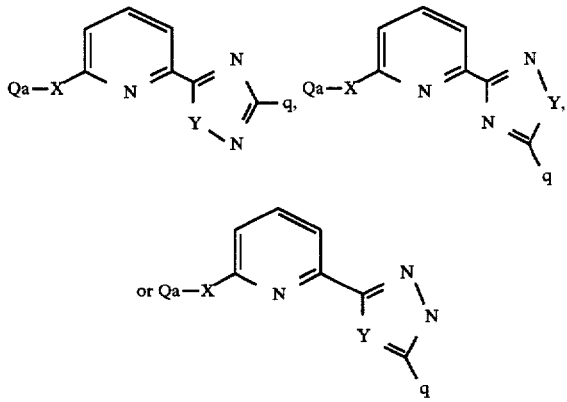

| Qa | X | Y | q |
|---|---|---|---|
| 1-Me-3-CF₃-pyrazol-5-yl | O | O | OCHF₂ |
| 1-Me-3-CF₃-pyrazol-5-yl | O | O | OCF₃ |
| 1-Me-3-CF₃-pyrazol-5-yl | O | O | OCBrF₂ |
| 1-Me-3-CF₃-pyrazol-5-yl | O | O | OCH₂CF₃ |
| 1-Me-3-CF₃-pyrazol-5-yl | O | O | OCF₂CF₃ |
| 1-Me-3-CF₃-pyrazol-5-yl | O | O | OCH₂CH₂Cl |
| 1-Me-3-CF₃-pyrazol-5-yl | O | O | OCH₂CHCl₂ |
| 1-Me-3-CF₃-pyrazol-5-yl | O | O | OCH₂CH₂CF₃ |
| 1-Me-3-CF₃-pyrazol-5-yl | O | O | OCH₂CF₂CF₃ |
| 1-Me-3-CF₃-pyrazol-5-yl | O | O | OCF₂CF₂CF₃ |
| 1-Me-3-CF₃-pyrazol-5-yl | O | O | OCH₂CH₂CH₂CH₂Cl |
| 1-Me-3-CF₃-pyrazol-5-yl | O | O | SMe |
| 1-Me-3-CF₃-pyrazol-5-yl | O | O | SEt |
| 1-Me-3-CF₃-pyrazol-5-yl | O | O | SPr-n |
| 1-Me-3-CF₃-pyrazol-5-yl | O | O | SPr-iso |
| 1-Me-3-CF₃-pyrazol-5-yl | O | O | SBu-n |
| 1-Me-3-CF₃-pyrazol-5-yl | O | O | S(O)Me |
| 1-Me-3-CF₃-pyrazol-5-yl | O | O | S(O)Et |
| 1-Me-3-CF₃-pyrazol-5-yl | O | O | S(O)Pr-n |
| 1-Me-3-CF₃-pyrazol-5-yl | O | O | S(O)Pr-iso |
| 1-Me-3-CF₃-pyrazol-5-yl | O | O | S(O)Bu-n |
| 1-Me-3-CF₃-pyrazol-5-yl | O | O | SO₂Me |
| 1-Me-3-CF₃-pyrazol-5-yl | O | O | SO₂Et |
| 1-Me-3-CF₃-pyrazol-5-yl | O | O | SO₂Pr-n |
| 1-Me-3-CF₃-pyrazol-5-yl | O | O | SO₂Pr-iso |
| 1-Me-3-CF₃-pyrazol-5-yl | O | O | SO₂Bu-n |
| 1-Me-3-CF₃-pyrazol-5-yl | O | O | OCH=CH₂ |
| 1-Me-3-CF₃-pyrazol-5-yl | O | O | OCH=CHMe |
| 1-Me-3-CF₃-pyrazol-5-yl | O | O | OCH=CMe₂ |
| 1-Me-3-CF₃-pyrazol-5-yl | O | O | OCH₂CH=CH₂ |
| 1-Me-3-CF₃-pyrazol-5-yl | O | O | OCH₂CH=CHMe |
| 1-Me-3-CF₃-pyrazol-5-yl | O | O | OC≡CH |
| 1-Me-3-CF₃-pyrazol-5-yl | O | O | OCH₂C≡CH |
| 1-Me-3-CF₃-pyrazol-5-yl | O | O | OCH₂C≡CMe |
| 1-Me-3-CF₃-pyrazol-5-yl | O | O | SCH₂F |
| 1-Me-3-CF₃-pyrazol-5-yl | O | O | SCHF₂ |
| 1-Me-3-CF₃-pyrazol-5-yl | O | O | SCF₃ |
| 1-Me-3-CF₃-pyrazol-5-yl | O | O | SCBrF₂ |
| 1-Me-3-CF₃-pyrazol-5-yl | O | O | SCH₂CF₃ |
| 1-Me-3-CF₃-pyrazol-5-yl | O | O | SCF₂CF₃ |
| 1-Me-3-CF₃-pyrazol-5-yl | O | O | SCH₂CH₂Cl |
| 1-Me-3-CF₃-pyrazol-5-yl | O | O | SCH₂CHCl₂ |
| 1-Me-3-CF₃-pyrazol-5-yl | O | O | SCH₂CH₂CF₃ |
| 1-Me-3-CF₃-pyrazol-5-yl | O | O | SCH₂CF₂CF₃ |
| 1-Me-3-CF₃-pyrazol-5-yl | O | O | SCF₂CF₂CF₃ |
| 1-Me-3-CF₃-pyrazol-5-yl | O | O | SCH₂CH₂CH₂CH₂Cl |
| 1-Me-3-CF₃-pyrazol-5-yl | O | O | SCH=CH₂ |
| 1-Me-3-CF₃-pyrazol-5-yl | O | O | SCH=CHMe |
| 1-Me-3-CF₃-pyrazol-5-yl | O | O | SCH=CMe₂ |
| 1-Me-3-CF₃-pyrazol-5-yl | O | O | SCH₂CH=CH₂ |
| 1-Me-3-CF₃-pyrazol-5-yl | O | O | SCH₂CH=CHMe |
| 1-Me-3-CF₃-pyrazol-5-yl | O | O | SC≡CH |
| 1-Me-3-CF₃-pyrazol-5-yl | O | O | SCH₂C≡CH |

TABLE 2-continued

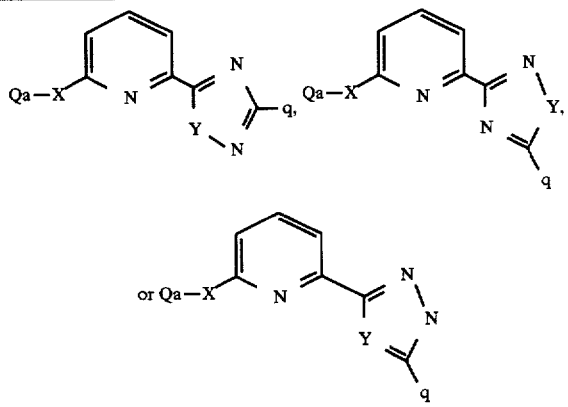

| Qa | X | Y | q |
|---|---|---|---|
| 1-Me-3-CF$_3$-pyrazol-5-yl | O | O | SCH$_2$C≡CMe |
| 1-Me-3-CF$_3$-pyrazol-5-yl | O | O | NHMe |
| 1-Me-3-CF$_3$-pyrazol-5-yl | O | O | NHEt |
| 1-Me-3-CF$_3$-pyrazol-5-yl | O | O | NHPr-n |
| 1-Me-3-CF$_3$-pyrazol-5-yl | O | O | NHPr-iso |
| 1-Me-3-CF$_3$-pyrazol-5-yl | O | O | NHBu-n |
| 1-Me-3-CF$_3$-pyrazol-5-yl | O | O | NHCH$_2$CF$_3$ |
| 1-Me-3-CF$_3$-pyrazol-5-yl | O | O | NHCF$_2$CF$_3$ |
| 1-Me-3-CF$_3$-pyrazol-5-yl | O | O | NHCH$_2$CH$_2$Cl |
| 1-Me-3-CF$_3$-pyrazol-5-yl | O | O | NHCH$_2$CHCl$_2$ |
| 1-Me-3-CF$_3$-pyrazol-5-yl | O | O | NHCH$_2$CH$_2$CF$_3$ |
| 1-Me-3-CF$_3$-pyrazol-5-yl | O | O | NHCH$_2$CF$_2$CF$_3$ |
| 1-Me-3-CF$_3$-pyrazol-5-yl | O | O | NHCF$_2$CF$_2$CF$_3$ |
| 1-Me-3-CF$_3$-pyrazol-5-yl | O | O | NHCH$_2$CH$_2$CH$_2$CH$_2$Cl |
| 1-Me-3-CF$_3$-pyrazol-5-yl | O | O | NMe$_2$ |
| 1-Me-3-CF$_3$-pyrazol-5-yl | O | O | NEt$_2$ |
| 1-Me-3-CF$_3$-pyrazol-5-yl | O | O | N(Pr-n)$_2$ |
| 1-Me-3-CF$_3$-pyrazol-5-yl | O | O | N(Pr-iso)$_2$ |
| 1-Me-3-CF$_3$-pyrazol-5-yl | O | O | N(Bu-n)$_2$ |
| 1-Me-3-CF$_3$-pyrazol-5-yl | O | O | N(CH$_2$CF$_3$)$_2$ |
| 1-Me-3-CF$_3$-pyrazol-5-yl | O | O | N(CF$_2$CF$_3$)$_2$ |
| 1-Me-3-CF$_3$-pyrazol-5-yl | O | O | N(CH$_2$CH$_2$Cl)$_2$ |
| 1-Me-3-CF$_3$-pyrazol-5-yl | O | O | N(CH$_2$CHCl$_2$)$_2$ |
| 1-Me-3-CF$_3$-pyrazol-5-yl | O | O | N(CH$_2$CH$_2$CF$_3$)$_2$ |
| 1-Me-3-CF$_3$-pyrazol-5-yl | O | O | N(CH$_2$CF$_2$CF$_3$)$_2$ |
| 1-Me-3-CF$_3$-pyrazol-5-yl | O | O | N(CF$_2$CF$_2$CF$_3$)$_2$ |
| 1-Me-3-CF$_3$-pyrazol-5-yl | O | O | N(CH$_2$CH$_2$CH$_2$CH$_2$Cl)$_2$ |
| 2-CF$_3$—Ph | O | O | Pr-cyc |
| 4-CF$_3$—Ph | O | O | Pr-cyc |
| 2-Me—Ph | O | O | Pr-cyc |
| 3-Me—Ph | O | O | Pr-cyc |
| 4-Me—Ph | O | O | Pr-cyc |
| 2-Et—Ph | O | O | Pr-cyc |
| 3-Et—Ph | O | O | Pr-cyc |
| 4-Et—Ph | O | O | Pr-cyc |
| 2-F—Ph | O | O | Pr-cyc |
| 3-F—Ph | O | O | Pr-cyc |
| 4-F—Ph | O | O | Pr-cyc |
| 2-Cl—Ph | O | O | Pr-cyc |
| 3-Cl—Ph | O | O | Pr-cyc |
| 4-Cl—Ph | O | O | Pr-cyc |
| 2-Br—Ph | O | O | Pr-cyc |
| 3-Br—Ph | O | O | Pr-cyc |
| 4-Br—Ph | O | O | Pr-cyc |
| 2-MeO—Ph | O | O | Pr-cyc |
| 3-MeO—Ph | O | O | Pr-cyc |
| 4-MeO—Ph | O | O | Pr-cyc |
| 2,4-Cl$_2$—Ph | O | O | Pr-cyc |
| 2-Cl-pyridin-4-yl | O | O | Pr-cyc |
| 1-Me-3-CF$_3$-pyrazol-5-yl | O | S | Pr-cyc |
| 2-Cl-pyridin-4-yl | O | S | Pr-cyc |
| 2-CF$_3$—Ph | O | S | Pr-cyc |
| 3-CF$_3$—Ph | O | S | Pr-cyc |
| 4-CF$_3$—Ph | O | S | Pr-cyc |
| 2-Me—Ph | O | S | Pr-cyc |
| 3-Me—Ph | O | S | Pr-cyc |

TABLE 2-continued

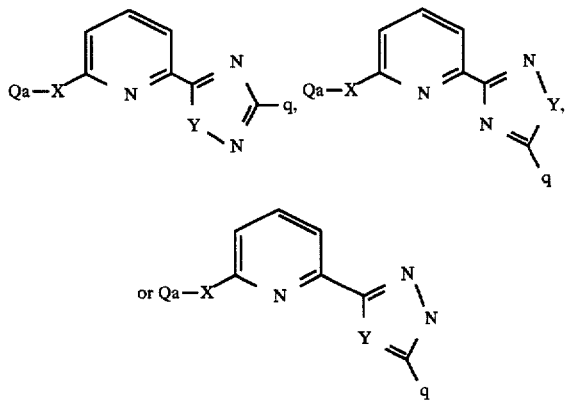

| Qa | X | Y | q |
|---|---|---|---|
| 4-Me—Ph | O | S | Pr-cyc |
| 2-Et—Ph | O | S | Pr-cyc |
| 3-Et—Ph | O | S | Pr-cyc |
| 4-Et—Ph | O | S | Pr-cyc |
| 2-F—Ph | O | S | Pr-cyc |
| 3-F—Ph | O | S | Pr-cyc |
| 4-F—Ph | O | S | Pr-cyc |
| 2-Cl—Ph | O | S | Pr-cyc |
| 3-Cl—Ph | O | S | Pr-cyc |
| 4-Cl—Ph | O | S | Pr-cyc |
| 2-Br—Ph | O | S | Pr-cyc |
| 3-Br—Ph | O | S | Pr-cyc |
| 4-Br—Ph | O | S | Pr-cyc |
| 2-MeO—Ph | O | S | Pr-cyc |
| 3-MeO—Ph | O | S | Pr-cyc |
| 4-MeO—Ph | O | S | Pr-cyc |
| 2,4-Cl$_2$—Ph | O | S | Pr-cyc |
| pyridin-2-yl | O | O | CF$_2$CF$_3$ |
| pyridin-3-yl | O | O | CF$_2$CF$_3$ |
| pyridin-4-yl | O | O | CF$_2$CF$_3$ |
| 2-Cl-pyridin-4-yl | O | O | CF$_2$CF$_3$ |
| 2-Cl-pyridin-6-yl | O | O | CF$_2$CF$_3$ |
| 3-Cl-pyridin-5-yl | O | O | CF$_2$CF$_3$ |
| 3-Cl-pyridin-6-yl | O | O | CF$_2$CF$_3$ |
| 2-Me-pyridin-5-yl | O | O | CF$_2$CF$_3$ |
| 2-Me-pyridin-6-yl | O | O | CF$_2$CF$_3$ |
| 6-Me-pyridin-3-yl | O | O | CF$_2$CF$_3$ |
| 3-CF$_3$—Ph | O | O | 2-Me—Pr-cyc |
| 1-Me-3-CF$_3$-pyrazol-5-yl | O | O | CMe=CH$_2$ |
| 2-Cl-pyridin-4-yl | O | O | CMe=CH$_2$ |
| 3-CF$_3$—Ph | O | O | CONH$_2$ |
| 1-Me-3-CF$_3$-pyrazol-5-yl | O | O | CONH$_2$ |
| 2-Cl-pyridin-4-yl | O | O | CONH$_2$ |
| 3-CF$_3$—Ph | O | O | CONH—Py-cyc |
| 1-Me-3-CF$_3$-pyrazol-5-yl | O | O | CONH—Py-cyc |
| 2-Cl-pyridin-4-yl | O | O | CONH—Py-cyc |
| 3-CF$_3$—Ph | O | O | OH |
| 1-Me-3-CF$_3$-pyrazol-5-yl | O | O | OH |
| 2-Cl-pyridin-4-yl | O | O | OH |
| 3-CF$_3$—Ph | O | O | Epo |
| 1-Me-3-CF$_3$-pyrazol-5-yl | O | O | Epo |
| 2-Cl-pyridin-4-yl | O | O | Epo |
| 3-CF$_3$—Ph | O | O | 1-Me—Epo |
| 1-Me-3-CF$_3$-pyrazol-5-yl | O | O | 1-Me—Epo |
| 2-Cl-pyridin-4-yl | O | O | 1-Me—Epo |
| 1-Me-3-CF$_3$-pyrazol-5-yl | O | O | CN |
| 2-Cl-pyridin-4-yl | O | O | CN |
| 1-Me-3-CF$_3$-pyrazol-5-yl | O | O | H |
| 2-Cl-pyridin-4-yl | O | O | H |
| 3-CF$_3$—Ph | O | O | CF$_2$Br |
| 1-Me-3-CF$_3$-pyrazol-5-yl | O | O | CF$_2$Br |
| 2-Cl-pyridin-4-yl | O | O | CF$_2$Br |
| 3-CF$_3$—Ph | O | O | CF$_2$I |
| 1-Me-3-CF$_3$-pyrazol-5-yl | O | O | CF$_2$I |
| 2-Cl-pyridin-4-yl | O | O | CF$_2$I |
| 2-Cl-pyridin-4-yl | O | O | OCH$_2$F |
| 2-Cl-pyridin-4-yl | O | O | OCHF$_2$ |

TABLE 2-continued

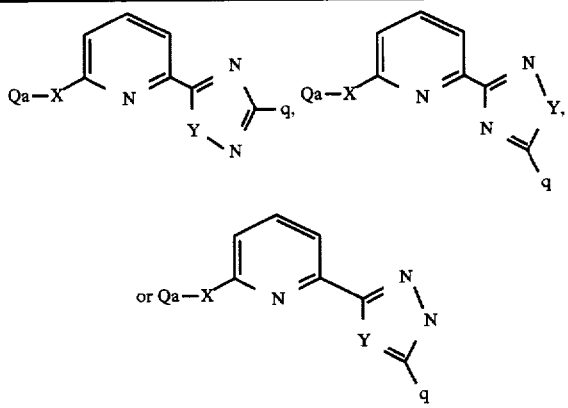

| Qa | X | Y | q |
|---|---|---|---|
| 2-Cl-pyridin-4-yl | O | O | OCF$_3$ |
| 3-CF$_3$—Ph | O | O | CFMe$_2$ |
| 1-Me-3-CF$_3$-pyrazol-5-yl | O | O | CFMe$_2$ |
| 2-Cl-pyridin-4-yl | O | O | CFMe$_2$ |
| 3-CF$_3$—Ph | O | O | CH(CF$_3$)$_2$ |
| 1-Me-3-CF$_3$-pyrazol-5-yl | O | O | CH(CF$_3$)$_2$ |
| 2-Cl-pyridin-4-yl | O | O | CH(CF$_3$)$_2$ |
| 3-CF$_3$—Ph | O | O | CH(CF$_3$)Me |
| 1-Me-3-CF$_3$-pyrazol-5-yl | O | O | CH(CF$_3$)Me |
| 2-Cl-pyridin-4-yl | O | O | CH(CF$_3$)Me |
| 3-CF$_3$—Ph | O | O | CF$_2$Me |
| 1-Me-3-CF$_3$-pyrazol-5-yl | O | O | CF$_2$Me |
| 2-Cl-pyridin-4-yl | O | O | CF$_2$Me |
| 3-CF$_3$—Ph | O | O | CHFMe |
| 1-Me-3-CF$_3$-pyrazol-5-yl | O | O | CHFMe |
| 2-Cl-pyridin-4-yl | O | O | CHFMe |
| 3-CF$_3$—Ph | O | O | 2-F—Pr-cyc |
| 1-Me-3-CF$_3$-pyrazol-5-yl | O | O | 2-F—Pr-cyc |
| 2-Cl-pyridin-4-yl | O | O | 2-F—Pr-cyc |
| 3-CF$_3$—Ph | O | O | 2,2-F$_2$—Pr-cyc |
| 1-Me-3-CF$_3$-pyrazol-5-yl | O | O | 2,2-F$_2$—Pr-cyc |
| 2-Cl-pyridin-4-yl | O | O | 2,2-F$_2$—Pr-cyc |
| 3-CF$_3$—Ph | O | O | 2,2,3,3-F$_4$—Pr-cyc |
| 1-Me-3-CF$_3$-pyrazol-5-yl | O | O | 2,2,3,3-F$_4$—Pr-cyc |
| 2-Cl-pyridin-4-yl | O | O | 2,2,3,3-F$_4$—Pr-cyc |
| 3-CF$_3$—Ph | O | O | 2-Cl—Pr-cyc |
| 1-Me-3-CF$_3$-pyrazol-5-yl | O | O | 2-Cl—Pr-cyc |
| 2-Cl-pyridin-4-yl | O | O | 2-Cl—Pr-cyc |
| 3-CF$_3$—Ph | O | O | 2,2-Cl$_2$—Pryc |
| 1-Me-3-CF$_3$-pyrazol-5-yl | O | O | 2,2-Cl$_2$—Pryc |
| 2-Cl-pyridin-4-yl | O | O | 2,2-Cl$_2$—Pryc |
| 3-CF$_3$—Ph | O | O | CH=CF$_2$ |
| 1-Me-3-CF$_3$-pyrazol-5-yl | O | O | CH=CF$_2$ |
| 2-Cl-pyridin-4-yl | O | O | CH=CF$_2$ |
| 3-CF$_3$—Ph | O | S | CMe=CH$_2$ |
| 1-Me-3-CF$_3$-pyrazol-5-yl | O | S | CMe=CH$_2$ |
| 2-Cl-pyridin-4-yl | O | S | CMe=CH$_2$ |
| 3-CF$_3$—Ph | O | S | CONH$_2$ |
| 1-Me-3-CF$_3$-pyrazol-5-yl | O | S | CONH$_2$ |
| 2-Cl-pyridin-4-yl | O | S | CONH$_2$ |
| 3-CF$_3$—Ph | O | S | CONH—Py-cyc |
| 1-Me-3-CF$_3$-pyrazol-5-yl | O | S | CONH—Py-cyc |
| 2-Cl-pyridin-4-yl | O | S | CONH—Py-cyc |
| 3-CF$_3$—Ph | O | S | OH |
| 1-Me-3-CF$_3$-pyrazol-5-yl | O | S | OH |
| 2-Cl-pyridin-4-yl | O | S | OH |
| 3-CF$_3$—Ph | O | S | Epo |
| 1-Me-3-CF$_3$-pyrazol-5-yl | O | S | Epo |
| 2-Cl-pyridin-4-yl | O | S | Epo |
| 3-CF$_3$—Ph | O | S | 1-Me—Epo |
| 1-Me-3-CF$_3$-pyrazol-5-yl | O | S | 1-Me—Epo |
| 2-Cl-pyridin-4-yl | O | S | 1-Me—Epo |
| 1-Me-3-CF$_3$-pyrazol-5-yl | O | S | CN |
| 2-Cl-pyridin-4-yl | O | S | CN |
| 1-Me-3-CF$_3$-pyrazol-5-yl | O | S | H |
| 2-Cl-pyridin-4-yl | O | S | H |
| 3-CF$_3$—Ph | O | S | CF$_2$Br |

TABLE 2-continued

| Qa | X | Y | q |
|---|---|---|---|
| 1-Me-3-CF$_3$-pyrazol-5-yl | O | S | CF$_2$Br |
| 2-Cl-pyridin-4-yl | O | S | CF$_2$Br |
| 3-CF$_3$—Ph | O | S | CF$_2$I |
| 1-Me-3-CF$_3$-pyrazol-5-yl | O | S | CF$_2$I |
| 2-Cl-pyridin-4-yl | O | S | CF$_2$I |
| 2-Cl-pyridin-4-yl | O | S | OCH$_2$F |
| 2-Cl-pyridin-4-yl | O | S | OCHF$_2$ |
| 2-Cl-pyridin-4-yl | O | S | OCF$_3$ |
| 3-CF$_3$—Ph | O | S | CFMe$_2$ |
| 1-Me-3-CF$_3$-pyrazol-5-yl | O | S | CFMe$_2$ |
| 2-Cl-pyridin-4-yl | O | S | CFMe$_2$ |
| 3-CF$_3$—Ph | O | S | CH(CF$_3$)$_2$ |
| 1-Me-3-CF$_3$-pyrazol-5-yl | O | S | CH(CF$_3$)$_2$ |
| 2-Cl-pyridin-4-yl | O | S | CH(CF$_3$)$_2$ |
| 3-CF$_3$—Ph | O | S | CH(CF$_3$)Me |
| 1-Me-3-CF$_3$-pyrazol-5-yl | O | S | CH(CF$_3$)Me |
| 2-Cl-pyridin-4-yl | O | S | CH(CF$_3$)Me |
| 3-CF$_3$—Ph | O | S | CF$_2$Me |
| 1-Me-3-CF$_3$-pyrazol-5-yl | O | S | CF$_2$Me |
| 2-Cl-pyridin-4-yl | O | S | CF$_2$Me |
| 3-CF$_3$—Ph | O | S | CHFMe |
| 1-Me-3-CF$_3$-pyrazol-5-yl | O | S | CHFMe |
| 2-Cl-pyridin-4-yl | O | S | CHFMe |
| 3-CF$_3$—Ph | O | S | 2-F—Pr-cyc |
| 1-Me-3-CF$_3$-pyrazol-5-yl | O | S | 2-F—Pr-cyc |
| 2-Cl-pyridin-4-yl | O | S | 2-F—Pr-cyc |
| 3-CF$_3$—Ph | O | S | 2,2-F$_2$—Pr-cyc |
| 1-Me-3-CF$_3$-pyrazol-5-yl | O | S | 2,2-F$_2$—Pr-cyc |
| 2-Cl-pyridin-4-yl | O | S | 2,2-F$_2$—Pr-cyc |
| 3-CF$_3$—Ph | O | S | 2,2,3,3-F$_4$—Pr-cyc |
| 1-Me-3-CF$_3$-pyrazol-5-yl | O | S | 2,2,3,3-F$_4$—Pr-cyc |
| 2-Cl-pyridin-4-yl | O | S | 2,2,3,3-F$_4$—Pr-cyc |
| 3-CF$_3$—Ph | O | S | 2-Cl—Pr-cyc |
| 1-Me-3-CF$_3$-pyrazol-5-yl | O | S | 2-Cl—Pr-cyc |
| 2-Cl-pyridin-4-yl | O | S | 2-Cl—Pr-cyc |
| 3-CF$_3$—Ph | O | S | 2,2-Cl$_2$—Pr-cyc |
| 1-Me-3-CF$_3$-pyrazol-5-yl | O | S | 2,2-Cl$_2$—Pr-cyc |
| 2-Cl-pyridin-4-yl | O | S | 2,2-Cl$_2$—Pr-cyc |
| 3-CF$_3$—Ph | O | S | CH=CF$_2$ |
| 1-Me-3-CF$_3$-pyrazol-5-yl | O | S | CH=CF$_2$ |
| 2-Cl-pyridin-4-yl | O | S | CH=CF$_2$ |
| 2-Cl-pyridin-4-yl | O | NMe | CF$_3$ |
| 2-Cl-pyridin-4-yl | O | NMe | CF$_2$CF$_3$ |
| 3-CF$_3$—Ph | O | NMe | CH$_2$CF$_3$ |
| 1-Me-3-CF$_3$-pyrazol-5-yl | O | NMe | CH$_2$CF$_3$ |
| 2-Cl-pyridin-4-yl | O | NMe | CH$_2$CF$_3$ |
| 3-CF$_3$—Ph | O | NMe | CF$_2$Me |
| 1-Me-3-CF$_3$-pyrazol-5-yl | O | NMe | CF$_2$Me |
| 2-Cl-pyridin-4-yl | O | NMe | CF$_2$Me |
| 2-Cl-pyridin-4-yl | O | NMe | Et |
| 3-CF$_3$—Ph | O | NMe | Pr-iso |
| 1-Me-3-CF$_3$-pyrazol-5-yl | O | NMe | Pr-iso |
| 2-Cl-pyridin-4-yl | O | NMe | Pr-iso |
| 3-CF$_3$—Ph | O | NMe | Pr-cyc |
| 1-Me-3-CF$_3$-pyrazol-5-yl | O | NMe | Pr-cyc |
| 2-Cl-pyridin-4-yl | O | NMe | Pr-cyc |
| 3-CF$_3$—Ph | O | NCH$_2$CF$_3$ | H |

TABLE 2-continued

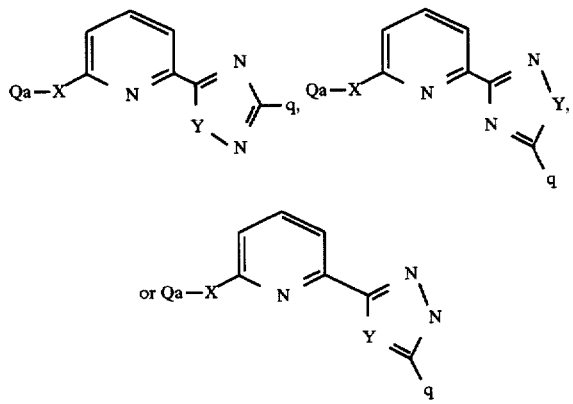

| Qa | X | Y | q |
|---|---|---|---|
| 1-Me-3-CF$_3$-pyrazol-5-yl | O | NCH$_2$CF$_3$ | H |
| 2-Cl-pyridin-4-yl | O | NCH$_2$CF$_3$ | H |
| 3-CF$_3$—Ph | O | NPr-cyc | H |
| 1-Me-3-CF$_3$-pyrazol-5-yl | O | NPr-cyc | H |
| 2-Cl-pyridin-4-yl | O | NPr-cyc | H |
| 3-CF$_3$—Ph | O | NPr-iso | H |
| 1-Me-3-CF$_3$-pyrazol-5-yl | O | NPr-iso | H |
| 2-Cl-pyridin-4-yl | O | NPr-iso | H |

TABLE 3

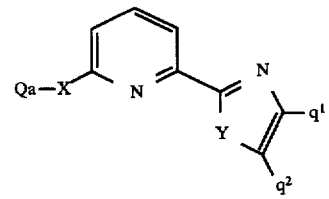

| Qa | X | Y | q$^1$ | q$^2$ |
|---|---|---|---|---|
| 2-CF$_3$—Ph | O | O | H | CF$_3$ |
| 3-CF$_3$—Ph | O | O | H | CF$_3$ |
| 4-CF$_3$—Ph | O | O | H | CF$_3$ |
| 2-Me—Ph | O | O | H | CF$_3$ |
| 3-Me—Ph | O | O | H | CF$_3$ |
| 4-Me—Ph | O | O | H | CF$_3$ |
| 2-Et—Ph | O | O | H | CF$_3$ |
| 3-Et—Ph | O | O | H | CF$_3$ |
| 4-Et—Ph | O | O | H | CF$_3$ |
| 2-MeO—Ph | O | O | H | CF$_3$ |
| 3-MeO—Ph | O | O | H | CF$_3$ |
| 4-MeO—Ph | O | O | H | CF$_3$ |
| 2-CN—Ph | O | O | H | CF$_3$ |
| 3-CN—Ph | O | O | H | CF$_3$ |
| 4-CN—Ph | O | O | H | CF$_3$ |
| 2-NO$_2$—Ph | O | O | H | CF$_3$ |
| 3-NO$_2$—Ph | O | O | H | CF$_3$ |
| 4-NO$_2$—Ph | O | O | H | CF$_3$ |
| 2-F—Ph | O | O | H | CF$_3$ |
| 3-F—Ph | O | O | H | CF$_3$ |
| 4-F—Ph | O | O | H | CF$_3$ |
| 2-Cl—Ph | O | O | H | CF$_3$ |
| 3-Cl—Ph | O | O | H | CF$_3$ |
| 4-Cl—Ph | O | O | H | CF$_3$ |
| 2-Br—Ph | O | O | H | CF$_3$ |
| 3-Br—Ph | O | O | H | CF$_3$ |
| 4-Br—Ph | O | O | H | CF$_3$ |
| 2-I—Ph | O | O | H | CF$_3$ |
| 3-I—Ph | O | O | H | CF$_3$ |
| 4-I—Ph | O | O | H | CF$_3$ |
| 1-Me-3-CF$_3$-pyrazol-5-yl | O | O | H | CF$_3$ |
| 1-Me-3-CF$_3$CF$_2$-pyrazol-5-yl | O | O | H | CF$_3$ |
| 1-Me-3-CF$_3$CF$_2$CF$_2$-pyrazol-5-yl | O | O | H | CF$_3$ |
| 1-Me-pyrazol-5-yl | O | O | H | CF$_3$ |
| 1-Me-3-Me-pyrazol-5-yl | O | O | H | CF$_3$ |
| 1-Me-3-Et-pyrazol-5-yl | O | O | H | CF$_3$ |
| 1-Me-3-Pr-n-pyrazol-5-yl | O | O | H | CF$_3$ |
| 1-Me-3-CH$_2$F-pyrazol-5-yl | O | O | H | CF$_3$ |
| 1-Me-3-CHF$_2$-pyrazol-5-yl | O | O | H | CF$_3$ |
| 1-Me-3-CO$_2$Me-pyrazol-5-yl | O | O | H | CF$_3$ |
| 1-Me-3-CN-pyrazol-5-yl | O | O | H | CF$_3$ |
| 1-Me-3-NO$_2$-pyrazol-5-yl | O | O | H | CF$_3$ |
| 1-Me-3-F-pyrazol-5-yl | O | O | H | CF$_3$ |
| 1-Me-3-Cl-pyrazol-5-yl | O | O | H | CF$_3$ |
| 1-Me-3-Br-pyrazol-5-yl | O | O | H | CF$_3$ |
| 1-Me-3-I-pyrazol-5-yl | O | O | H | CF$_3$ |
| 1-Me-3-CF$_3$-4-Cl-pyrazol-5-yl | O | O | H | CF$_3$ |
| 1-Me-3-CF$_3$-4-Br-pyrazol-5-yl | O | O | H | CF$_3$ |
| 1-Et-3-CF$_3$-pyrazol-5-yl | O | O | H | CF$_3$ |
| 1-Et-3-CF$_3$CF$_2$-pyrazol-5-yl | O | O | H | CF$_3$ |
| 1-Et-3-CF$_3$CF$_2$CF$_2$-pyrazol-5-yl | O | O | H | CF$_3$ |
| 1-Et-pyrazol-5-yl | O | O | H | CF$_3$ |
| 1-Et-3-Me-pyrazol-5-yl | O | O | H | CF$_3$ |
| 1-Et-3-Et-pyrazol-5-yl | O | O | H | CF$_3$ |
| 1-Et-3-Pr-n-pyrazol-5-yl | O | O | H | CF$_3$ |
| 1-Et-3-CH$_2$F-pyrazol-5-yl | O | O | H | CF$_3$ |
| 1-Et-3-CHF$_2$-pyrazol-5-yl | O | O | H | CF$_3$ |
| 1-Et-3-CO$_2$Me-pyrazol-5-yl | O | O | H | CF$_3$ |
| 1-Et-3-CN-pyrazol-5-yl | O | O | H | CF$_3$ |
| 1-Et-3-NO$_2$-pyrazol-5-yl | O | O | H | CF$_3$ |
| 1-Et-3-F-pyrazol-5-yl | O | O | H | CF$_3$ |
| 1-Et-3-Cl-pyrazol-5-yl | O | O | H | CF$_3$ |

TABLE 3-continued

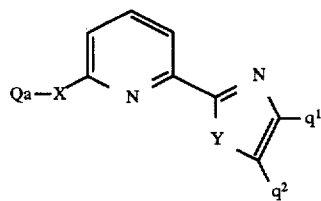

| Qa | X | Y | q¹ | q² |
|---|---|---|---|---|
| 1-Et-3-Br-pyrazol-5-yl | O | O | H | $CF_3$ |
| 1-Et-3-I-pyrazol-5-yl | O | O | H | $CF_3$ |
| 1-Et-3-$CF_3$-4-Cl-pyrazol-5-yl | O | O | H | $CF_3$ |
| 1-Et-3-$CF_3$-4-Br-pyrazol-5-yl | O | O | H | $CF_3$ |
| 1-Me-5-$CF_3$-pyrazol-3-yl | O | O | H | $CF_3$ |
| 1-Me-5-$CF_3CF_2$-pyrazol-3-yl | O | O | H | $CF_3$ |
| 1-Me-5-$CF_3CF_2CF_2$-pyrazol-3-yl | O | O | H | $CF_3$ |
| 1-Me-pyrazol-3-yl | O | O | H | $CF_3$ |
| 1-Me-5-Me-pyrazol-3-yl | O | O | H | $CF_3$ |
| 1-Me-5-Et-pyrazol-3-yl | O | O | H | $CF_3$ |
| 1-Me-5-Pr-n-pyrazol-3-yl | O | O | H | $CF_3$ |
| 1-Me-5-$CH_2F$-pyrazol-3-yl | O | O | H | $CF_3$ |
| 1-Me-5-$CHF_2$-pyrazol-3-yl | O | O | H | $CF_3$ |
| 1-Me-5-$CO_2Me$-pyrazol-3-yl | O | O | H | $CF_3$ |
| 1-Me-5-CN-pyrazol-3-yl | O | O | H | $CF_3$ |
| 1-Me-5-$NO_2$-pyrazol-3-yl | O | O | H | $CF_3$ |
| 1-Me-5-F-pyrazol-3-yl | O | O | H | $CF_3$ |
| 1-Me-5-Cl-pyrazol-3-yl | O | O | H | $CF_3$ |
| 1-Me-5-Br-pyrazol-3-yl | O | O | H | $CF_3$ |
| 1-Me-5-I-pyrazol-3-yl | O | O | H | $CF_3$ |
| 1-Me-5-$CF_3$-4-Cl-pyrazol-3-yl | O | O | H | $CF_3$ |
| 1-Me-5-$CF_3$-4-Br-pyrazol-3-yl | O | O | H | $CF_3$ |
| 2-$CF_3$—Ph | O | O | $CF_3$ | H |
| 3-$CF_3$—Ph | O | O | $CF_3$ | H |
| 4-$CF_3$—Ph | O | O | $CF_3$ | H |
| 2-Me—Ph | O | O | $CF_3$ | H |
| 3-Me—Ph | O | O | $CF_3$ | H |
| 4-Me—Ph | O | O | $CF_3$ | H |
| 2-Et—Ph | O | O | $CF_3$ | H |
| 3-Et—Ph | O | O | $CF_3$ | H |
| 4-Et—Ph | O | O | $CF_3$ | H |
| 2-MeO—Ph | O | O | $CF_3$ | H |
| 3-MeO—Ph | O | O | $CF_3$ | H |
| 4-MeO—Ph | O | O | $CF_3$ | H |
| 2-CN—Ph | O | O | $CF_3$ | H |
| 3-CN—Ph | O | O | $CF_3$ | H |
| 4-CN—Ph | O | O | $CF_3$ | H |
| 2-$NO_2$—Ph | O | O | $CF_3$ | H |
| 3-$NO_2$—Ph | O | O | $CF_3$ | H |
| 4-$NO_2$—Ph | O | O | $CF_3$ | H |
| 2-F—Ph | O | O | $CF_3$ | H |
| 3-F—Ph | O | O | $CF_3$ | H |
| 4-F—Ph | O | O | $CF_3$ | H |
| 2-Cl—Ph | O | O | $CF_3$ | H |
| 3-Cl—Ph | O | O | $CF_3$ | H |
| 4-Cl—Ph | O | O | $CF_3$ | H |
| 2-Br—Ph | O | O | $CF_3$ | H |
| 3-Br—Ph | O | O | $CF_3$ | H |
| 4-Br—Ph | O | O | $CF_3$ | H |
| 2-I—Ph | O | O | $CF_3$ | H |
| 3-I—Ph | O | O | $CF_3$ | H |
| 4-I—Ph | O | O | $CF_3$ | H |
| 1-Me-3-$CF_3$-pyrazol-5-yl | O | O | $CF_3$ | H |
| 1-Me-3-$CF_3CF_2$-pyrazol-5-yl | O | O | $CF_3$ | H |
| 1-Me-3-$CF_3CF_2CF_2$-pyrazol-5-yl | O | O | $CF_3$ | H |
| 1-Me-pyrazol-5-yl | O | O | $CF_3$ | H |
| 1-Me-3-Me-pyrazol-5-yl | O | O | $CF_3$ | H |
| 1-Me-3-Et-pyrazol-5-yl | O | O | $CF_3$ | H |
| 1-Me-3-Pr-n-pyrazol-5-yl | O | O | $CF_3$ | H |
| 1-Me-3-$CH_2F$-pyrazol-5-yl | O | O | $CF_3$ | H |
| 1-Me-3-$CHF_2$-pyrazol-5-yl | O | O | $CF_3$ | H |
| 1-Me-3-$CO_2Me$-pyrazol-5-yl | O | O | $CF_3$ | H |
| 1-Me-3-CN-pyrazol-5-yl | O | O | $CF_3$ | H |
| 1-Me-3-$NO_2$-pyrazol-5-yl | O | O | $CF_3$ | H |
| 1-Me-3-F-pyrazol-5-yl | O | O | $CF_3$ | H |
| 1-Me-3-Cl-pyrazol-5-yl | O | O | $CF_3$ | H |
| 1-Me-3-Br-pyrazol-5-yl | O | O | $CF_3$ | H |

TABLE 3-continued

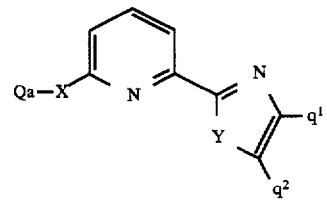

| Qa | X | Y | q¹ | q² |
|---|---|---|---|---|
| 1-Me-3-I-pyrazol-5-yl | O | O | $CF_3$ | H |
| 1-Me-3-$CF_3$-4-Cl-pyrazol-5-yl | O | O | $CF_3$ | H |
| 1-Me-3-$CF_3$-4-Br-pyrazol-5-yl | O | O | $CF_3$ | H |
| 1-Et-3-$CF_3$-pyrazol-5-yl | O | O | $CF_3$ | H |
| 1-Et-3-$CF_3CF_2$-pyrazol-5-yl | O | O | $CF_3$ | H |
| 1-Et-3-$CF_3CF_2CF_2$-pyrazol-5-yl | O | O | $CF_3$ | H |
| 1-Et-pyrazol-5-yl | O | O | $CF_3$ | H |
| 1-Et-3-Me-pyrazol-5-yl | O | O | $CF_3$ | H |
| 1-Et-3-Et-pyrazol-5-yl | O | O | $CF_3$ | H |
| 1-Et-3-Pr-n-pyrazol-5-yl | O | O | $CF_3$ | H |
| 1-Et-3-$CH_2F$-pyrazol-5-yl | O | O | $CF_3$ | H |
| 1-Et-3-$CHF_2$-pyrazol-5-yl | O | O | $CF_3$ | H |
| 1-Et-3-$CO_2Me$-pyrazol-5-yl | O | O | $CF_3$ | H |
| 1-Et-3-CN-pyrazol-5-yl | O | O | $CF_3$ | H |
| 1-Et-3-$NO_2$-pyrazol-5-yl | O | O | $CF_3$ | H |
| 1-Et-3-F-pyrazol-5-yl | O | O | $CF_3$ | H |
| 1-Et-3-Cl-pyrazol-5-yl | O | O | $CF_3$ | H |
| 1-Et-3-Br-pyrazol-5-yl | O | O | $CF_3$ | H |
| 1-Et-3-I-pyrazol-5-yl | O | O | $CF_3$ | H |
| 1-Et-3-$CF_3$-4-Cl-pyrazol-5-yl | O | O | $CF_3$ | H |
| 1-Et-3-$CF_3$-4-Br-pyrazol-5-yl | O | O | $CF_3$ | H |
| 1-Me-5-$CF_3$-pyrazol-3-yl | O | O | $CF_3$ | H |
| 1-Me-5-$CF_3CF_2$-pyrazol-3-yl | O | O | $CF_3$ | H |
| 1-Me-5-$CF_3CF_2CF_2$-pyrazol-3-yl | O | O | $CF_3$ | H |
| 1-Me-pyrazol-3-yl | O | O | $CF_3$ | H |
| 1-Me-5-Me-pyrazol-3-yl | O | O | $CF_3$ | H |
| 1-Me-5-Et-pyrazol-3-yl | O | O | $CF_3$ | H |
| 1-Me-5-Pr-n-pyrazol-3-yl | O | O | $CF_3$ | H |
| 1-Me-5-$CH_2F$-pyrazol-3-yl | O | O | $CF_3$ | H |
| 1-Me-5-$CHF_2$-pyrazol-3-yl | O | O | $CF_3$ | H |
| 1-Me-5-$CO_2Me$-pyrazol-3-yl | O | O | $CF_3$ | H |
| 1-Me-5-CN-pyrazol-3-yl | O | O | $CF_3$ | H |
| 1-Me-5-$NO_2$-pyrazol-3-yl | O | O | $CF_3$ | H |
| 1-Me-5-F-pyrazol-3-yl | O | O | $CF_3$ | H |
| 1-Me-5-Cl-pyrazol-3-yl | O | O | $CF_3$ | H |
| 1-Me-5-Br-pyrazol-3-yl | O | O | $CF_3$ | H |
| 1-Me-5-I-pyrazol-3-yl | O | O | $CF_3$ | H |
| 1-Me-5-$CF_3$-4-Cl-pyrazol-3-yl | O | O | $CF_3$ | H |
| 1-Me-5-$CF_3$-4-Br-pyrazol-3-yl | O | O | $CF_3$ | H |
| 2-$CF_3$—Ph | O | O | H | H |
| 3-$CF_3$—Ph | O | O | H | H |
| 1-Me-3-$CF_3$-pyrazol-5-yl | O | O | H | H |
| 1-Me-5-$CF_3$-pyrazol-3-yl | O | O | H | H |
| 2-$CF_3$—Ph | O | O | H | Me |
| 3-$CF_3$—Ph | O | O | H | Me |
| 1-Me-3-$CF_3$-pyrazol-5-yl | O | O | H | Me |
| 1-Me-5-$CF_3$-pyrazol-3-yl | O | O | H | Me |
| 2-$CF_3$—Ph | O | O | Me | H |
| 3-$CF_3$—Ph | O | O | Me | H |
| 1-Me-3-$CF_3$-pyrazol-5-yl | O | O | Me | H |
| 1-Me-5-$CF_3$-pyrazol-3-yl | O | O | Me | H |
| 2-$CF_3$—Ph | O | O | Me | Me |
| 3-$CF_3$—Ph | O | O | Me | Me |
| 1-Me-3-$CF_3$-pyrazol-5-yl | O | O | Me | Me |
| 1-Me-5-$CF_3$-pyrazol-3-yl | O | O | Me | Me |
| 2-$CF_3$—Ph | O | O | H | Et |
| 3-$CF_3$—Ph | O | O | H | Et |
| 1-Me-3-$CF_3$-pyrazol-5-yl | O | O | H | Et |
| 1-Me-5-$CF_3$-pyrazol-3-yl | O | O | H | Et |
| 2-$CF_3$—Ph | O | O | Et | H |
| 3-$CF_3$—Ph | O | O | Et | H |
| 1-Me-3-$CF_3$-pyrazol-5-yl | O | O | Et | H |
| 1-Me-5-$CF_3$-pyrazol-3-yl | O | O | Et | H |
| 2-$CF_3$—Ph | O | O | H | $CF_2CF_3$ |
| 3-$CF_3$—Ph | O | O | H | $CF_2CF_3$ |
| 1-Me-3-$CF_3$-pyrazol-5-yl | O | O | H | $CF_2CF_3$ |
| 1-Me-5-$CF_3$-pyrazol-3-yl | O | O | H | $CF_2CF_3$ |

TABLE 3-continued

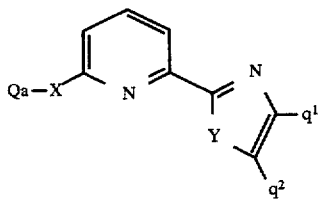

| Qa | X | Y | q¹ | q² |
|---|---|---|---|---|
| 2-CF$_3$—Ph | O | O | CF$_2$CF$_3$ | H |
| 3-CF$_3$—Ph | O | O | CF$_2$CF$_3$ | H |
| 1-Me-3-CF$_3$-pyrazol-5-yl | O | O | CF$_2$CF$_3$ | H |
| 1-Me-5-CF$_3$-pyrazol-3-yl | O | O | CF$_2$CF$_3$ | H |
| 2-CF$_3$—Ph | O | S | CF$_3$ | H |
| 3-CF$_3$—Ph | O | S | CF$_3$ | H |
| 1-Me-3-CF$_3$-pyrazol-5-yl | O | S | CF$_3$ | H |
| 1-Me-5-CF$_3$-pyrazol-3-yl | O | S | CF$_3$ | H |
| 2-CF$_3$—Ph | O | S | H | CF$_3$ |
| 3-CF$_3$—Ph | O | S | H | CF$_3$ |
| 1-Me-3-CF$_3$-pyrazol-5-yl | O | S | H | CF$_3$ |
| 1-Me-5-CF$_3$-pyrazol-3-yl | O | S | H | CF$_3$ |
| 2-CF$_3$—Ph | O | NH | CF$_3$ | H |
| 3-CF$_3$—Ph | O | NH | CF$_3$ | H |
| 1-Me-3-CF$_3$-pyrazol-5-yl | O | NH | CF$_3$ | H |
| 1-Me-5-CF$_3$-pyrazol-3-yl | O | NH | CF$_3$ | H |
| 2-CF$_3$—Ph | O | NH | H | CF$_3$ |
| 3-CF$_3$—Ph | O | NH | H | CF$_3$ |
| 1-Me-3-CF$_3$-pyrazol-5-yl | O | NH | H | CF$_3$ |
| 1-Me-5-CF$_3$-pyrazol-3-yl | O | NH | H | CF$_3$ |
| 2-CF$_3$—Ph | O | NMe | CF$_3$ | H |
| 3-CF$_3$—Ph | O | NMe | CF$_3$ | H |
| 1-Me-3-CF$_3$-pyrazol-5-yl | O | NMe | CF$_3$ | H |
| 1-Me-5-CF$_3$-pyrazol-3-yl | O | NMe | CF$_3$ | H |
| 2-CF$_3$—Ph | O | NMe | H | CF$_3$ |
| 3-CF$_3$—Ph | O | NMe | H | CF$_3$ |
| 1-Me-3-CF$_3$-pyrazol-5-yl | O | NMe | H | CF$_3$ |
| 1-Me-5-CF$_3$-pyrazol-3-yl | O | NMe | H | CF$_3$ |
| 2-CF$_3$—Ph | S | O | CF$_3$ | H |
| 3-CF$_3$—Ph | S | O | CF$_3$ | H |
| 1-Me-3-CF$_3$-pyrazol-5-yl | S | O | CF$_3$ | H |
| 1-Me-5-CF$_3$-pyrazol-3-yl | S | O | CF$_3$ | H |
| 2-CF$_3$—Ph | S | O | H | CF$_3$ |
| 3-CF$_3$—Ph | S | O | H | CF$_3$ |
| 1-Me-3-CF$_3$-pyrazol-5-yl | S | O | H | CF$_3$ |
| 1-Me-5-CF$_3$-pyrazol-3-yl | S | O | H | CF$_3$ |
| 2-CF$_3$—Ph | NH | O | CF$_3$ | H |
| 3-CF$_3$—Ph | NH | O | CF$_3$ | H |
| 1-Me-3-CF$_3$-pyrazol-5-yl | NH | O | CF$_3$ | H |
| 1-Me-5-CF$_3$-pyrazol-3-yl | NH | O | CF$_3$ | H |
| 2-CF$_3$—Ph | NH | O | H | CF$_3$ |
| 3-CF$_3$—Ph | NH | O | H | CF$_3$ |
| 1-Me-3-CF$_3$-pyrazol-5-yl | NH | O | H | CF$_3$ |
| 1-Me-5-CF$_3$-pyrazol-3-yl | NH | O | H | CF$_3$ |
| 2-Cl-pyridin-4-yl | O | O | CF$_3$ | H |
| 2-Cl-pyridin-6-yl | O | O | CF$_3$ | H |
| 3-Cl-pyridin-5-yl | O | O | CF$_3$ | H |
| 3-Cl-pyridin-6-yl | O | O | CF$_3$ | H |
| 2-Cl-pyridin-4-yl | O | O | H | CF$_3$ |
| 2-Cl-pyridin-6-yl | O | O | H | CF$_3$ |
| 3-Cl-pyridin-5-yl | O | O | H | CF$_3$ |
| 3-Cl-pyridin-6-yl | O | O | H | CF$_3$ |
| 2-Cl-pyridin-4-yl | O | O | Me | H |
| 2-Cl-pyridin-6-yl | O | O | Me | H |
| 3-Cl-pyridin-5-yl | O | O | Me | H |
| 3-Cl-pyridin-6-yl | O | O | Me | H |
| 2-Cl-pyridin-4-yl | O | O | H | Me |
| 2-Cl-pyridin-6-yl | O | O | H | Me |
| 3-Cl-pyridin-5-yl | O | O | H | Me |
| 3-Cl-pyridin-6-yl | O | O | H | Me |
| 2-CF$_3$—Ph | O | S | CF$_2$CF$_3$ | H |
| 3-CF$_3$—Ph | O | S | CF$_2$CF$_3$ | H |
| 4-CF$_3$—Ph | O | S | CF$_2$CF$_3$ | H |
| 2-CF$_3$—Ph | O | S | H | CF$_2$CF$_3$ |
| 3-CF$_3$—Ph | O | S | H | CF$_2$CF$_3$ |
| 4-CF$_3$—Ph | O | S | H | CF$_2$CF$_3$ |
| 2-Cl-pyridin-4-yl | O | O | H | Et |

TABLE 3-continued

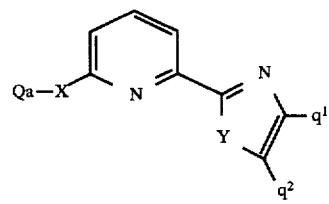

| Qa | X | Y | q¹ | q² |
|---|---|---|---|---|
| 2-Cl-pyridin-4-yl | O | O | Et | H |
| 2-Cl-pyridin-4-yl | O | O | H | CF$_2$CF$_3$ |
| 2-Cl-pyridin-4-yl | O | O | CF$_2$CF$_3$ | H |
| 3-CF$_3$—Ph | O | O | CH$_2$CF$_3$ | H |
| 1-Me-3-CF$_3$-pyrazol-5-yl | O | O | CH$_2$CF$_3$ | H |
| 2-Cl-pyridin-4-yl | O | O | CH$_2$CF$_3$ | H |
| 3-CF$_3$—Ph | O | O | H | CH$_2$CF$_3$ |
| 1-Me-3-CF$_3$-pyrazol-5-yl | O | O | H | CH$_2$CF$_3$ |
| 2-Cl-pyridin-4-yl | O | O | H | CH$_2$CF$_3$ |
| 3-CF$_3$—Ph | O | O | CF$_2$Me | H |
| 1-Me-3-CF$_3$-pyrazol-5-yl | O | O | CF$_2$Me | H |
| 2-Cl-pyridin-4-yl | O | O | CF$_2$Me | H |
| 3-CF$_3$—Ph | O | O | H | CF$_2$Me |
| 1-Me-3-CF$_3$-pyrazol-5-yl | O | O | H | CF$_2$Me |
| 2-Cl-pyridin-4-yl | O | O | H | CF$_2$Me |
| 3-CF$_3$—Ph | O | O | Pr-iso | H |
| 1-Me-3-CF$_3$-pyrazol-5-yl | O | O | Pr-iso | H |
| 2-Cl-pyridin-4-yl | O | O | Pr-iso | H |
| 3-CF$_3$—Ph | O | O | H | Pr-iso |
| 1-Me-3-CF$_3$-pyrazol-5-yl | O | O | H | Pr-iso |
| 2-Cl-pyridin-4-yl | O | O | H | Pr-iso |
| 3-CF$_3$—Ph | O | O | Pr-cyc | H |
| 1-Me-3-CF$_3$-pyrazol-5-yl | O | O | Pr-cyc | H |
| 2-Cl-pyridin-4-yl | O | O | Pr-cyc | H |
| 3-CF$_3$—Ph | O | O | H | Pr-cyc |
| 1-Me-3-CF$_3$-pyrazol-5-yl | O | O | H | Pr-cyc |
| 2-Cl-pyridin-4-yl | O | O | H | Pr-cyc |
| 3-CF$_3$—Ph | O | S | Me | H |
| 1-Me-3-CF$_3$-pyrazol-5-yl | O | S | Me | H |
| 2-Cl-pyridin-4-yl | O | S | Me | H |
| 3-CF$_3$—Ph | O | S | H | Me |
| 1-Me-3-CF$_3$-pyrazol-5-yl | O | S | H | Me |
| 2-Cl-pyridin-4-yl | O | S | H | Me |
| 3-CF$_3$—Ph | O | S | Et | H |
| 1-Me-3-CF$_3$-pyrazol-5-yl | O | S | Et | H |
| 2-Cl-pyridin-4-yl | O | S | Et | H |
| 3-CF$_3$—Ph | O | S | H | Et |
| 1-Me-3-CF$_3$-pyrazol-5-yl | O | S | H | Et |
| 2-Cl-pyridin-4-yl | O | S | H | Et |
| 2-Cl-pyridin-4-yl | O | S | CF$_3$ | H |
| 2-Cl-pyridin-4-yl | O | S | H | CF$_3$ |
| 2-Cl-pyridin-4-yl | O | S | CF$_2$CF$_3$ | H |
| 2-Cl-pyridin-4-yl | O | S | H | CF$_2$CF$_3$ |
| 3-CF$_3$-Ph | O | S | CH$_2$CF$_3$ | H |
| 1-Me-3-CF$_3$-pyrazol-5-yl | O | S | CH$_2$CF$_3$ | H |
| 2-Cl-pyridin-4-yl | O | S | CH$_2$CF$_3$ | H |
| 3-CF$_3$—Ph | O | S | H | CH$_2$CF$_3$ |
| 1-Me-3-CF$_3$-pyrazol-5-yl | O | S | H | CH$_2$CF$_3$ |
| 2-Cl-pyridin-4-yl | O | S | H | CH$_2$CF$_3$ |
| 3-CF$_3$—Ph | O | S | CF$_2$Me | H |
| 1-Me-3-CF$_3$-pyrazol-5-yl | O | S | CF$_2$Me | H |
| 2-Cl-pyridin-4-yl | O | S | CF$_2$Me | H |
| 3-CF$_3$—Ph | O | S | H | CF$_2$Me |
| 1-Me-3-CF$_3$-pyrazol-5-yl | O | S | H | CF$_2$Me |
| 2-Cl-pyridin-4-yl | O | S | H | CF$_2$Me |

TABLE 4

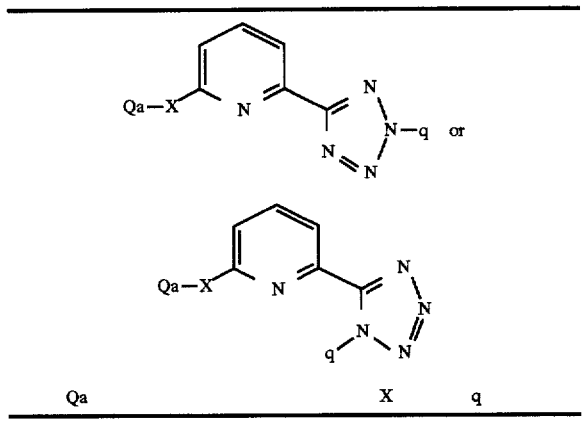

| Qa | X | q |
|---|---|---|
| 2-CF₃—Ph | O | H |
| 3-CF₃—Ph | O | H |
| 4-CF₃—Ph | O | H |
| 2-Me—Ph | O | H |
| 3-Me—Ph | O | H |
| 4-Me—Ph | O | H |
| 2-Et—Ph | O | H |
| 3-Et—Ph | O | H |
| 4-Et—Ph | O | H |
| 2-MeO—Ph | O | H |
| 3-MeO—Ph | O | H |
| 4-MeO—Ph | O | H |
| 2-CN—Ph | O | H |
| 3-CN—Ph | O | H |
| 4-CN—Ph | O | H |
| 2-NO₂—Ph | O | H |
| 3-NO₂—Ph | O | H |
| 4-NO₂—Ph | O | H |
| 2-F—Ph | O | H |
| 3-F—Ph | O | H |
| 4-F—Ph | O | H |
| 2-Cl—Ph | O | H |
| 3-Cl—Ph | O | H |
| 4-Cl—Ph | O | H |
| 2-Br—Ph | O | H |
| 3-Br—Ph | O | H |
| 4-Br—Ph | O | H |
| 2-I—Ph | O | H |
| 3-I—Ph | O | H |
| 4-I—Ph | O | H |
| 1-Me-3-CF₃-pyrazol-5-yl | O | H |
| 1-Me-3-CF₃CF₂-pyrazol-5-yl | O | H |
| 1-Me-3-CF₃CF₂CF₂-pyrazol-5-yl | O | H |
| 1-Me-pyrazol-5-yl | O | H |
| 1-Me-3-Me-pyrazol-5-yl | O | H |
| 1-Me-3-Et-pyrazol-5-yl | O | H |
| 1-Me-3-Pr-n-pyrazol-5-yl | O | H |
| 1-Me-3-CH₂F-pyrazol-5-yl | O | H |
| 1-Me-3-CHF₂-pyrazol-5-yl | O | H |
| 1-Me-3-CO₂Me-pyrazol-5-yl | O | H |
| 1-Me-3-CN-pyrazol-5-yl | O | H |
| 1-Me-3-NO₂-pyrazol-5-yl | O | H |
| 1-Me-3-F-pyrazol-5-yl | O | H |
| 1-Me-3-Cl-pyrazol-5-yl | O | H |
| 1-Me-3-Br-pyrazol-5-yl | O | H |
| 1-Me-3-I-pyrazol-5-yl | O | H |
| 1-Me-3-CF₃-4-Cl-pyrazol-5-yl | O | H |
| 1-Me-3-CF₃-4-Br-pyrazol-5-yl | O | H |
| 1-Et-3-CF₃-pyrazol-5-yl | O | H |
| 1-Et-3-CF₃CF₂-pyrazol-5-yl | O | H |
| 1-Et-3-CF₃CF₂CF₂-pyrazol-5-yl | O | H |
| 1-Et-pyrazol-5-yl | O | H |
| 1-Et-3-Me-pyrazol-5-yl | O | H |
| 1-Et-3-Et-pyrazol-5-yl | O | H |
| 1-Et-3-Pr-n-pyrazol-5-yl | O | H |
| 1-Et-3-CH₂F-pyrazol-5-yl | O | H |
| 1-Et-3-CHF₂-pyrazol-5-yl | O | H |
| 1-Et-3-CO₂Me-pyrazol-5-yl | O | H |
| 1-Et-3-CN-pyrazol-5-yl | O | H |

TABLE 4-continued

| Qa | X | q |
|---|---|---|
| 1-Et-3-NO₂-pyrazol-5-yl | O | H |
| 1-Et-3-F-pyrazol-5-yl | O | H |
| 1-Et-3-Cl-pyrazol-5-yl | O | H |
| 1-Et-3-Br-pyrazol-5-yl | O | H |
| 1-Et-3-I-pyrazol-5-yl | O | H |
| 1-Et-3-CF₃-4-Cl-pyrazol-5-yl | O | H |
| 1-Et-3-CF₃-4-Br-pyrazol-5-yl | O | H |
| 1-Me-5-CF₃-pyrazol-3-yl | O | H |
| 1-Me-5-CF₃CF₂-pyrazol-3-yl | O | H |
| 1-Me-5-CF₃CF₂CF₂-pyrazol-3-yl | O | H |
| 1-Me-pyrazol-3-yl | O | H |
| 1-Me-5-Me-pyrazol-3-yl | O | H |
| 1-Me-5-Et-pyrazol-3-yl | O | H |
| 1-Me-5-Pr-n-pyrazol-3-yl | O | H |
| 1-Me-5-CH₂F-pyrazol-3-yl | O | H |
| 1-Me-5-CHF₂-pyrazol-3-yl | O | H |
| 1-Me-5-CO₂Me-pyrazol-3-yl | O | H |
| 1-Me-5-CN-pyrazol-3-yl | O | H |
| 1-Me-5-NO₂-pyrazol-3-yl | O | H |
| 1-Me-5-F-pyrazol-3-yl | O | H |
| 1-Me-5-Cl-pyrazol-3-yl | O | H |
| 1-Me-5-Br-pyrazol-3-yl | O | H |
| 1-Me-5-I-pyrazol-3-yl | O | H |
| 1-Me-5-CF₃-4-Cl-pyrazol-3-yl | O | H |
| 1-Me-5-CF₃-4-Br-pyrazol-3-yl | O | H |
| 2-CF₃—Ph | O | Me |
| 3-CF₃—Ph | O | Me |
| 4-CF₃—Ph | O | Me |
| 2-Me—Ph | O | Me |
| 3-Me—Ph | O | Me |
| 4-Me—Ph | O | Me |
| 2-Et—Ph | O | Me |
| 3-Et—Ph | O | Me |
| 4-Et—Ph | O | Me |
| 2-MeO—Ph | O | Me |
| 3-MeO—Ph | O | Me |
| 4-MeO—Ph | O | Me |
| 2-CN—Ph | O | Me |
| 3-CN—Ph | O | Me |
| 4-CN—Ph | O | Me |
| 2-NO₂—Ph | O | Me |
| 3-NO₂—Ph | O | Me |
| 4-NO₂—Ph | O | Me |
| 2-F—Ph | O | Me |
| 3-F—Ph | O | Me |
| 4-F—Ph | O | Me |
| 2-Cl—Ph | O | Me |
| 3-Cl—Ph | O | Me |
| 4-Cl—Ph | O | Me |
| 2-Br—Ph | O | Me |
| 3-Br—Ph | O | Me |
| 4-Br—Ph | O | Me |
| 2-I—Ph | O | Me |
| 3-I—Ph | O | Me |
| 4-I—Ph | O | Me |
| 1-Me-3-CF₃-pyrazol-5-yl | O | Me |
| 1-Me-3-CF₃CF₂-pyrazol-5-yl | O | Me |
| 1-Me-3-CF₃CF₂CF₂-pyrazol-5-yl | O | Me |
| 1-Me-pyrazol-5-yl | O | Me |

TABLE 4-continued

| Qa | X | q |
|---|---|---|
| 1-Me-3-Me-pyrazol-5-yl | O | Me |
| 1-Me-3-Et-pyrazol-5-yl | O | Me |
| 1-Me-3-Pr-n-pyrazol-5-yl | O | Me |
| 1-Me-3-CH$_2$F-pyrazol-5-yl | O | Me |
| 1-Me-3-CHF$_2$-pyrazol-5-yl | O | Me |
| 1-Me-3-CO$_2$Me-pyrazol-5-yl | O | Me |
| 1-Me-3-CN-pyrazol-5-yl | O | Me |
| 1-Me-3-NO$_2$-pyrazol-5-yl | O | Me |
| 1-Me-3-F-pyrazol-5-yl | O | Me |
| 1-Me-3-Cl-pyrazol-5-yl | O | Me |
| 1-Me-3-Br-pyrazol-5-yl | O | Me |
| 1-Me-3-I-pyrazol-5-yl | O | Me |
| 1-Me-3-CF$_3$-4-Cl-pyrazol-5-yl | O | Me |
| 1-Me-3-CF$_3$-4-Br-pyrazol-5-yl | O | Me |
| 1-Et-3-CF$_3$-pyrazol-5-yl | O | Me |
| 1-Et-3-CF$_3$CF$_2$-pyrazol-5-yl | O | Me |
| 1-Et-3-CF$_3$CF$_2$CF$_2$-pyrazol-5-yl | O | Me |
| 1-Et-pyrazol-5-yl | O | Me |
| 1-Et-3-Me-pyrazol-5-yl | O | Me |
| 1-Et-3-Et-pyrazol-5-yl | O | Me |
| 1-Et-3-Pr-n-pyrazol-5-yl | O | Me |
| 1-Et-3-CH$_2$F-pyrazol-5-yl | O | Me |
| 1-Et-3-CHF$_2$-pyrazol-5-yl | O | Me |
| 1-Et-3-CO$_2$Me-pyrazol-5-yl | O | Me |
| 1-Et-3-CN-pyrazol-5-yl | O | Me |
| 1-Et-3-NO$_2$-pyrazol-5-yl | O | Me |
| 1-Et-3-F-pyrazol-5-yl | O | Me |
| 1-Et-3-Cl-pyrazol-5-yl | O | Me |
| 1-Et-3-Br-pyrazol-5-yl | O | Me |
| 1-Et-3-I-pyrazol-5-yl | O | Me |
| 1-Et-3-CF$_3$-4-Cl-pyrazol-5-yl | O | Me |
| 1-Et-3-CF$_3$-4-Br-pyrazol-5-yl | O | Me |
| 1-Me-5-CF$_3$-pyrazol-3-yl | O | Me |
| 1-Me-5-CF$_3$CF$_2$-pyrazol-3-yl | O | Me |
| 1-Me-5-CF$_3$CF$_2$CF$_2$-pyrazol-3-yl | O | Me |
| 1-Me-pyrazol-3-yl | O | Me |
| 1-Me-5-Me-pyrazol-3-yl | O | Me |
| 1-Me-5-Et-pyrazol-3-yl | O | Me |
| 1-Me-5-Pr-n-pyrazol-3-yl | O | Me |
| 1-Me-5-CH$_2$F-pyrazol-3-yl | O | Me |
| 1-Me-5-CHF$_2$-pyrazol-3-yl | O | Me |
| 1-Me-5-CO$_2$Me-pyrazol-3-yl | O | Me |
| 1-Me-5-CN-pyrazol-3-yl | O | Me |
| 1-Me-5-NO$_2$-pyrazol-3-yl | O | Me |
| 1-Me-5-F-pyrazol-3-yl | O | Me |
| 1-Me-5-Cl-pyrazol-3-yl | O | Me |
| 1-Me-5-Br-pyrazol-3-yl | O | Me |
| 1-Me-5-I-pyrazol-3-yl | O | Me |
| 1-Me-5-CF$_3$-4-Cl-pyrazol-3-yl | O | Me |
| 1-Me-5-CF$_3$-4-Br-pyrazol-3-yl | O | Me |
| 2-CF$_3$—Ph | O | Et |
| 3-CF$_3$—Ph | O | Et |
| 1-Me-3-CF$_3$-pyrazol-5-yl | O | Et |
| 1-Me-5-CF$_3$-pyrazol-3-yl | O | Et |
| 2-CF$_3$—Ph | O | Pr-n |
| 3-CF$_3$—Ph | O | Pr-n |
| 1-Me-3-CF$_3$-pyrazol-5-yl | O | Pr-n |
| 1-Me-5-CF$_3$-pyrazol-3-yl | O | Pr-n |
| 2-CF$_3$—Ph | O | Pr-iso |
| 3-CF$_3$—Ph | O | Pr-iso |
| 1-Me-3-CF$_3$-pyrazol-5-yl | O | Pr-iso |
| 1-Me-5-CF$_3$-pyrazol-3-yl | O | Pr-iso |
| 3-CF$_3$—Ph | O | Bu-n |
| 1-Me-3-CF$_3$-pyrazol-5-yl | O | Bu-n |
| 3-CF$_3$—Ph | O | Bu-iso |
| 1-Me-3-CF$_3$-pyrazol-5-yl | O | Bu-iso |
| 3-CF$_3$—Ph | O | Bu-sec |
| 1-Me-3-CF$_3$-pyrazol-5-yl | O | Bu-sec |
| 3-CF$_3$—Ph | O | Bu-ter |
| 1-Me-3-CF$_3$-pyrazol-5-yl | O | Bu-ter |
| 3-CF$_3$—Ph | O | Pen-n |
| 1-Me-3-CF$_3$-pyrazol-5-yl | O | Pen-n |
| 3-CF$_3$—Ph | O | Hex-n |
| 1-Me-3-CF$_3$-pyrazol-5-yl | O | Hex-n |
| 2-CF$_3$—Ph | S | Me |
| 3-CF$_3$—Ph | S | Me |
| 1-Me-3-CF$_3$-pyrazol-5-yl | S | Me |
| 1-Me-5-CF$_3$-pyrazol-3-yl | S | Me |
| 2-CF$_3$—Ph | NH | Me |
| 3-CF$_3$—Ph | NH | Me |
| 1-Me-3-CF$_3$-pyrazol-5-yl | NH | Me |
| 1-Me-5-CF$_3$-pyrazol-3-yl | NH | Me |
| 2-Cl-pyridin-4-yl | O | H |
| 2-Cl-pyridin-6-yl | O | H |
| 3-Cl-pyridin-5-yl | O | H |
| 3-Cl-pyridin-6-yl | O | H |
| 2-Cl-pyridin-4-yl | O | Me |
| 2-Cl-pyridin-6-yl | O | Me |
| 3-Cl-pyridin-5-yl | O | Me |
| 3-Cl-pyridin-6-yl | O | Me |

TABLE 5

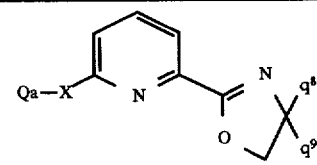

| Qa | X | q$^8$ | q$^9$ |
|---|---|---|---|
| 2-CF$_3$—Ph | O | H | H |
| 3-CF$_3$—Ph | O | H | H |
| 4-CF$_3$—Ph | O | H | H |
| 2-Me—Ph | O | H | H |
| 3-Me—Ph | O | H | H |
| 4-Me—Ph | O | H | H |
| 2-Et—Ph | O | H | H |
| 3-Et—Ph | O | H | H |
| 4-Et—Ph | O | H | H |
| 2-MeO—Ph | O | H | H |
| 3-MeO—Ph | O | H | H |
| 4-MeO—Ph | O | H | H |
| 2-CN—Ph | O | H | H |

TABLE 5-continued

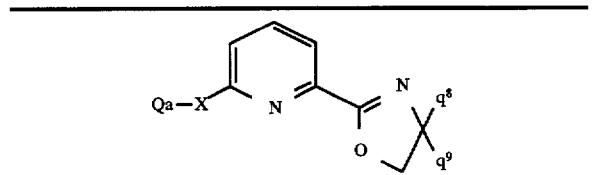

| Qa | X | q⁸ | q⁹ |
|---|---|---|---|
| 3-CN—Ph | O | H | H |
| 4-CN—Ph | O | H | H |
| 2-NO₂—Ph | O | H | H |
| 3-NO₂—Ph | O | H | H |
| 4-NO₂—Ph | O | H | H |
| 2-F—Ph | O | H | H |
| 3-F—Ph | O | H | H |
| 4-F—Ph | O | H | H |
| 2-Cl—Ph | O | H | H |
| 3-Cl—Ph | O | H | H |
| 4-Cl—Ph | O | H | H |
| 2-Br—Ph | O | H | H |
| 3-Br—Ph | O | H | H |
| 4-Br—Ph | O | H | H |
| 2-I—Ph | O | H | H |
| 3-I—Ph | O | H | H |
| 4-I—Ph | O | H | H |
| 1-Me-3-CF₃-pyrazol-5-yl | O | H | H |
| 1-Me-3-CF₃CF₂-pyrazol-5-yl | O | H | H |
| 1-Me-3-CF₃CF₂CF₂-pyrazol-5-yl | O | H | H |
| 1-Me-pyrazol-5-yl | O | H | H |
| 1-Me-3-Me-pyrazol-5-yl | O | H | H |
| 1-Me-3-Et-pyrazol-5-yl | O | H | H |
| 1-Me-3-Pr-n-pyrazol-5-yl | O | H | H |
| 1-Me-3-CH₂F-pyrazol-5-yl | O | H | H |
| 1-Me-3-CHF₂-pyrazol-5-yl | O | H | H |
| 1-Me-3-CO₂Me-pyrazol-5-yl | O | H | H |
| 1-Me-3-CN-pyrazol-5-yl | O | H | H |
| 1-Me-3-NO₂-pyrazol-5-yl | O | H | H |
| 1-Me-3-F-pyrazol-5-yl | O | H | H |
| 1-Me-3-Cl-pyrazol-5-yl | O | H | H |
| 1-Me-3-Br-pyrazol-5-yl | O | H | H |
| 1-Me-3-I-pyrazol-5-yl | O | H | H |
| 1-Me-3-CF₃-4-Cl-pyrazol-5-yl | O | H | H |
| 1-Me-3-CF₃-4-Br-pyrazol-5-yl | O | H | H |
| 1-Et-3-CF₃-pyrazol-5-yl | O | H | H |
| 1-Et-3-CF₃CF₂-pyrazol-5-yl | O | H | H |
| 1-Et-3-CF₃CF₂CF₂-pyrazol-5-yl | O | H | H |
| 1-Et-pyrazol-5-yl | O | H | H |
| 1-Et-3-Me-pyrazol-5-yl | O | H | H |
| 1-Et-3-Et-pyrazol-5-yl | O | H | H |
| 1-Et-3-Pr-n-pyrazol-5-yl | O | H | H |
| 1-Et-3-CH₂F-pyrazol-5-yl | O | H | H |
| 1-Et-3-CHF₂-pyrazol-5-yl | O | H | H |
| 1-Et-3-CO₂Me-pyrazol-5-yl | O | H | H |
| 1-Et-3-CN-pyrazol-5-yl | O | H | H |
| 1-Et-3-NO₂-pyrazol-5-yl | O | H | H |
| 1-Et-3-F-pyrazol-5-yl | O | H | H |
| 1-Et-3-Cl-pyrazol-5-yl | O | H | H |
| 1-Et-3-Br-pyrazol-5-yl | O | H | H |
| 1-Et-3-I-pyrazol-5-yl | O | H | H |
| 1-Et-3-CF₃-4-Cl-pyrazol-5-yl | O | H | H |
| 1-Et-3-CF₃-4-Br-pyrazol-5-yl | O | H | H |
| 1-Me-5-CF₃-pyrazol-3-yl | O | H | H |
| 1-Me-5-CF₃CF₂-pyrazol-3-yl | O | H | H |
| 1-Me-5-CF₃CF₂CF₂-pyrazol-3-yl | O | H | H |
| 1-Me-pyrazol-3-yl | O | H | H |
| 1-Me-5-Me-pyrazol-3-yl | O | H | H |
| 1-Me-5-Et-pyrazol-3-yl | O | H | H |
| 1-Me-5-Pr-n-pyrazol-3-yl | O | H | H |
| 1-Me-5-CH₂F-pyrazol-3-yl | O | H | H |
| 1-Me-5-CHF₂-pyrazol-3-yl | O | H | H |
| 1-Me-5-CO₂Me-pyrazol-3-yl | O | H | H |
| 1-Me-5-CN-pyrazol-3-yl | O | H | H |
| 1-Me-5-NO₂-pyrazol-3-yl | O | H | H |
| 1-Me-5-F-pyrazol-3-yl | O | H | H |
| 1-Me-5-Cl-pyrazol-3-yl | O | H | H |
| 1-Me-5-Br-pyrazol-3-yl | O | H | H |

TABLE 5-continued

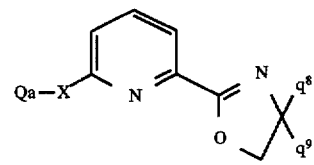

| Qa | X | q⁸ | q⁹ |
|---|---|---|---|
| 1-Me-5-I-pyrazol-3-yl | O | H | H |
| 1-Me-5-CF₃-4-Cl-pyrazol-3-yl | O | H | H |
| 1-Me-5-CF₃-4-Br-pyrazol-3-yl | O | H | H |
| 2-CF₃—Ph | O | H | Me |
| 3-CF₃—Ph | O | H | Me |
| 4-CF₃—Ph | O | H | Me |
| 2-Me—Ph | O | H | Me |
| 3-Me—Ph | O | H | Me |
| 4-Me—Ph | O | H | Me |
| 2-Et—Ph | O | H | Me |
| 3-Et—Ph | O | H | Me |
| 4-Et—Ph | O | H | Me |
| 2-MeO—Ph | O | H | Me |
| 3-MeO—Ph | O | H | Me |
| 4-MeO—Ph | O | H | Me |
| 2-CN—Ph | O | H | Me |
| 3-CN—Ph | O | H | Me |
| 4-CN—Ph | O | H | Me |
| 2-NO₂—Ph | O | H | Me |
| 3-NO₂—Ph | O | H | Me |
| 4-NO₂—Ph | O | H | Me |
| 2-F—Ph | O | H | Me |
| 3-F—Ph | O | H | Me |
| 4-F—Ph | O | H | Me |
| 2-Cl—Ph | O | H | Me |
| 3-Cl—Ph | O | H | Me |
| 4-Cl—Ph | O | H | Me |
| 2-Br—Ph | O | H | Me |
| 3-Br—Ph | O | H | Me |
| 4-Br—Ph | O | H | Me |
| 2-I—Ph | O | H | Me |
| 3-I—Ph | O | H | Me |
| 4-I—Ph | O | H | Me |
| 1-Me-3-CF₃-pyrazol-5-yl | O | H | Me |
| 1-Me-3-CF₃CF₂-pyrazol-5-yl | O | H | Me |
| 1-Me-3-CF₃CF₂CF₂-pyrazol-5-yl | O | H | Me |
| 1-Me-pyrazol-5-yl | O | H | Me |
| 1-Me-3-Me-pyrazol-5-yl | O | H | Me |
| 1-Me-3-Et-pyrazol-5-yl | O | H | Me |
| 1-Me-3-Pr-n-pyrazol-5-yl | O | H | Me |
| 1-Me-3-CH₂F-pyrazol-5-yl | O | H | Me |
| 1-Me-3-CHF₂-pyrazol-5-yl | O | H | Me |
| 1-Me-3-CO₂Me-pyrazol-5-yl | O | H | Me |
| 1-Me-3-CN-pyrazol-5-yl | O | H | Me |
| 1-Me-3-NO₂-pyrazol-5-yl | O | H | Me |
| 1-Me-3-F-pyrazol-5-yl | O | H | Me |
| 1-Me-3-Cl-pyrazol-5-yl | O | H | Me |
| 1-Me-3-Br-pyrazol-5-yl | O | H | Me |
| 1-Me-3-I-pyrazol-5-yl | O | H | Me |
| 1-Me-3-CF₃-4-Cl-pyrazol-5-yl | O | H | Me |
| 1-Me-3-CF₃-4-Br-pyrazol-5-yl | O | H | Me |
| 1-Et-3-CF₃-pyrazol-5-yl | O | H | Me |
| 1-Et-3-CF₃CF₂-pyrazol-5-yl | O | H | Me |
| 1-Et-3-CF₃CF₂CF₂-pyrazol-5-yl | O | H | Me |
| 1-Et-pyrazol-5-yl | O | H | Me |
| 1-Et-3-Me-pyrazol-5-yl | O | H | Me |
| 1-Et-3-Et-pyrazol-5-yl | O | H | Me |
| 1-Et-3-Pr-n-pyrazol-5-yl | O | H | Me |
| 1-Et-3-CH₂F-pyrazol-5-yl | O | H | Me |
| 1-Et-3-CHF₂-pyrazol-5-yl | O | H | Me |
| 1-Et-3-CO₂Me-pyrazol-5-yl | O | H | Me |
| 1-Et-3-CN-pyrazol-5-yl | O | H | Me |
| 1-Et-3-NO₂-pyrazol-5-yl | O | H | Me |
| 1-Et-3-F-pyrazol-5-yl | O | H | Me |
| 1-Et-3-Cl-pyrazol-5-yl | O | H | Me |
| 1-Et-3-Br-pyrazol-5-yl | O | H | Me |
| 1-Et-3-I-pyrazol-5-yl | O | H | Me |
| 1-Et-3-CF₃-4-Cl-pyrazol-5-yl | O | H | Me |

TABLE 5-continued

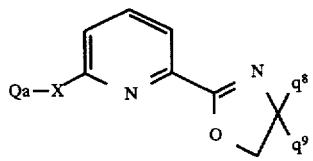

| Qa | X | q⁸ | q⁹ |
|---|---|---|---|
| 1-Et-3-CF₃-4-Br-pyrazol-5-yl | O | H | Me |
| 1-Me-5-CF₃-pyrazol-3-yl | O | H | Me |
| 1-Me-5-CF₃CF₂-pyrazol-3-yl | O | H | Me |
| 1-Me-5-CF₃CF₂CF₂-pyrazol-3-yl | O | H | Me |
| 1-Me-pyrazol-3-yl | O | H | Me |
| 1-Me-5-Me-pyrazol-3-yl | O | H | Me |
| 1-Me-5-Et-pyrazol-3-yl | O | H | Me |
| 1-Me-5-Pr-n-pyrazol-3-yl | O | H | Me |
| 1-Me-5-CH₂F-pyrazol-3-yl | O | H | Me |
| 1-Me-5-CHF₂-pyrazol-3-yl | O | H | Me |
| 1-Me-5-CO₂Me-pyrazol-3-yl | O | H | Me |
| 1-Me-5-CN-pyrazol-3-yl | O | H | Me |
| 1-Me-5-NO₂-pyrazol-3-yl | O | H | Me |
| 1-Me-5-F-pyrazol-3-yl | O | H | Me |
| 1-Me-5-Cl-pyrazol-3-yl | O | H | Me |
| 1-Me-5-Br-pyrazol-3-yl | O | H | Me |
| 1-Me-5-I-pyrazol-3-yl | O | H | Me |
| 1-Me-5-CF₃-4-Cl-pyrazol-3-yl | O | H | Me |
| 1-Me-5-CF₃-4-Br-pyrazol-3-yl | O | H | Me |
| 2-CF₃—Ph | O | Me | Me |
| 3-CF₃—Ph | O | Me | Me |
| 4-CF₃—Ph | O | Me | Me |
| 2-Me—Ph | O | Me | Me |
| 3-Me—Ph | O | Me | Me |
| 4-Me—Ph | O | Me | Me |
| 2-Et—Ph | O | Me | Me |
| 3-Et—Ph | O | Me | Me |
| 4-Et—Ph | O | Me | Me |
| 2-MeO—Ph | O | Me | Me |
| 3-MeO—Ph | O | Me | Me |
| 4-MeO—Ph | O | Me | Me |
| 2-CN—Ph | O | Me | Me |
| 3-CN—Ph | O | Me | Me |
| 4-CN—Ph | O | Me | Me |
| 2-NO₂—Ph | O | Me | Me |
| 3-NO₂—Ph | O | Me | Me |
| 4-NO₂—Ph | O | Me | Me |
| 2-F—Ph | O | Me | Me |
| 3-F—Ph | O | Me | Me |
| 4-F—Ph | O | Me | Me |
| 2-Cl—Ph | O | Me | Me |
| 3-Cl—Ph | O | Me | Me |
| 4-Cl—Ph | O | Me | Me |
| 2-Br—Ph | O | Me | Me |
| 3-Br—Ph | O | Me | Me |
| 4-Br—Ph | O | Me | Me |
| 2-I—Ph | O | Me | Me |
| 3-I—Ph | O | Me | Me |
| 4-I—Ph | O | Me | Me |
| 1-Me-3-CF₃-pyrazol-5-yl | O | Me | Me |
| 1-Me-3-CF₃CF₂-pyrazol-5-yl | O | Me | Me |
| 1-Me-3-CF₃CF₂CF₂-pyrazol-5-yl | O | Me | Me |
| 1-Me-pyrazol-5-yl | O | Me | Me |
| 1-Me-3-Me-pyrazol-5-yl | O | Me | Me |
| 1-Me-3-Et-pyrazol-5-yl | O | Me | Me |
| 1-Me-3-Pr-n-pyrazol-5-yl | O | Me | Me |
| 1-Me-3-CH₂F-pyrazol-5-yl | O | Me | Me |
| 1-Me-3-CHF₂-pyrazol-5-yl | O | Me | Me |
| 1-Me-3-CO₂Me-pyrazol-5-yl | O | Me | Me |
| 1-Me-3-CN-pyrazol-5-yl | O | Me | Me |
| 1-Me-3-NO₂-pyrazol-5-yl | O | Me | Me |
| 1-Me-3-F-pyrazol-5-yl | O | Me | Me |
| 1-Me-3-Cl-pyrazol-5-yl | O | Me | Me |
| 1-Me-3-Br-pyrazol-5-yl | O | Me | Me |
| 1-Me-3-I-pyrazol-5-yl | O | Me | Me |
| 1-Me-3-CF₃-4-Cl-pyrazol-5-yl | O | Me | Me |
| 1-Me-3-CF₃-4-Br-pyrazol-5-yl | O | Me | Me |
| 1-Et-3-CF₃-pyrazol-5-yl | O | Me | Me |

TABLE 5-continued

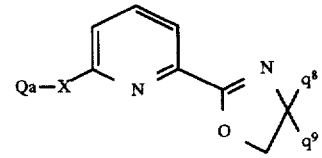

| Qa | X | q⁸ | q⁹ |
|---|---|---|---|
| 1-Et-3-CF₃CF₂-pyrazol-5-yl | O | Me | Me |
| 1-Et-3-CF₃CF₂CF₂-pyrazol-5-yl | O | Me | Me |
| 1-Et-pyrazol-5-yl | O | Me | Me |
| 1-Et-3-Me-pyrazol-5-yl | O | Me | Me |
| 1-Et-3-Et-pyrazol-5-yl | O | Me | Me |
| 1-Et-3-Pr-n-pyrazol-5-yl | O | Me | Me |
| 1-Et-3-CH₂F-pyrazol-5-yl | O | Me | Me |
| 1-Et-3-CHF₂-pyrazol-5-yl | O | Me | Me |
| 1-Et-3-CO₂Me-pyrazol-5-yl | O | Me | Me |
| 1-Et-3-CN-pyrazol-5-yl | O | Me | Me |
| 1-Et-3-NO₂-pyrazol-5-yl | O | Me | Me |
| 1-Et-3-F-pyrazol-5-yl | O | Me | Me |
| 1-Et-3-Cl-pyrazol-5-yl | O | Me | Me |
| 1-Et-3-Br-pyrazol-5-yl | O | Me | Me |
| 1-Et-3-I-pyrazol-5-yl | O | Me | Me |
| 1-Et-3-CF₃-4-Cl-pyrazol-5-yl | O | Me | Me |
| 1-Et-3-CF₃-4-Br-pyrazol-5-yl | O | Me | Me |
| 1-Me-5-CF₃-pyrazol-3-yl | O | Me | Me |
| 1-Me-5-CF₃CF₂-pyrazol-3-yl | O | Me | Me |
| 1-Me-5-CF₃CF₂CF₂-pyrazol-3-yl | O | Me | Me |
| 1-Me-pyrazol-3-yl | O | Me | Me |
| 1-Me-5-Me-pyrazol-3-yl | O | Me | Me |
| 1-Me-5-Et-pyrazol-3-yl | O | Me | Me |
| 1-Me-5-Pr-n-pyrazol-3-yl | O | Me | Me |
| 1-Me-5-CH₂F-pyrazol-3-yl | O | Me | Me |
| 1-Me-5-CHF₂-pyrazol-3-yl | O | Me | Me |
| 1-Me-5-CO₂Me-pyrazol-3-yl | O | Me | Me |
| 1-Me-5-CN-pyrazol-3-yl | O | Me | Me |
| 1-Me-5-NO₂-pyrazol-3-yl | O | Me | Me |
| 1-Me-5-F-pyrazol-3-yl | O | Me | Me |
| 1-Me-5-Cl-pyrazol-3-yl | O | Me | Me |
| 1-Me-5-Br-pyrazol-3-yl | O | Me | Me |
| 1-Me-5-I-pyrazol-3-yl | O | Me | Me |
| 1-Me-5-CF₃-4-Cl-pyrazol-3-yl | O | Me | Me |
| 1-Me-5-CF₃-4-Br-pyrazol-3-yl | O | Me | Me |
| 2-CF₃—Ph | O | H | Et |
| 3-CF₃—Ph | O | H | Et |
| 1-Me-3-CF₃-pyrazol-5-yl | O | H | Et |
| 1-Me-5-CF₃-pyrazol-3-yl | O | H | Et |
| 2-CF₃—Ph | O | Me | Et |
| 3-CF₃—Ph | O | Me | Et |
| 1-Me-3-CF₃-pyrazol-5-yl | O | Me | Et |
| 1-Me-5-CF₃-pyrazol-3-yl | O | Me | Et |
| 2-CF₃—Ph | O | Et | Et |
| 3-CF₃—Ph | O | Et | Et |
| 1-Me-3-CF₃-pyrazol-5-yl | O | Et | Et |
| 1-Me-5-CF₃-pyrazol-3-yl | O | Et | Et |
| 2-CF₃—Ph | O | H | Pr-i |
| 3-CF₃—Ph | O | H | Pr-i |
| 1-Me-3-CF₃-pyrazol-5-yl | O | H | Pr-i |
| 1-Me-5-CF₃-pyrazol-3-yl | O | H | Pr-i |
| 2-CF₃—Ph | O | Me | Pr-i |
| 3-CF₃—Ph | O | Me | Pr-i |
| 1-Me-3-CF₃-pyrazol-5-yl | O | Me | Pr-i |
| 1-Me-5-CF₃-pyrazol-3-yl | O | Me | Pr-i |
| 2-CF₃—Ph | S | Me | Me |
| 3-CF₃—Ph | S | Me | Me |
| 1-Me-3-CF₃-pyrazol-5-yl | S | Me | Me |
| 1-Me-5-CF₃-pyrazol-3-yl | S | Me | Me |
| 2-CF₃—Ph | NH | Me | Me |
| 3-CF₃—Ph | NH | Me | Me |
| 1-Me-3-CF₃-pyrazol-5-yl | NH | Me | Me |
| 1-Me-5-CF₃-pyrazol-3-yl | NH | Me | Me |
| 2-Cl-pyridin-4-yl | O | H | H |
| 2-Cl-pyridin-6-yl | O | H | H |
| 3-Cl-pyridin-5-yl | O | H | H |
| 3-Cl-pyridin-6-yl | O | H | H |
| 2-Cl-pyridin-4-yl | O | Me | H |

TABLE 5-continued

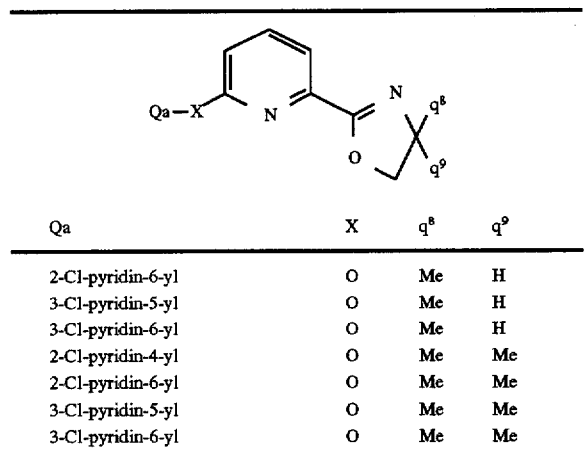

| Qa | X | q⁸ | q⁹ |
|---|---|---|---|
| 2-Cl-pyridin-6-yl | O | Me | H |
| 3-Cl-pyridin-5-yl | O | Me | H |
| 3-Cl-pyridin-6-yl | O | Me | H |
| 2-Cl-pyridin-4-yl | O | Me | Me |
| 2-Cl-pyridin-6-yl | O | Me | Me |
| 3-Cl-pyridin-5-yl | O | Me | Me |
| 3-Cl-pyridin-6-yl | O | Me | Me |

TABLE 6

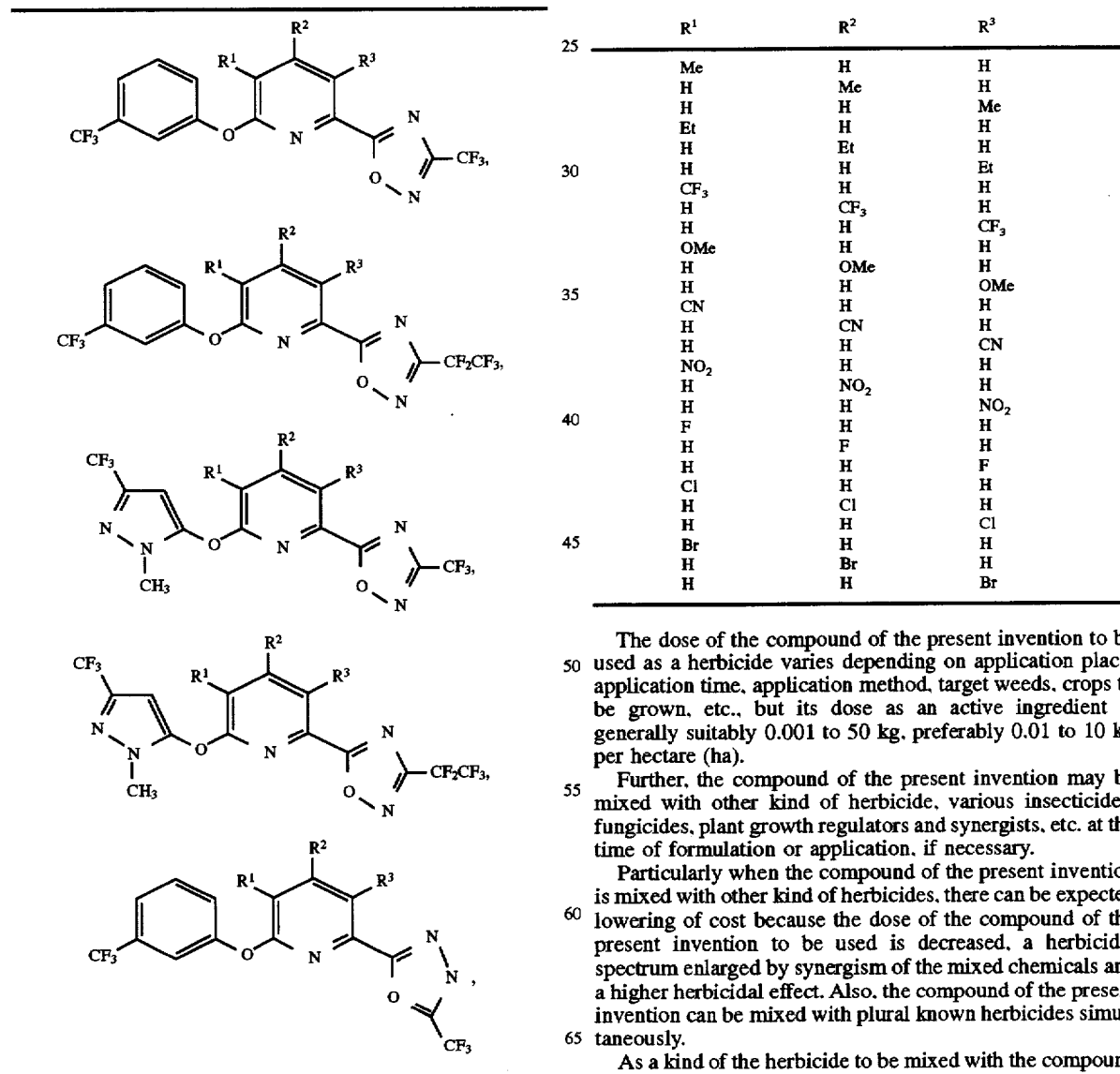

TABLE 6-continued

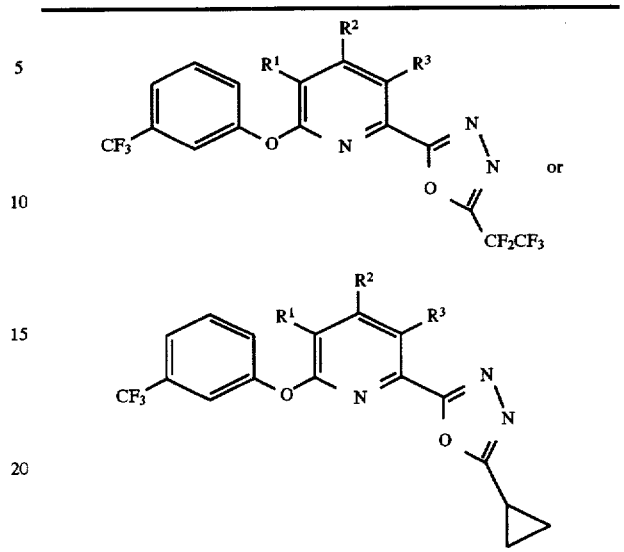

| $R^1$ | $R^2$ | $R^3$ |
|---|---|---|
| Me | H | H |
| H | Me | H |
| H | H | Me |
| Et | H | H |
| H | Et | H |
| H | H | Et |
| $CF_3$ | H | H |
| H | $CF_3$ | H |
| H | H | $CF_3$ |
| OMe | H | H |
| H | OMe | H |
| H | H | OMe |
| CN | H | H |
| H | CN | H |
| H | H | CN |
| $NO_2$ | H | H |
| H | $NO_2$ | H |
| H | H | $NO_2$ |
| F | H | H |
| H | F | H |
| H | H | F |
| Cl | H | H |
| H | Cl | H |
| H | H | Cl |
| Br | H | H |
| H | Br | H |
| H | H | Br |

The dose of the compound of the present invention to be used as a herbicide varies depending on application place, application time, application method, target weeds, crops to be grown, etc., but its dose as an active ingredient is generally suitably 0.001 to 50 kg, preferably 0.01 to 10 kg per hectare (ha).

Further, the compound of the present invention may be mixed with other kind of herbicide, various insecticides, fungicides, plant growth regulators and synergists, etc. at the time of formulation or application, if necessary.

Particularly when the compound of the present invention is mixed with other kind of herbicides, there can be expected lowering of cost because the dose of the compound of the present invention to be used is decreased, a herbicidal spectrum enlarged by synergism of the mixed chemicals and a higher herbicidal effect. Also, the compound of the present invention can be mixed with plural known herbicides simultaneously.

As a kind of the herbicide to be mixed with the compound of the present invention, there may be mentioned, for example, compounds described in Farm Chemicals Handbook published in 1993, etc.

As a preferred chemical to be used by mixing with the compound of the present invention, there may be mentioned, for example, pyrazosulfuron ethyl (common name), bensulfuron methyl (common name), cinosulfuron (common name), imazosulfuron (common name) and DPX-A8947 (N-(((4,6-dimethoxypyrimidin-2-yl)amino-carbonyl))-1-methyl-4-(2-methyl-2H-tetrazol-5-yl)-1H-pyrazole-5-sulfonamide).

Also, in addition to these chemicals, the following components may be further added.

There may be mentioned pretilachlor (common name), esprocarb (common name), pyrazolate (common name), pyrazoxyfen (common name), benzofenap (common name), dymron (common name), bromobutide (common name), naproanilide (common name), clomeprop (common name), CNP (common name), chlomethoxynil (common name), bifenox (common name), oxadiazon (common name), mefenacet (common name), butachlor (common name), butenachlor (common name), dithiopyr (common name), benfuresate (common name), pyributicarb (common name), benthiocarb (common name), dimepiperate (common name), molinate (common name), butamifos (common name), quinclorac (common name), cirmethylin (common name), simetryn (common name), SAP (bensulide/common name), dimethametryn (common name), MCPA, MCPB, 2',3'-dichloro-4-ethoxymethoxybenzanilide (test name is HW-52), 1-(2-chlorobenzyl)-3-(α,α-dimethylbenzyl)urea (test name is JC-1940), N-[2'-(3'-methoxy)-thienylmethyl]-N-chloroacetyl-2,6-dimethylanilide (test name is NSK-850), etc.

When the compound of the present invention is used as a herbicide, it can be generally used by mixing with a suitable carrier, for example, a solid carrier such as clay, talc, bentonite, diatomaceous earth, white carbon, etc. or a liquid carrier such as water, alcohols (isopropanol, butanol, benzyl alcohol, furfuryl alcohol, etc.), aromatic hydrocarbons (toluene, xylene, etc.), ethers (anisole, etc.), ketones (cyclohexanone, isophorone, etc.), esters (butyl acetate, etc.), acid amides (N-methylpyrrolidone, etc.) or halogenated hydrocarbons (chlorobenzene, etc.) and others. If desired, by adding a surfactant, an emulsifying agent, a dispersant, a penetrant, a spreading agent, a thickener, an antifreezing agent, an anticoagulant, a stabilizer, etc., the compound of the present invention can be provided for practical use in any desired preparation form such as a liquid formulation, an emulsifiable concentrate, a wettable powder, a dry flowable powder, a flowable liquid, a dust, a granule, etc.

To describe a herbicidal granule for a paddy field, containing the compound of the present invention specifically, as a solid carrier, there may be mentioned kaolinite, montmorillonite, diatomaceous earth, bentonite, talc, clay, calcium carbonate, calcium sulfate, ammonium sulfate, etc., and as a surfactant, there may be mentioned alkylbenzenesulfonate, polyoxyethylene alkylaryl ether, lignosulfonate, alkylsulfosuccinate, polyoxyethylene aliphatic acid ester, naphthalenesulfonate, polyoxyethylene alkylaryl ether sulfate, alkylamine salt, tripolyphosphate, etc. The content of these surfactants is not particularly limited, but it is generally desirably in the range of 0.05 to 20 parts by weight based on 100 parts by weight of the granule of the present invention. Also, if necessary, a decomposition inhibitor such as epoxidized soybean oil, etc. may be contained in the granule of the present invention.

Next, formulation examples of preparations when the compound of the present invention is used are shown specifically. However, formulation examples of the present invention are not limited to these. In the following Formulation examples, "part" means part by weight.

[Wettable Powder]

| | |
|---|---|
| Compound of the present invention | 0.1 to 80 parts |
| Solid carrier | 10 to 90 parts |
| Surfactant | 1 to 10 parts |
| Others | 1 to 5 parts |

As others, there may be mentioned, for example, an anticoagulant, etc.

[Emulsifiable Concentrate]

| | |
|---|---|
| Compound of the present invention | 0.1 to 30 parts |
| Liquid carrier | 30 to 95 parts |
| Surfactant | 5 to 15 parts |

[Flowable Liquid]

| | |
|---|---|
| Compound of the present invention | 0.1 to 70 parts |
| Liquid carrier | 15 to 65 parts |
| Surfactant | 5 to 12 parts |
| Others | 5 to 30 parts |

As others, there may be mentioned, for example, an antifreezing agent, a thickener, etc.

[Granular Wettable Powder (Dry Flowable Powder)]

| | |
|---|---|
| Compound of the present invention | 0.1 to 90 parts |
| Solid carrier | 10 to 70 parts |
| Surfactant | 1 to 20 parts |

[Liquid Formulation]

| | |
|---|---|
| Compound of the present invention | 0.01 to 30 parts |
| Liquid carrier | 0.1 to 50 parts |
| Water | 50 to 99.99 parts |
| Others | 0.1 to 10 parts |

[Granule]

| | |
|---|---|
| Compound of the present invention | 0.01 to 10 parts |
| Solid carrier | 90 to 99.99 parts |
| Others | 0.1 to 10 parts |

[Formulation Example 1]

Wettable Powder

| | |
|---|---|
| Compound No. 1 of the present invention | 20 parts |
| Zeeklite A (kaolin type clay: trade name, produced by Zeeklite Kogyo K.K.) | 76 parts |

-continued

| | |
|---|---|
| Solpol 5039 (mixture of nonionic surfactant and anionic surfactant: trade name, produced by Toho Kagaku Kogyo K.K.) | 2 parts |
| Carplex (anticoagulant) (white carbon: trade name, produced by Shionogi Seiyaku K.K.) | 2 parts |

The above components are mixed uniformly and pulverized to prepare a wettable powder.

[Formulation Example 2]

Wettable Powder

| | |
|---|---|
| Compound No. 1 of the present invention | 40 parts |
| Zeeklite A (kaolin type clay: trade name, produced by Zeeklite Kogyo K.K.) | 54 parts |
| Solpol 5039 (mixture of nonionic surfactant and anionic surfactant: trade name, produced by Toho Kagaku Kogyo K.K.) | 2 parts |
| Carplex (anticoagulant) (white carbon: trade name, produced by Shionogi Seiyaku K.K.) | 4 parts |

The above components are mixed uniformly and pulverized to prepare a wettable powder.

[Formulation Example 3]

Emulsifiable Concentrate

| | |
|---|---|
| Compound No. 1 of the present invention | 5 parts |
| Xylene | 75 parts |
| Dimethylformamide | 15 parts |
| Solpol 2680 (mixture of nonionic surfactant and anionic surfactant: trade name, produced by Toho Kagaku Kogyo K.K.) | 5 parts |

The above components are mixed uniformly to prepare an emulsifiable concentrate.

[Formulation Example 4]

Flowable Liquid

| | |
|---|---|
| Compound No. 1 of the present invention | 25 parts |
| Agrisole S-710 (nonionic surfactant: trade name, produced by Kao K.K.) | 10 parts |
| Runox 1000C (anionic surfactant: trade name, produced by Toho Kagaku Kogyo K.K.) | 0.5 part |
| 1% Rodopol water (thickener: trade name, produced by Rohne Poulenc Co.) | 20 parts |
| Water | 44.5 parts |

The above components are mixed uniformly to prepare a flowable liquid.

[Formulation Example 5]

Flowable Liquid

| | |
|---|---|
| Compound No. 1 of the present invention | 40 parts |
| Agrisole S-710 (nonionic surfactant: trade name, produced by Kao K.K.) | 10 parts |
| Runox 1000C (anionic surfactant: trade | 0.5 part |
| name, produced by Toho Kagaku Kogyo K.K.) | |
| 1% Rodopol water (thickener: trade name, produced by Rohne Poulenc Co.) | 20 parts |
| Water | 29.5 parts |

The above components are mixed uniformly to prepare a flowable liquid.

[Formulation Example 6]

Granular Wettable Powder (Dry Flowable Powder)

| | |
|---|---|
| Compound No. 1 of the present invention | 75 parts |
| Isobam No. 1 (anionic surfactant: trade name, produced by Kuraray Isoprene Chemical K.K.) | 10 parts |
| Vanilex N (anionic surfactant: trade name, produced by Sanyo Kokusaku Pulp K.K.) | 5 parts |
| Carplex #80 (white carbon: trade name, produced by Shionogi Seiyaku K.K.) | 10 parts |

The above components are mixed uniformly and pulverized finely to prepare a dry flowable powder.

[Formulation Example 7]

Granule

| | |
|---|---|
| Compound No. 1 of the present invention | 1 part |
| Bentonite | 55 parts |
| Talc | 44 parts |

The above components are mixed uniformly and pulverized, and then a small amount of water is added thereto. The mixture is stirred, mixed and kneaded, and granulated by an extrusion type granulator, followed by drying, to prepare a granule.

When the above wettable powder, emulsifiable concentrate, flowable liquid or granular wettable powder is used, it is diluted to 50 to 1000-fold with water and sprayed so that its active ingredient is 0.001 to 50 kg, preferably 0.01 to 10 kg per hectare (ha).

The compound of the present invention can be used as a herbicide for a paddy field in either treatment of soil treatment under submerging condition or stem and foliar treatment. Also, the compound of the present invention can be used as a herbicide for an upland field in either treatment of soil treatment, soil incorporation treatment or stem and foliar treatment, and can be also applied suitably to control of various kinds of weeds in noncultivated fields such as a playground, a vacant land, a space beside a railroad track, etc. other than the agricultural and horticultural field such as a paddy field, an upland field, an orchard, etc.

Next, usefulness of the compound of the present invention as a herbicide is described specifically by referring to the following Test examples.

Test Example 1

Test of Herbicidal Effects by Soil Treatment

Plastic boxes each having a length of 21 cm, a width of 13 cm and a depth of 7 cm were packed with sterilized diluvial soil, planted with seeds of barnyardgrass (A), green foxtail (B), velvetleaf (C), redroot pigweed (D), morning glory (E), soybean (a), cotton (b) and corn (c) in a spotted state, respectively, and covered with about 1.5 cm of soil. Then, chemical solutions were uniformly sprayed on the soil surfaces by small sprays so that the amounts of the active ingredients of the compounds of the present invention became specific ratios. The chemical solutions for spraying were used by diluting wettable powders suitably prepared according to Formulation examples described above, etc. with water. Three weeks after spraying the chemical solutions, herbicidal effects on the crops and the weeds were examined according to a judgment standard described below. The degree of control was determined by observation with naked eyes.

5: Completely killed or 90% or more of control

4: 70% to 90% of control

3: 40% to 70% of control

2: 20% to 40% of control

1: 5% to 20% of control

0: less than 5% of control

The results are shown in Table 7.

TABLE 7

| Compound No. | Dosage (kg/ha) | A | B | C | D | E | a | b | c |
|---|---|---|---|---|---|---|---|---|---|
| 1 | 5 | 5 | 5 | 0 | 5 | 4 | 0 | 0 | 2 |
| 2 | 5 | 5 | 5 | 0 | 5 | 4 | 0 | 0 | 2 |
| 3 | 5 | 5 | 5 | 5 | 5 | 5 | 0 | 0 | 3 |
| 4 | 2.5 | 5 | 5 | 5 | 5 | 5 | 2 | 0 | 2 |
| 10 | 5 | 5 | 5 | 2 | 5 | 2 | 0 | 0 | 0 |
| 11 | 2.5 | 5 | 5 | 0 | 5 | 0 | 0 | 0 | 0 |
| 12 | 5 | 5 | 5 | 5 | 5 | 4 | 0 | 0 | 0 |
| 14 | 0.63 | 5 | 5 | 0 | 5 | 0 | 0 | 0 | 0 |
| 16 | 5 | 4 | 5 | 0 | 5 | 0 | 0 | 0 | 0 |
| 21 | 0.63 | 5 | 5 | 4 | 5 | 4 | 0 | 0 | 0 |
| 22 | 0.63 | 5 | 5 | 5 | 5 | 5 | 0 | 0 | 0 |
| 23 | 0.63 | 5 | 5 | 4 | 5 | 5 | 0 | 0 | 0 |
| 27 | 0.63 | 5 | 5 | 0 | 5 | 0 | 0 | 0 | 0 |
| 28 | 0.63 | 5 | 5 | 0 | 5 | 5 | 0 | 0 | 0 |
| 30 | 25 | 5 | 5 | 4 | 5 | 4 | 0 | 0 | 0 |
| 32 | 0.63 | 5 | 5 | 4 | 5 | 1 | 0 | 0 | 0 |
| 33 | 0.63 | 5 | 5 | 4 | 5 | 5 | 0 | 0 | 0 |
| 34 | 2.5 | 5 | 5 | 1 | 5 | 1 | 0 | 0 | 0 |
| 35 | 0.63 | 5 | 5 | 5 | 5 | 5 | 0 | 0 | 0 |
| 46 | 0.16 | 5 | 5 | 1 | 5 | 4 | 0 | 0 | 2 |
| 47 | 0.16 | 5 | 5 | 0 | 5 | 2 | 0 | 0 | 0 |
| 48 | 0.16 | 5 | 5 | 0 | 5 | 0 | 0 | 0 | 0 |
| 49 | 0.63 | 5 | 5 | 5 | 5 | 0 | 0 | 0 | 0 |
| 51 | 0.16 | 5 | 5 | 0 | 5 | 2 | 0 | 0 | 0 |
| 54 | 2.5 | 5 | 5 | 0 | 5 | 0 | 0 | 0 | 0 |
| 55 | 2.5 | 5 | 5 | 0 | 5 | 2 | 0 | 0 | 0 |
| 57 | 0.63 | 5 | 5 | 0 | 5 | 3 | 0 | 0 | 0 |
| 60 | 2.5 | 5 | 5 | 0 | 5 | 4 | 0 | 0 | 1 |

Test Example 2

Test of Herbicidal Effects by Stem and Foliar Treatment

Plastic boxes each having a length of 21 cm, a width of 13 cm and a depth of 7 cm were packed with sterilized diluvial soil, planted with seeds of barnyardgrass (A), green foxtail (B), velvetleaf (C), redroot pigweed (D), morning glory (E) and cocklebur (F) in a spotted state, respectively, and covered with about 1.5 cm of soil. When the respective plants reached 2 or 3 leaf stage, chemical solutions were uniformly sprayed on the stem and foliar portions by small sprays so that the amounts of the active ingredients of the compounds of the present invention became specific ratios. The chemical solutions for spraying were used by diluting wettable powders suitably prepared according to Formulation examples described above, etc. with water. Three weeks after spraying the chemical solutions, herbicidal effects on the weeds were examined according to the judgment standard of Test example 1. The results are shown in Table 8.

TABLE 8

| Compound No. | Dosage (kg/ha) | A | B | C | D | E | F |
|---|---|---|---|---|---|---|---|
| 1 | 5 | 0 | 3 | 1 | 3 | 0 | 2 |
| 2 | 5 | 0 | 3 | 2 | 3 | 0 | 2 |
| 3 | 5 | 3 | 3 | 3 | 4 | 3 | 2 |
| 4 | 2.5 | 3 | 3 | 3 | 4 | 2 | 2 |
| 10 | 5 | 5 | 5 | 3 | 4 | 4 | 0 |
| 11 | 2.5 | 5 | 5 | 4 | 4 | 5 | 1 |
| 12 | 5 | 5 | 5 | 4 | 4 | 5 | 0 |
| 21 | 5 | 5 | 5 | 5 | 5 | 5 | 5 |
| 22 | 2.5 | 5 | 5 | 4 | 5 | 5 | 4 |
| 23 | 2.5 | 5 | 5 | 4 | 5 | 5 | 4 |
| 33 | 2.5 | 5 | 4 | 4 | 5 | 5 | 4 |
| 34 | 2.5 | 4 | 4 | 1 | 5 | 1 | 0 |
| 35 | 2.5 | 4 | 4 | 4 | 4 | 5 | 4 |
| 60 | 2.5 | 5 | 5 | 4 | 2 | 5 | 4 |

Test Example 3

Test of Herbicidal Effects Under Submerging Condition

Wagner pots each having an area of 1/10000 are were packed with alluvial soil, and water was poured into the pots mixed with the soil to make a submerging condition of a water depth being 4 cm. After seeds of barnyardgrass (A), bulrush (G), ducksalad (H) and toothcup (I) were sowed in the above pots, seedlings of rice (d) at 2.5 leaf stage were transplanted. One day after sowing, chemical solutions were subjected to dropwise treatment to the water surfaces by measuring pipettes so that the amounts of the active ingredients of the compounds of the present invention became specific ratios. The chemical solutions for dropwise addition were used by diluting wettable powders suitably prepared according to Formulation examples described above, etc. with water. The pots were placed in a greenhouse at 25° to 30° C., and the plants were grown. Three weeks after dropwise addition of the chemical solutions, herbicidal effects on rice and the weeds were examined according to the judgment standard of Test example 1. The results are shown in Table 9.

TABLE 9

| Compound No. | Dosage (kg/ha) | A | G | H | I | d |
|---|---|---|---|---|---|---|
| 1 | 2 | 5 | 5 | 5 | 5 | 4 |
| 2 | 2 | 5 | 5 | 5 | 5 | 4 |
| 3 | 2 | 5 | 5 | 5 | 5 | 2 |
| 4 | 1 | 5 | 5 | 5 | 5 | 0 |
| 10 | 2 | 5 | 5 | 5 | 5 | 0 |
| 11 | 1 | 5 | 5 | 5 | 5 | 0 |
| 12 | 2 | 5 | 5 | 5 | 5 | 2 |
| 15 | 0.25 | 4 | 5 | 5 | 5 | 0 |
| 16 | 2 | 5 | 5 | 5 | 5 | 0 |
| 18 | 1 | 5 | 5 | 5 | 5 | 0 |
| 20 | 2 | 5 | 5 | 5 | 5 | 0 |
| 21 | 1 | 5 | 5 | 5 | 5 | 0 |
| 22 | 0.25 | 5 | 5 | 5 | 5 | 0 |
| 23 | 0.25 | 5 | 5 | 5 | 5 | 0 |
| 26 | 1 | 5 | 2 | 5 | 5 | 0 |
| 27 | 0.25 | 5 | 4 | 5 | 5 | 0 |
| 28 | 1 | 5 | 5 | 5 | 5 | 0 |
| 30 | 0.25 | 5 | 5 | 5 | 5 | 0 |

TABLE 9-continued

| Compound No. | Dosage (kg/ha) | A | G | H | I | d |
|---|---|---|---|---|---|---|
| 31 | 0.25 | 5 | 5 | 5 | 5 | 0 |
| 32 | 0.25 | 5 | 5 | 5 | 5 | 1 |
| 33 | 0.25 | 5 | 5 | 5 | 5 | 2 |
| 34 | 0.25 | 5 | 5 | 5 | 5 | 0 |
| 35 | 0.25 | 5 | 5 | 5 | 5 | 1 |
| 36 | 1 | 5 | 5 | 5 | 5 | 0 |
| 38 | 1 | 5 | 2 | 5 | 5 | 0 |
| 41 | 0.25 | 5 | 5 | 5 | 5 | 0 |
| 46 | 0.06 | 5 | 5 | 5 | 5 | 0 |
| 47 | 0.06 | 5 | 5 | 5 | 5 | 0 |
| 48 | 0.06 | 5 | 4 | 5 | 5 | 0 |
| 49 | 0.25 | 5 | 5 | 5 | 5 | 0 |
| 51 | 0.06 | 5 | 4 | 5 | 5 | 0 |
| 52 | 0.06 | 5 | 4 | 5 | 5 | 1 |
| 53 | 1 | 5 | 5 | 5 | 5 | 0 |
| 54 | 1 | 5 | 5 | 5 | 5 | 1 |
| 55 | 0.06 | 5 | 2 | 5 | 5 | 0 |
| 56 | 1 | 5 | 5 | 5 | 5 | 2 |
| 57 | 1 | 5 | 5 | 5 | 5 | 2 |
| 58 | 1 | 5 | 5 | 5 | 5 | 0 |
| 60 | 1 | 5 | 5 | 5 | 5 | 0 |
| 62 | 1 | 5 | 5 | 5 | 5 | 2 |

We claim:

1. A pyridine derivative represented by the formula (1):

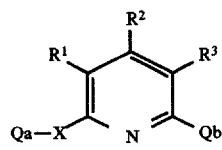

(1)

wherein $R^1$, $R^2$ and $R^3$ each independently represent a hydrogen atom, a $C_{1-6}$ alkyl group, a $C_{1-4}$ haloalkyl group, a $C_{1-4}$ alkoxy group, a cyano group, a nitro group or a halogen atom, Qa represents

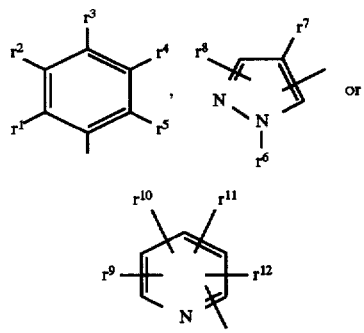

wherein $r^1$, $r^2$, $r^3$, $r^4$ and $r^5$ each independently represent a hydrogen atom, a $C_{1-4}$ alkyl group, a $C_{1-4}$ haloalkyl group, a $C_{1-4}$ alkoxy group, a cyano group, a nitro group or a halogen atom, $r^6$ represents a hydrogen atom, a $C_{1-6}$ alkyl group, a $C_{3-6}$ cycloalkyl group which may be substituted by a $C_{1-4}$ alkyl group, a $C_{2-4}$ alkenyl group, a $C_{2-4}$ alkynyl group or a $C_{1-4}$ haloalkyl group, $r^7$ and $r^8$ each independently represent a hydrogen atom, a $C_{1-6}$ alkyl group, a $C_{3-6}$ cycloalkyl group, a $C_{2-4}$ alkenyl group, a $C_{2-4}$ alkynyl group, a $C_{1-4}$ haloalkyl group, a $C_{1-4}$ alkoxycarbonyl group, a cyano group, a halogen atom or a nitro group, and $r^9$, $r^{10}$, $r^{11}$ and $r^{12}$ each independently represent a hydrogen atom, a $C_{1-4}$ alkyl group, a $C_{1-4}$ haloalkyl group, a $C_{1-4}$ alkoxy group, a cyano group, a nitro group or a halogen atom.

Qb represents

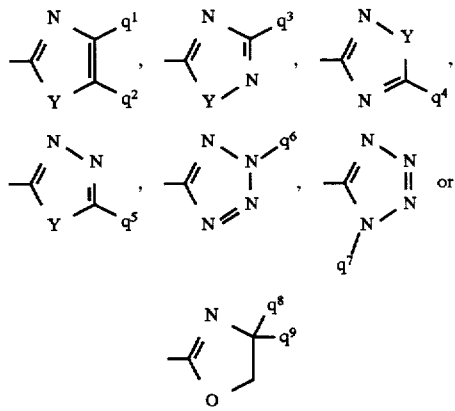

wherein $q^1$, $q^2$, $q^3$, $q^4$ and $q^5$ each independently represent a hydrogen atom, a $C_{1-6}$ alkyl group, a $C_{3-6}$ cycloalkyl group which may be substituted by a $C_{1-4}$ alkyl group or a halogen atom, a $C_{1-4}$ haloalkyl group, a $C_{1-4}$ alkoxy group, a cyano group, a nitro group, a halogen atom, a $C_{1-4}$ alkoxy $C_{1-4}$ alkyl group, a $C_{1-4}$ haloalkoxy $C_{1-4}$ alkyl group, a phenyl group, a benzyl group, a 3-pyridyl group, a $C_{1-4}$ alkoxycarbonyl group, a $C_{2-4}$ alkenyl group which may be substituted by a halogen atom, a $C_{1-4}$ haloalkoxy group, a $C_{1-4}$ alkylthio group, a $C_{1-4}$ alkylsulfinyl group, a $C_{1-4}$ alkylsulfonyl group, a $C_{2-4}$ alkenyloxy group, a $C_{3-4}$ alkynyloxy group, a $C_{1-4}$ haloalkylthio group, a $C_{2-4}$ alkenylthio group, a $C_{3-4}$ alkynylthio group, a $C_{1-4}$ alkylamino group, a $C_{2-4}$ haloalkylamino group, a di-$C_{1-4}$ alkylamino group, a carbamoyl group, a N-cyclopropylcarbamoyl group, a hydroxyl group, an epoxy group which may be substituted by a $C_{1-4}$ alkyl group, or a di-$C_{2-4}$ haloalkylamino group, $q^6$, $q^7$, $q^8$ and $q^9$ each independently represent a hydrogen atom or a $C_{1-6}$ alkyl group, Y represents an oxygen atom, a sulfur atom or N-$q^{10}$, and $q^{10}$ represents a hydrogen atom or a $C_{1-4}$ alkyl group, X represents an oxygen atom, a sulfur atom or N-$R^4$, and $R^4$ represents a hydrogen atom or a $C_{1-4}$ alkyl group.

2. The pyridine derivative according to claim 1, wherein $R^1$, $R^2$ and $R^3$ are selected from a hydrogen atom, a methyl group, an ethyl group, a n-propyl group, an iso-propyl group, a n-butyl group, an iso-butyl group, a sec-butyl group, a tert-butyl group, a n-pentyl group, a n-hexyl group, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $C_{12}CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, a methoxy group, an ethoxy group, a n-propoxy group, an iso-propoxy group, a n-butoxy group, an iso-butoxy group, a tert-butoxy group, CN, $NO_2$, F, Cl, Br and I.

3. The pyridine derivative according to claim 1, wherein Qa is selected from the following substituents.

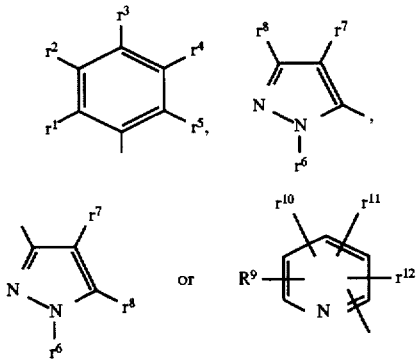

wherein $r^1$ to $r^{12}$ have the same meanings as described above.

4. The pyridine derivative according to claim 1, wherein $r^1$, $r^2$, $r^3$, $r^4$ and $r^5$ are selected from a hydrogen atom, a methyl group, an ethyl group, a n-propyl group, an iso-propyl group, a n-butyl group, an iso-butyl group, a sec-butyl group, a tert-butyl group, $CH_2F$, $CH_2Cl$, $CH_2Br$, $CH_2I$, $CHF_2$, $CHCl_2$, $CHBr_2$, $CF_3$, $CCl_3$, $CBr_3$, $CClF2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, a methoxy group, an ethoxy group, a n-propoxy group, an iso-propoxy group, a n-butoxy group, an iso-butoxy group, a tert-butoxy group, CN, $NO_2$, F, Cl, Br and I.

5. The pyridine derivative according to claim 1, wherein $r^6$ is selected from a hydrogen atom, a methyl group, an ethyl group, a n-propyl group, an iso-propyl group, a n-butyl group, an iso-butyl group, a sec-butyl group, a tert-butyl group, a n-pentyl group, a n-hexyl group, a cyclopropyl group, a cyclobutyl group, a cyclopentyl group, a cyclohexyl group, $CH_2CH=CH_2$, $CH_2CH=CHMe$, $CH_2CH_2CH=CH_2$, $CH_2C\equiv CH$, $CH_2C\equiv CMe$, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$ and $ClCH_2CH_2CH_2CH_2$.

6. The pyridine derivative according to claim 1, wherein $r^7$ and $r^8$ are selected from a hydrogen atom, a methyl group, an ethyl group, a n-propyl group, an iso-propyl group, a n-butyl group, an iso-butyl group, a sec-butyl group, a tert-butyl group, a n-pentyl group, a n-hexyl group, a cyclopropyl group, a cyclobutyl group, a cyclopentyl group, a cyclohexyl group, $CH_2CH=CH_2$, $CH_2CH=CHMe$, $CH_2CH_2CH=CH_2$, $CH_2C\equiv CH$, $CH_2C\equiv CMe$, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, $CO_2Me$, $CO_2Et$, $CO_2Pr-n$, $CO_2Pr-iso$, $CO_2Bu-n$, CN, $NO_2$, F, Cl, Br and I.

7. The pyridine derivative according to claim 1, wherein $r^9$, $r^{10}$, $r^{11}$ and $r^{12}$ are selected from a hydrogen atom, a methyl group, an ethyl group, a n-propyl group, an iso-propyl group, a n-butyl group, an iso-butyl group, a sec-butyl group, a tert-butyl group, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, a methoxy group, an ethoxy group, a n-propoxy group, an iso-propoxy group, a n-butoxy group, an iso-butoxy group, a tert-butoxy group, CN, $NO_2$, F, Cl, Br and I.

8. The pyridine derivative according to claim 1, wherein $q^1$, $q^2$, $q^3$, $q^4$ and $q^5$ are selected from a hydrogen atom, a methyl group, an ethyl group, a n-propyl group, an iso-propyl group, a n-butyl group, an iso-butyl group, a sec-butyl group, a tert-butyl group, a n-pentyl group, a n-hexyl group, a cyclopropyl group, a cyclobutyl group, a cyclopentyl group, a cyclohexyl group, $CH_2F$, $CH_2Cl$, $CH_2Br$, $CH_2I$, $CHF_2$, $CHCl_2$, $CHBr_2$, $CF_3$, $CCl_3$, $CBr_3$, $CClF_2$, $CF_3CH_2$, $CF_3CF_2$, $ClCH_2CH_2$, $Cl_2CHCH_2$, $Cl_3CCH_2$, $BrCH_2CH_2$, $Br_2CHCH_2$, $ICH_2CH_2$, $CF_3CH_2CH_2$, $CF_3CF_2CH_2$, $CF_3CF_2CF_2$, $CF_3CH_2CH_2CH_2$, $CF_3CF_2CH_2CH_2$, $CF_3CF_2CF_2CH_2$, $ClCH_2CH_2CH_2$, $ClCH_2CH_2CH_2CH_2$, a methoxy group, an ethoxy group, a n-propoxy group, an iso-propoxy group, a n-butoxy group, an iso-butoxy group, a tert-butoxy group, CN, $NO_2$, F, Cl, Br, I, $CH_2OMe$, $CH_2CH_2OMe$, $CH_2CH_2CH_2OMe$, $CH_2CH_2CH_2CH_2OMe$, $CH_2OEt$, $CH_2OPr-n$, $CH_2OBu-n$, $CH_2OCH_2CF_3$, $CH_2CH_2OCH_2CF_3$, $CH_2CH_2CH_2OCH_2CF_3$, $CH_2CH_2CH_2CH_2OCH_2CF_3$, $CH_2OCH_2CH_2F$, $CH_2OCH_2CH_2Cl$, $CH_2OCH_2CH_2Br$, Ph, $PhCH_2$, 3-Py, $CO_2Me$, $CO_2Et$, $CO_2Pr-n$, $CO_2Bu-n$, $CH=CH_2$, $CH=CHMe$, $CH=CMe_2$, $CH_2CH=CH_2$, $CH_2CH=CHMe$, $OCH_2F$, $OCHF_2$, $OCF_3$, $OCBrF_2$, $OCH_2CF_3$, $OCF_2CF_3$, $OCH_2CH_2Cl$, $OCH_2CHCl_2$, $OCH_2CH_2CF_3$, $OCH_2CF_2CF_3$, $OCF_2CF_2CF_3$, $OCH_2CH_2CH_2CH_2Cl$, SMe, SEt, SPr-n, SPr-iso, SBu-n, S(O)Me, S(O)Et, S(O)Pr-n, S(O)Pr-iso, S(O)Bu-n, $SO_2Me$, $SO_2Et$, $SO_2Pr-n$, $SO_2Pr-iso$, $SO_2Bu-n$, $OCH=CH_2$, $OCH=CHMe$, $OCH=CMe_2$, $OCH_2CH=CH_2$, $OCH_2CH=CHMe$, $OCH_2C\equiv CH$, $OCH_2C\equiv CMe$, $SCH_2F$, $SCHF_2$, $SCF_3$, $SCBrF_2$, $SCH_2CF_3$, $SCF_2CF_3$, $SCH_2CH_2Cl$, $SCH_2CHCl_2$, $SCH_2CH_2CF_3$, $SCH_2CF_2CF_3$, $SCF_2CF_2CF_3$, $SCH_2CH_2CH_2CH_2Cl$, $SCH=CH_2$, $SCH=CHMe$, $SCH=CMe_2$, $SCH_2CH=CH_2$, $SCH_2CH=CHMe$, $SCH_2C\equiv CH$, $SCH_2C\equiv CMe$, NHMe, NHEt, NHPr-n, NHPr-iso, NHBu-n, $NHCH_2CF_3$, $NHCF_2CF_3$, $NHCH_2CH_2Cl$, $NHCH_2CHCl_2$, $NHCH_2CH_2CF_3$, $NHCH_2CF_2CF_3$, $NHCF_2CF_2CF_3$, $NHCH_2CH_2CH_2CH_2Cl$, $NMe_2$, $NEt_2$, $N(Pr-n)_2$, $N(Pr-iso)_2$, $N(Bu-n)_2$, $N(CH_2CF_3)_2$, $N(CF_2CF_3)_2$, $N(CH_2CH_2Cl)_2$, $N(CH_2CHCl_2)_2$, $N(CH_2CH_2CF_3)_2$, $N(CH_2CF_2CF_3)_2$, $N(CF_2CF_2CF_3)_2$, $N(CH_2CH_2CH_2CH_2Cl)_2$, a 2-Me-cyclopropyl group, $CMe=CH_2$, $CONH_2$, a CONH-cyclopropyl group, OH, Epo, 1-Me-Epo, $CF_2Br$, $CF_2I$, $CFMe_2$, $CH(CF_3)_2$, $CH(CF_3)$ Me, $CF_2Me$, CHFMe, a 2-F-cyclopropyl group, a 2,2-$F_2$-cyclopropyl group, a 2,2,3,3-$F_4$-cyclopropyl group, a 2-Cl-cyclopropyl group, a 2,2-$Cl_2$-cyclopropyl group and $CH=CF_2$.

9. The pyridine derivative according to claim 1, wherein $q^6$, $q^7$, $q^8$ and $q^9$ are selected from a hydrogen atom, a methyl group, an ethyl group, a n-propyl group, an iso-propyl group, a n-butyl group, an iso-butyl group, a sec-butyl group, a tert-butyl group, a n-pentyl group and a n-hexyl group.

10. The pyridine derivative according to claim 1, wherein X and Y are selected from O, S, NH, NMe, NEt, NPr-n, NPr-iso, NBu-n, NBu-iso, NBu-sec and NBu-tert.

11. An agricultural composition which contains one or two or more of the compounds according to claim 1 as an active ingredient.

12. A herbicidal composition which contains one or two or more of the compounds according to claim 1 as an active ingredient.

13. A method of controlling weeds which comprises treatment of the soil, stem and/or foliar with a herbicidally effective composition which contains one or two or more of the compounds according to claim 1 as an active ingredient.

* * * * *